United States Patent
Patti et al.

(10) Patent No.: US 7,855,272 B2
(45) Date of Patent: Dec. 21, 2010

(54) **SDRE PROTEIN FROM *STAPHYLOCOCCUS AUREUS* AND DIAGNOSTIC KITS INCLUDING SAME**

(75) Inventors: Joseph M. Patti, Cumming, GA (US); Timothy J. Foster, Dublin (IE); Elisabet Josefsson, Gothenburg (SE); Deidre Ni Eidhin, Dublin (IE); Magnus A. O. Hook, Houston, TX (US); Samuel E. Perkins, Houston, TX (US)

(73) Assignees: Bioresearch Ireland, Dublin (IE); The Texas A&M University System, College Station, TX (US)

( * ) Notice: Subject to any disclaimer, the term of this patent is extended or adjusted under 35 U.S.C. 154(b) by 0 days.

(21) Appl. No.: 12/546,322

(22) Filed: Aug. 24, 2009

(65) Prior Publication Data

US 2010/0113349 A1    May 6, 2010

Related U.S. Application Data

(62) Division of application No. 10/744,616, filed on Dec. 24, 2003, now abandoned, which is a division of application No. 09/200,650, filed on Nov. 25, 1998, now Pat. No. 6,680,195.

(60) Provisional application No. 60/066,815, filed on Nov. 26, 1997, provisional application No. 60/098,427, filed on Aug. 31, 1998.

(51) Int. Cl.
*C07K 1/00* (2006.01)
(52) U.S. Cl. .................. 530/350; 530/387.9; 435/975
(58) Field of Classification Search .................. None
See application file for complete search history.

(56) References Cited

FOREIGN PATENT DOCUMENTS

WO        94/13310        *    6/1994

OTHER PUBLICATIONS

Yacoub et al (Eur. J. Bioche. 222:919-925, 1994).*

* cited by examiner

*Primary Examiner*—Patricia A Duffy
(74) *Attorney, Agent, or Firm*—B. Aaron Schulman; Terry L. Wright; Stites & Harbison PLLC

(57) ABSTRACT

An isolated extracellular matrix-binding protein, designated as SdrE and its corresponding amino acid and nucleic acid sequences and motifs are described. The proteins, peptides, fragments thereof or antigenic portions thereof are useful for the prevention, inhibition, treatment and diagnosis of *S. aureus* infection and as scientific research tools. Further, antibodies or antibody fragments to the proteins, peptides, fragments thereof or antigenic portions thereof are also useful for the prevention, inhibition, treatment and diagnosis of *S. aureus* infection. In particular, the proteins or antibodies thereof may be administered to wounds or used to coat biomaterials to act as blocking agents to prevent or inhibit the binding of *S. aureus* to wounds or biomaterials.

8 Claims, 34 Drawing Sheets

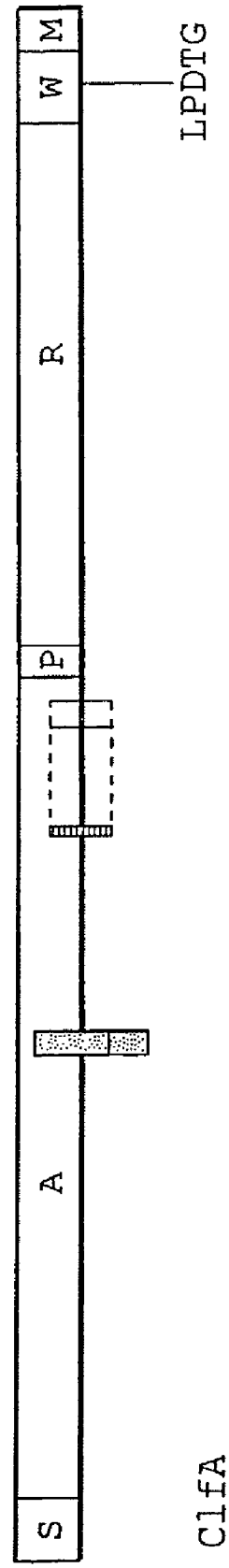
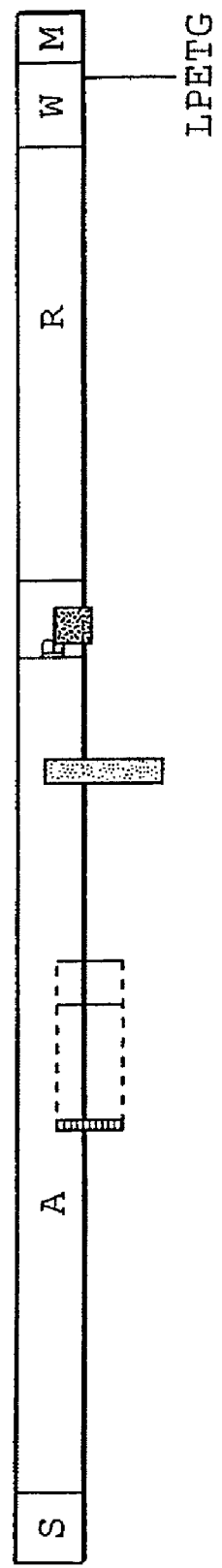
FIG. 1

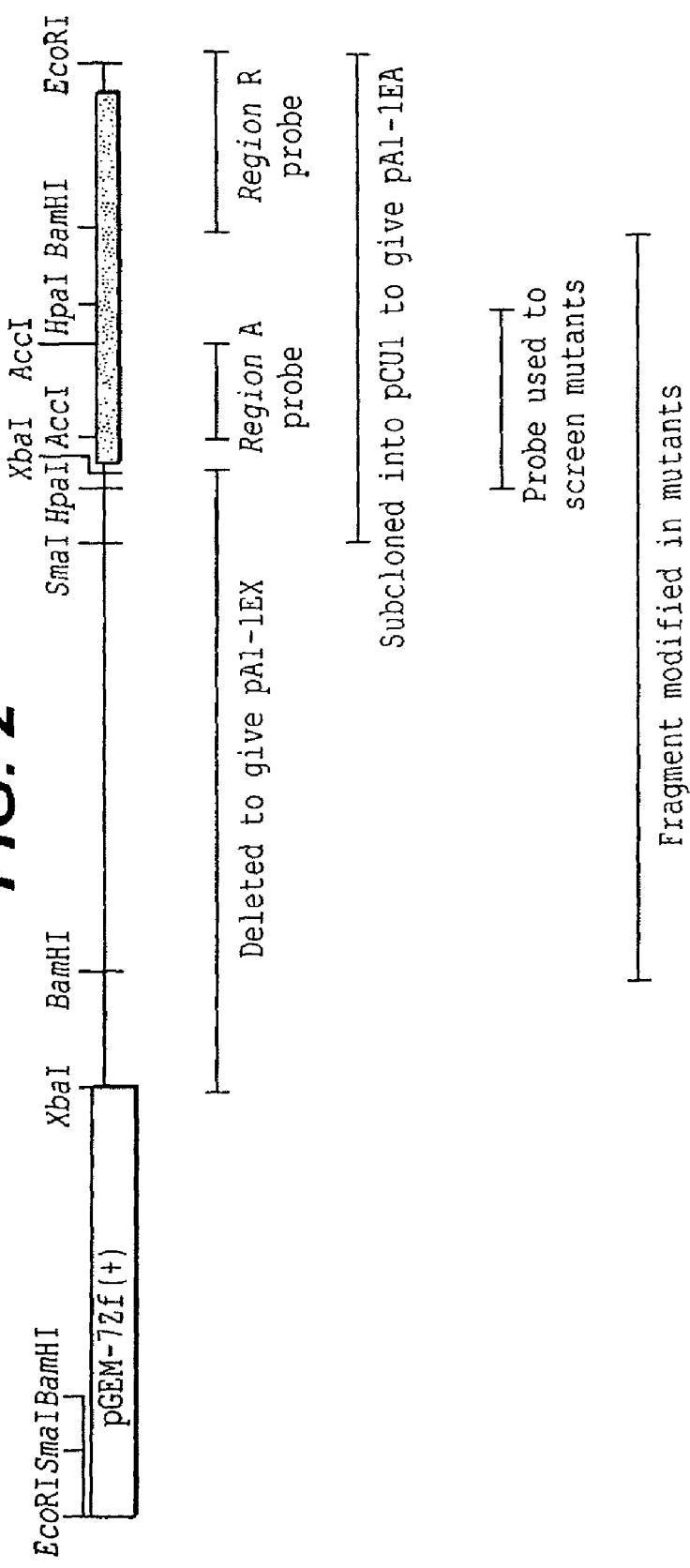
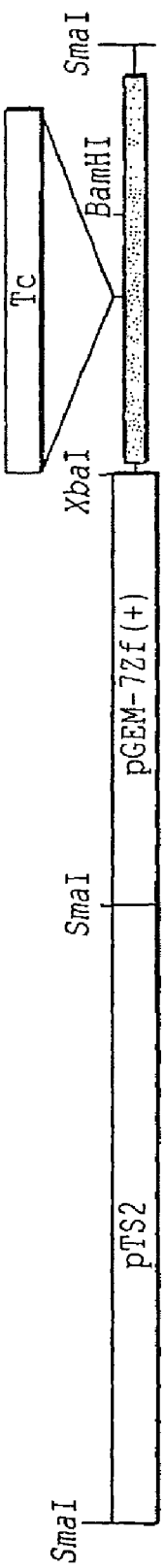
FIG. 2
FIG. 3

S>
TAGAAAATTGAAATGGAGTAATATTTTTGAAAAAAAGAATTGATTATTTGTCGAATAAGCAGAATAAGTATTCGATTAGACGTTTTACAGT
```
         N  G  V  I  F  L  K  K  R  I  D  Y  L  S  N  K  Q  N  K  Y  S  I  R  R  F  T  V  22
```
                                                                          A>
AGGTACCACATCAGTAATAGTAGGGGCAACTATACTATTTGGGATAGGCAATCATCAAGCACAAGCTTCAGAACAATCGAACGATACAAC
```
  G  T  T  S  V  I  V  G  A  T  I  L  F  G  I  G  N  H  Q  A  Q  A  S  E  Q  S  N  D  T  T  52
```
GCAATCTTCGAAAAATAATGCAAGTGCAGATTCCGAAAAAAACAATATGATAGAAACACCTCAATTAAATACAACGGCTAATGATACATC
```
  Q  S  S  K  N  N  A  S  A  D  S  E  K  N  N  M  I  E  T  P  Q  L  N  T  T  A  N  D  T  S  82
```
TGATATTAGTGCAAACACAAACAGTGCGAATGTAGATAGCACAACAAAACCAATGTCTACACAAACGAGCAATACCACTACAACAGAGCC
```
  D  I  S  A  N  T  N  S  A  N  V  D  S  T  T  K  P  M  S  T  Q  T  S  N  T  T  T  T  E  P  112
```
AGCTTCAACAAATGAAACACCTCAACCGACGGCAATTAAAAATCAAGCAACTGCTGCAAAAATGCAAGATCAAACTGTTCCTCAAGAAGG
```
  A  S  T  N  E  T  P  Q  P  T  A  I  K  N  Q  A  T  A  A  K  M  Q  D  Q  T  V  P  Q  E  G  142
```
AAATTCTCAAGTAGATAATAAAACAACGAATGATGCTAATAGCATAGCAACAAACAGTGAGCTTAAAAATTCTCAAACATTAGATTTACC
```
  N  S  Q  V  D  N  K  T  T  N  D  A  N  S  I  A  T  N  S  E  L  K  N  S  Q  T  L  D  L  P  172
```
ACAATCATCACCACAAACGATTTCCAATGCGCAAGGAACTAGTAAACCAAGTGTTAGAACGAGAGCTGTACGTAGTTTAGCTGTTGCTGA
```
  Q  S  S  P  Q  T  I  S  N  A  Q  G  T  S  K  P  S  V  R  T  R  A  V  R  S  L  A  V  A  E  202
```
ACCGGTAGTAAATGCTGCTGATGCTAAAGGTACAAATGTAAATGATAAAGTTACGGCAAGTAATTTCAAGTTAGAAAAGACTACATTTGA
```
  P  V  V  N  A  A  D  A  K  G  T  N  V  N  D  K  V  T  A  S  N  F  K  L  E  K  T  T  F  D  232
```
CCCTAATCAAAGTGGTAACACATTTATGGCGGCAAATTTTACAGTGACAGATAAAGTGAAATCAGGGGATTATTTTACAGCGAAGTTACC
```
  P  N  Q  S  G  N  T  F  M  A  A  N  F  T  V  T  D  K  V  K  S  G  D  Y  F  T  A  K  L  P  262
```
AGATAGTTTAACTGGTAATGGAGACGTGGATTATTCTAATTCAAATAATACGATGCCAATTGCAGACATTAAAAGTACGAATGGCGATGT
```
  D  S  L  T  G  N  G  D  V  D  Y  S  N  S  N  N  T  M  P  I  A  D  I  K  S  T  N  G  D  V  292
```
TGTAGCTAAAGCAACATATGATATCTTGACTAAGACGTATACATTTGTCTTTACAGATTATGTAAATAATAAAGAAAATATTAACG

*FIG. 5A*

```
                                                GACA
      V  A  K  A  T  Y  D  I  L  T  K  T  Y  T  F  V  F  T  D  Y  V  N  N  K  E  N  I  N
G  Q  322
ATTTTCATTACCTTTATTTACAGACCGAGCAAAGGCACCTAAATCAGGAACATATGATGCGAATATTAATATTGCCGATGAAATGT
TTAA
      P  S  L  P  L  F  T  D  R  A  K  A  P  K  S  G  T  Y  D  A  N  I  N  I  A  D  E  M
F  N  352
TAATAAAATTACTTATAACTATAGTTCGCCAATTGCAGGAATTGATAAACCAAATGGCGCGAACATTTCTTCTCAAATTATTGCTG
TAGA
      N  K  I  T  Y  N  Y  S  S  P  I  A  G  I  D  K  P  N  G  A  N  I  S  S  Q  I  I  G
V  D  382
TACAGCTTCAGGTCAAAACACATACCAGCAAACAGTATTTGTTAACCCTAAGCAACGAGTTTTAGGTAATACCTGGCTGTATATTA
AAGG
      T  A  S  G  Q  N  T  Y  K  Q  T  V  F  V  N  P  K  Q  R  V  L  G  N  T  W  V  Y  I
K  G  412
CTACCAAGATAAAATCGAAGAAAGTTGCGGTAAAGTAAGTGCTACAGATACAAAACTGAGAATTTTTGAAGTGAATGATACATCTA
AATT
      Y  Q  D  K  I  E  E  S  S  G  K  V  S  A  T  D  T  K  L  R  I  F  E  V  N  D  T  S
K  L  442
ATCAGATAGCTACTATGCAGATCCAAATGACTCTAACCTTAAAGAAGTAACAGACCAATTTAAAAATAGAATCTATTATGAGCATC
CAAA
      S  D  S  Y  Y  A  D  P  N  D  S  N  L  K  E  V  T  D  Q  F  K  N  R  I  Y  Y  E  H
P  N  472
TGTAGCTAGTATTAAATTTGGTGATATTACTAAAACATATGTAGTATTAGTAGAAGGGCATTACGACAATACAGGTAAGAACTTAA
AAAC
      V  A  S  I  K  F  G  D  I  T  K  T  Y  V  V  L  V  E  G  H  Y  D  N  T  G  K  N  L
K  T  502
TCAGGTTATTCAAGAAAATGTTGATCCTGTAACAAATAGAGACTACAGTATTTTCGGTTGGAATAATGAGAATGTTGTACGTTATG
GTGG
      Q  V  I  Q  E  N  V  D  P  V  T  N  R  D  Y  S  I  F  G  W  N  N  E  N  V  V  R  Y
G  G  532
                                                P>
TGGAAGTGCTGATGGTGATTCAGCAGTAAATCCGAAAGACCCAACTCCAGGGCCGCCGGTTGACCCAGAACCAAGTCCAGACCCAG
AACC
      G  S  A  D  G  D  S  A  V  N  P  K  D  P  T  P  G  P  P  V  D  P  E  P  S  P  D  P
E  P  562
                                                                            R>
AGAACCAACGCCAGATCCAGAACCAAGTCCAGACCCAGAACCGGAACCAAGCCCAGACCCGGATCCGGATTCGGATTCAGACAGTG
ACTC
      E  P  T  P  D  P  E  P  S  P  D  P  E  P  E  P  S  P  D  P  D  P  D  S  D  S  D  S
D  S  592
AGGCTCAGACAGCGACTCAGGTTCAGATAGCGACTCAGAATCAGATAGCGATTCGGATTCAGACAGTGATTCAGATTCAGACAGCG
ACTC
```

FIG. 5B

```
    G  S  D  S  D  S  G  S  D  S  D  S  E  S  D  S  D  S  D  S  D  S  D  S  D  S
D  S  622
AGAATCAGATAGCGATTCAGAATCAGATAGCGACTCAGATTCAGATAGCGATTCAGATTCAGATAGCGATTCAGATTCAGATAGCG
ATTC
    E  S  D  S  D  S  E  S  D  S  D  S  D  S  D  S  D  S  D  S  D  S  D  S  D  S
D  S  652
GGATTCAGACAGTGATTCAGATTCAGACAGCGACTCAGAATCAGATAGCCACTCAGAATCAGATAGTGAGTCAGATTCAGACAGTG
ACTC
    D  S  D  S  D  S  D  S  D  S  D  S  E  S  D  S  D  S  E  S  D  S  E  S  D  S
D  S  682
GGACTCAGACAGTGATTCAGACTCAGATAGCGATTCAGACTCAGATAGCGATTCAGATTCAGACAGCGACTCAGATTCAGACAGCG
ACTC
    D  S  D  S  D  S  D  S  D  S  D  S  D  S  D  S  D  S  D  S  D  S  D  S  D  S
D  S  712
AGACTCAGATAGCGACTCAGACTCAGACAGCGACTCAGATTCAGATAGCGATTCAGACTCAGACAGCGACTCAGACTCAGACAGCG
ACTC
    D  S  D  S  D  S  D  S·D  S  D  S  D  S  D  S  D  S  D  S  D  S  D  S  D  S
D  S  742
AGACTCAGATAGCGACTCAGATTCAGATAGCGATTCAGACTCAGACAGCGACTCAGATTCAGATAGCGATTCGGACTCAGACAGCG
ATTC
    D  S  D  S  D  S  D  S  D  S  D  S  D  S  D  S  D  S  D  S  D  S  D  S  D  S
D  S  772
AGATTCAGACAGCGACTCAGACTCGGATAGCGATTCAGATTCAGATAGCGATTCGGATTCAGACAGTGATTCAGATTCAGACAGCG
ACTC
    D  S  D  S  D  S  D  S  D  S  D  S  D  S  D  S  D  S  D  S  D  S  D  S  D  S
D  S  802
AGACTCGGATAGCGACTCAGACTCAGACAGCGATTCAGACTCAGATAGCGACTCAGACTCGGATAGCGACTCGGATTCAGATAGCG
ACTC
    D  S  D  S  D  S  D  S  D  S  D  S  D  S  D  S  D  S  D  S  D  S  D  S  D  S
D  S  832
                                                              W>
AGACTCAGATAGTGACTCCGATTCAAGAGTTACACCACCAAATAATGAACAGAAAGCACCATCAAATCCTAAAGGTGAAGTAAACC
ATTC
    D  S  D  S  D  S  D  S  R  V  T  P  P  N  N  E  Q  K  A  P  S  N  P  K  G  E  V  N
H  S  862
                                                              M>
TAATAAGGTATCAAAACAACACAAAACTCATGCTTTACCAGAAACAGGAGATAAGAGCGAAAACACAAATGCAACTTTATTTGGTC
CAAT
    N  K  V  S  K  Q  H  K  T  D  A  L  P  E  T  G  D  K  S  E  N  T  N  A  T  L  F  G
A  M  892
GATGGCATTATTAGCCATCATTACTATTGTTTAGAAAACGCAAGCAAGATCATAAAGAAAAAGCGTAAATACTTTTTTAGGCCGAAT
ACAT
    M  A  L  L  G  S  L  L  L  F  R  K  R  K  Q  D  H  K  E  K  A
```

*FIG. 5C*

913
TTGTATTCGGTTTTTTTGTTCAAAATGATTTTAAAGTGAATTGATTAAGCGTAAAATGTTGATAAAGTAGAATTAGAAAGGGGTCA
TGAC

GTATGGCTTATATTTCATTAAACTATCATTCACCAACAATTGGTATGCATCAAAATTTGACAGTCATTTTACCGGAACAACGAGAA
TTC

*FIG. 5D*

```
clfB   DVDYSNSNNTMPIADIKSTNGDVVAKATYDILTKTYTFVFTDYVNNKENINGQFSLPLFT 329
clfA   -VTSTAKVPPIMAGDQVLANGVIDSDG-------NVIYTFTDYVNTKDDVKATLTMPAYI 339
         *  .  .  *  .**  .  .       . . *****.*. .   .*  .
```

FIG. 6

S>
ATGAATAATAAAAAGACAGCAACAAATAGAAAAGGCATGATACCAAATCGATTAAACAAATTTTCGATAAGAAAGTATTCTCTAGGTACT

```
  M  N  N  K  K  T  A  T  N  R  K  G  M  I  P  N  R  L  N  K  F  S  I  R  K  Y  S  V  G
  T  30
```

A>
GCTTCAATTTTAGTAGGGACAACATTGATTTTTCGGTTAAGTGGTCATGAAGCTAAAGCGGCAGAACATACGAATGGAGAATTAAATCAA

```
  A  S  I  L  V  G  T  T  L  I  F  G  L  S  G  H  E  A  K  A  A  E  H  T  N  G  E  L  N
  Q  60
```

TCAAAAAATGAAACGACAGCCCCAAGTCAGAATAAAACAACTAAAAAAGTTGATAGTCCTCAACTAAAACACAATACGCAAACTCCAACT

```
  S  K  N  E  T  T  A  P  S  E  N  K  T  T  K  K  V  D  S  R  Q  L  K  D  N  T  Q  T  A
  T  90
```

GCAGATCAGCCTAAAGTGACAATGAGTGATAGTGCAACAGTTAAAGAAACTAGTAGTAACATGCAATCACCACAAAACGCTACAGCTAAT

```
  A  D  Q  P  K  V  T  M  S  D  S  A  T  V  K  E  T  S  S  N  M  Q  S  P  Q  N  A  T  A
  N  120
```

CAATCTACTACAAAAAGTAGCAATGTTACAACAAATGATAAATCATCAACTACATATAGTAATGAAACTGATAAAAGTAATTTAACACAA

```
  Q  S  T  T  K  T  S  N  V  T  T  N  D  K  S  S  T  T  Y  S  N  E  T  D  K  S  N  L  T
  Q  150
```

GCAAAAGATGTTTCAACTACACCTAAAACAACGACTATTAAACCAAGAACTTTAAATCGCATGGCAGTGAATACTGTTGCAGCTCCACAA

```
  A  K  D  V  S  T  T  P  K  T  T  T  I  K  P  R  T  L  N  R  M  A  V  N  T  V  A  A  P
  Q  180
```

CAAGGAACAAATGTTAATGATAAAGTACATTTTTCAAATATTGACATTGCGATTGATAAAGGACATGTTAATCAGACTACTGGTAAAACT

```
  Q  G  T  N  V  N  D  K  V  H  F  S  N  I  D  I  A  I  D  K  G  H  V  N  Q  T  T  G  K
  T  210
```

GAATTTTGGGCAACTTCAAGTGATGTTTTAAAATTAAAAGCAAATTACACAATCGATGATTCTGTTAAAGAGGGCGATACATTTACTTTT

```
  E  F  W  A  T  S  S  D  V  L  K  L  K  A  N  Y  T  I  D  D  S  V  K  E  G  D  T  F  T
  F  240
```

AAATATGGTCAATATTTCCGTCCAGGATCAGTAAGATTACCTTCACAAACTCAAAATTTATATAATGCCCAAGGTAATATTATTGCAAAA

```
  K  Y  G  Q  Y  F  R  P  G  S  V  R  L  P  S  Q  T  Q  N  L  Y  N  A  Q  G  N  I  I  A
  K  270
```

GGTATTTATGATAGTACAACAAACACAACAACATATACTTTTACGAACTATGTAGATCAATATACAAATGTTAGAGGTAGCTTTGAACAA

```
  G  I  Y  D  S  T  T  N  T  T  T̲ ̲Y̲ ̲T̲ ̲F̲ ̲T̲ ̲N̲ ̲Y̲ ̲V̲ ̲D̲  Q  Y  T  N  V  R  G  S  F  E
  Q  300
```

GTTGCATTTGCGAAACGTAAAAATGCAACAACTGATAAAACAGCTTATAAAATGGAAGTAACTTTAGGTAATGATACATATAGCGA

FIG. 7A

```
                                                                        AGAA
      V  A  F  A  K  R  K  N  A  T  T  D  K  T  A  Y  K  M  E  V  T  L  G  N  D  T  Y  S  E
 E    330
ATCATTGTCGATTATGGTAATAAAAAAGCACAACCGCTTATTTCAAGTACAAACTATATTAACAATCAAGATTTATCGCGTAATAT
GACT
      I  I  V  D  Y  G  N  K  K  A  Q  P  L  I  S  S  T  N  Y  I  N  N  E  D  L  S  R  N  M
 T    360
GCATATGTAAATCAACCTAAAAATACATATACTAAACAAACGTTTGTTACTAATTTAACTGGATATAAATTTAATCCAAATGCAAA
AAAC
      A  Y  V  N  Q  P  K  N  T  Y  T  K  Q  T  F  V  T  N  L  T  G  Y  K  F  N  P  N  A  K
 N    390
TTCAAAAATTTACGAACTGACAGATCAAAATCAATTTGTGGATAGTTTCACCCCTGATACTTCAAAACTTAAAGATGTTACTGATCA
ATTC
      F  K  I  Y  E  V  T  D  Q  N  Q  F  V  D  S  F  T  P  D  T  S  K  L  K  D  V  T  D  Q
 F    420
GATGTTATTTATAGTAATGATAATAAAACAGCTACAGTCGATTTAATGAAAGGCCAAACAAGCAGCAATAAACAATACATCATTCA
ACAA
      D  V  I  Y  S  N  D  N  K  T  A  T  V  D  L  M  K  G  Q  T  S  S  N  K  Q  Y  I  I  Q
 Q    450
GTTGCTTATCCAGATAATAGTTCAACAGATAATGGAAAAATTGATTATACTTTAGACACTGACAAAACTAAATATAGTTGGTCAAA
TAGT
      V  A  Y  P  D  N  S  S  T  D  N  G  K  I  D  Y  T  L  D  T  D  K  T  K  Y  S  W  S  N
 S    480
                                                                      B1>
TATTCAAATGTGAATGGCTCATCAACTGCTAATGGCGACCAAAAGAAATATAATCTAGGTGACTATGTATGGGAAGATACAAATAA
AGAT
      Y  S  N  V  N  G  S  S  T  A  N  G  D  Q  K  K  Y  N  L  G  D  Y  V  W  E  D  T  N  K
 D    510
GGTAAACAAGATGCCAATGAAAAAGGGATTAAAGGTGTTTATGTCATTCTTAAAGATAGTAACGGCTAAAGAATTAGATCGTACGAC
AACA
      G  K  Q  D  A  N  E  K  G  I  K  G  V  Y  V  I  L  K  D  S  N  G  K  E  L  D  R  T  T
 T    540
GATGAAAATGGTAAATATCAGTTCACTGGTTTAAGCAATGGAACTTATAGTGTAGAGTTTTCAACACCAGCCGGTTATACACCGAC
AACT
      D  E  N  G  K  Y  Q  F  T  G  L  S  N  G  T  Y  S  V  E  F  S  T  P  A  G  Y  T  P  T
 T    570
GCAAATGTAGGTACAGATGATGCTGTAGATTCTGATGGACTAACTACAACAGGTGTCATTAAAGACGCTGACAACATGACATTAGA
TAGT
      A  N  V  G  T  D  D  A  V  D  S  D  G  L  T  T  T  G  V  I  K  D  A  D  N  M  T  L  D
 S    600
                     B2>
GGATTCTACAAAACACCAAAATATAGTTTAGGTGATTATGTTTGGTACGACAGTAATAAAGATGCTAAACGAGATTCGACTGAAAA
AGGA
```

*FIG. 7B*

```
        G  F  Y  K  T  P  K  Y  S  L  G  D  Y  V  W  Y  D  S  N  K  D  G  K  R  D  S  T  E  K
G    630
ATTAAAGGTGTTAAAGTTACTTTGCAAAACGAAAAAGGCGAAGTAATTGGTACAACTGAAACAGATGAAAATGGTAAATACCGCTT
TGAT
        I  K  G  V  K  V  T  L  Q  N  E  K  G  E  V  I  G  T  T  E  T  D  E  N  G  K  Y  R  F
D    660
AATTTAGATAGTGGTAAATACAAAGTTATCTTTGAAAAACCTGCTGGCTTAACTCAAACAGGTACAAATACAACTGAAGATGATAA
AGAT
        N  L  D  S  G  K  Y  K  V  I  F  E  K  P  A  G  L  T  Q  T  G  T  N  T  T  E  D  D  K
D    690
                                                                                        R>
GCCGATGGTGGCGAAGTTGATGTAACAATTACGGATCATGATGATTTCACACTTGATAATGGCTACTACGAACAACAAACATCAGA
TAGC
        A  D  G  G  E  V  D  V  T  I  T  D  H  D  D  F  T  L  D  N  G  Y  Y  E  E  E  T  S  D
S    720
GACTCAGATTCTGACAGCGATTCAGACTCAGATAGCGACTCAGATTCAGATAGCGACTCAGATTCAGACAGCGATTCAGACAGCGA
CTCA
        D  S  D  S  D  S  D  S  D  S  D  S  D  S  D  S  D  S  D  S  D  S  D  S  D  S  D  S  D
S    750
GACTCAGATAGCGATTCAGATTCAGACAGCGACTCAGACTCAGACAGCAATTCAGACTCGGATAGCGACTCAGACTCAGATAGCGA
CTCA
        D  S  D  S  D  S  D  S  D  S  D  S  D  S  N  S  D  S  D  S  D  S  D  S  D  S  D  S  D
S    780
GATTCGGATAGCGACTCAGACTCAGATAGCGATTCAGATTCAGATAGCGATTCGGACTCAGACAGTGATTCAGATTCAGACTCAGA
TAGC
        D  S  D  S  D  S  D  S  D  S  D  S  D  S  D  S  D  S  D  S  D  S  D  S  D  S  D  S  D
S    810
GACTCAGATTCTGACAGCGATTCAGACTCAGACATCGACTCAGACTCAGACAGTGATTCAGATTCAGACAGCGACTCAGATTCAGA
TAGC
        D  S  D  S  D  S  D  S  D  S  D  S  D  S  D  S  D  S  D  S  D  S  D  S  D  S  D  S  D
S    840
GACTCAGACTCAGATAGCGACTCAGACTCAGATAGCGACTCAGACTCGGATAGCGATTCAGATTCAGACAGCGACTCAGATTCAGA
TAGC
        D  S  D  S  D  S  D  S  D  S  D  S  D  S  D  S  D  S  D  S  D  S  D  S  D  S  D  S  D
S    870
                                                                                W>
GATTCGGACTCAGACAACGACTCAGATTCAGATAGCGATTCAGATTCAGATGCAGGTAAACATACTCCGGCTAAACCAATGAGTAC
GGTT
        D  S  D  S  D  N  D  S  D  S  D  S  D  S  D  A  G  K  H  T  P  A  K  P  M  S  T
V    900
                                                                        M>
AAAGATCAGCATAAAACAGCTAAAGCATTACCAGAAACACGTAGTGAAAATAATAATTCAAATAATCGCACATTATTCGGTGGATT
ATTC
```

*FIG. 7C*

```
K  D  Q  H  K  T  A  K  A  L  P  E  T  G  S  E  N  N  N  S  N  N  G  T  L  F  G  G  L
F    930
GCGGCATTAGGATCATTATTGTCATTCGGTCCTCGTAAAAAACAAAATAAA
  A  A  L  G  S  L  L  S  F  G  R  R  K  K  Q  N  K
947
```

FIG. 7D

S>
ATGCTAAACAGAGAAAATAAAACGGCAATAACAAGGAAAGCCATGGTATCCAATCGATTAAATAAATTTTCGATTAGAAAGTACACAGTG

```
  M  L  N  R  E  N  K  T  A  I  T  R  K  G  M  V  S  N  R  L  N  K  F  S  I  R  K  Y  T
V  30
```

A>
GGAACAGCATCAATTTTAGTAGCTACAACATTAATTTTTGCTCTGGGGAACCAAGAAGCAAAGGCTGCAGAAAGTACTAATAAAGAATTG

```
  G  T  A  S  I  L  V  G  T  T  L  I  F  G  L  G  N  Q  E  A  K  A  A  E  S  T  N  K  E
L  60
```

AACGAAGCGACAACTTCAGCAAGTGATAATCAATCGAGTGATAAAGTTGATATGCAGCAACTAAATCAAGAAGACAATACTAAAAATGAT

```
  N  E  A  T  T  S  A  S  D  N  Q  S  S  D  K  V  D  M  Q  Q  L  N  Q  E  D  N  T  K  N
D  90
```

AATCAAAAAGAAATGGTATCATCTCAAGGTAATGAAACGACTTCAAATGGGAATAAATTAATAGAAAAAGAAAGTGTACAATCTAGCACT

```
  N  Q  K  E  M  V  S  S  Q  G  N  E  T  T  S  N  G  N  K  L  I  E  K  E  S  V  Q  S  T
T  120
```

GGAAATAAAGTTGAAGTTTCAACTGCCAAAATCAGATGAGCAAGCTTCACCAAAATCTACGAATGAAGATTTAAACACTAAACAAACTATA

```
  G  N  K  V  E  V  S  T  A  K  S  D  E  Q  A  S  P  K  S  T  N  E  D  L  N  T  K  Q  T
I  150
```

AGTAATCAAGAAGCGTTACAACCTGATTTGCAAGAGAATAAATCAGTGGTAAATGTTCAACCAACTAATGAGGAAAACAAAAAGGTAGAT

```
  S  N  Q  E  A  L  Q  P  D  L  Q  E  N  K  S  V  V  N  V  Q  P  T  N  E  E  N  K  K  V
D  180
```

GCCAAAACTGAATCAACTACATTAAATGTTAAAAGTGATGCTATCAAGAGTAATGATGAAACTCTTGTTGATAACAATAGTAATTCAAAT

```
  A  K  T  E  S  T  T  L  N  V  K  S  D  A  I  K  S  N  D  E  T  L  V  D  N  N  S  N  S
N  210
```

AATGAAAATAATGCAGATATCATTTTGCCAAAAAGTACAGCACCTAAACGTTTGAATACAAGAATGCGTATAGCAGCAGTACAGCCATCA

```
  N  E  N  N  A  D  I  I  L  P  K  S  T  A  P  K  R  L  N  T  R  M  R  I  A  A  V  Q  P
S  240
```

TCAACAGAGGCTAAAAATGTTAATGATTTAATCACATCAAATACAACATTAACTGTCGTTGATGCAGATAAAAACAATAAAATCGTACCA

```
  S  T  E  A  K  N  V  N  D  L  I  T  S  N  T  T  L  T  V  V  D  A  D  K  N  N  K  I  V
P  270
```

GCCCAAGATTATTTATCATTAAAATCACAAATTACAGTTGATGACAAAGTTAAATCAGGTGATTATTTCACAATTAAATACTCAGATACA

```
  A  Q  D  Y  L  S  L  K  S  Q  I  T  V  D  D  K  V  K  S  G  D  Y  F  T  I  K  Y  S  D
T  300
```

GTACAAGTATATGGATTGAATCCGGAAGATATTAAAAATATTGGTGATATTAAAGATCCAAATAATGGTGAAACAATTGCGACTGC

*FIG. 8A*

```
AAAA
 V  Q  V  Y  G  L  N  P  E  D  I  K  N  I  G  D  I  K  D  P  N  N  G  E  T  I  A  T  A
 K   330
CATGATACTGCAAATAATTTAATTACATATACATTTACAGATTATGTTGATCGATTTAATTCTGTACAAATGGGAATTAATTATTC
AATT
 H  D  T  A  N  N  L  I  T  Y  T  F  T  D  Y  V  D  R  F  N  S  V  Q  M  G  I  N  Y  S
 I   360
TATATGCATGCTGATACAATTCCTGTTAGTAAAAACGATGTTGAGTTTAATGTTACCATAGGTAATACTACAACAAAAACAACTGC
TAAC
 Y  M  D  A  D  T  I  P  V  S  K  N  D  V  E  F  N  V  T  I  G  N  T  T  T  K  T  T  A
 N   390
ATTCAATATCCAGATTATGTTGTAAATGAGAAAAATTCAATTGGATCAGCGTTCACTGAAACAGTTTCACATGTTGGAAATAAAGA
AAAT
 I  Q  Y  P  D  Y  V  V  N  E  K  N  S  I  G  S  A  F  T  E  T  V  S  H  V  G  N  K  E
 N   420
CCAGGCTACTATAAACAAACGATTTATGTAAATCCATCGGAAAATTCTTTAACAAATGCCAAACTAAAAGTTCAAGCTTACCACTC
AAGT
 P  G  Y  Y  K  Q  T  I  Y  V  N  P  S  E  N  S  L  T  N  A  K  L  K  V  Q  A  Y  H  S
 S   450
TATCCTAATAATATCGGGCAAATAAATAAAGATGTAACAGATATAAAAATATATCAAGTTCCTAAAGGTTATACATTAAATAAAGG
ATAC
 Y  P  N  N  I  G  Q  I  N  K  D  V  T  D  I  K  I  Y  Q  V  P  K  G  Y  T  L  N  K  G
 Y   480
GATGTGAATACTAAAGAGCTTACAGATGTAACAAATCAATACTTGCAGAAAATTACATATGGCGACAACAATAGCGCTGTTATTGA
TTTT
 D  V  N  T  K  E  L  T  D  V  T  N  Q  Y  L  Q  K  I  T  Y  G  D  N  N  S  A  V  I  D
 F   510
GGAAATGCAGATTCTGCTTATGTTGTAATGGTTAATACAAAATTCCAATATACAAATAGCGAAAGCCCAACACTTGTTCAAATGGC
TACT
 G  N  A  D  S  A  Y  V  V  M  V  N  T  K  F  Q  Y  T  N  S  E  S  P  T  L  V  Q  M  A
 T   540
                                                                                    B1>
TTATCTTCAACAGGTAATAAATCCGTTTCTACTGGCAATGCTTTAGGATTTACTAATAACCAAAGTGGCGGAGCTGGTCAAGAAGT
ATAT
 L  S  S  T  G  N  K  S  V  S  T  G  N  A  L  G  F  T  N  N  Q  S  G  G  A  G  Q  E  V
 Y   570
AAAATTGGTAACTACGTATGGGAAGATACTAATAAAAACGGTGTTCAAGAATTAGGAGAAAAAGGCGTTGGCAATGTAACTGTAAC
TGTA
 K  I  G  N  Y  V  W  E  D  T  N  K  N  G  V  Q  E  L  G  E  K  G  V  G  N  V  T  V  T
 V   600
TTTGATAATAATACAAATACAAAAGTAGGAGAAGCAGTTACTAAAGAAGATGGGTCATACTTGATTCCAAACTTACCTAATGGAGA
TTAC
 F  D  N  N  T  N  T  K  V  G  E  A  V  T  K  E  D  G  S  Y  L  I  P  N  L  P  N  G  D
```

*FIG. 8B*

```
                Y    630
CGTGTAGAATTTTCAAACTTACCAAAAGGTTATGAAGTAACCCCTTCAAAACAAGGTAATAACGAAGAATTAGATTCAAACGGCTT
ATCT
      R  V  E  F  S  N  L  P  K  G  Y  E  V  T  P  S  K  Q  G  N  N  E  E  L  D  S  N  G  L
S    660
                                                             B2>
TCAGTTATTACAGTTAATGGCAAAGATAACTTATCTGCAGACTTAGGTATTTACAAACCTAAATACAACTTAGGTGACTATGTCTG
GGAA
      S  V  I  T  V  N  G  K  D  N  L  S  A  D  L  G  I  Y  K  P  K  Y  N  L  G  D  Y  V  W
E    690
GATACAAATAAAAATGGTATCCAAGACCAAGATGAAAAAGGTATATCTGGCGTAACGGTAACATTAAAAGATGAAAACGGTAACGT
GTTA
      D  T  N  K  N  G  I  Q  D  Q  D  E  K  G  I  S  G  V  T  V  T  L  K  D  E  N  G  N  V
L    720
AAAAACAGTTACAACAGACGCTGATGGCAAATATAAATTTACTGATTTAGATAATGGTAATTATAAAGTTGAATTTACTACACCAGA
AGGC
      K  T  V  T  T  D  A  D  G  K  Y  K  F  T  D  L  D  N  G  N  Y  K  V  E  F  T  T  P  E
G    750
TATACACCGACTACAGTAACATCTGGTAGCGACATTGAAAAAGACTCTAATGGTTTAACAACAACAGGTGTTATTAATGGTGCTGA
TAAC
      Y  T  P  T  T  V  T  S  G  S  D  I  E  K  D  S  N  G  L  T  T  T  G  V  I  N  G  A  D
N    780
                          B3>
ATGACATTAGATAGTGGATTCTACAAAACACCAAAATATAATTTAGGTAATTATGTATGGGAAGATACAAATAAAGATGGTAAGCA
GGAT
      M  T  L  D  S  G  F  Y  K  T  P  K  Y  N  L  G  N  Y  V  W  E  D  T  N  K  D  G  K  Q
D    810
TCAACTGAAAAAGGTATTTCAGGCGTAACAGTTACATTGAAAAATGAAAACGGTGAAGTTTTACAAACAACTAAAACAGATAAAGA
TGGT
      S  T  E  K  G  I  S  G  V  T  V  T  L  K  N  E  N  G  E  V  L  Q  T  T  K  T  D  K  D
G    840
AAATATCAATTTACTGGATTAGAAAATGGAACTTATAAAGTTGAATTCGAAACACCATCAGGTTACACACCAACACAAGTAGGTTC
AGGA
      K  Y  Q  F  T  G  L  E  N  G  T  Y  K  V  E  F  E  T  P  S  G  Y  T  P  T  Q  V  G  S
G    870
ACTGATGAAGGTATAGATTCAAATGGTACATCAACAACAGGTGTCATTAAAGATAAAGATAACGATACTATTGACTCTGGTTTCTA
CAAA
      T  D  E  G  I  D  S  N  G  T  S  T  T  G  V  I  K  D  K  D  N  D  T  I  D  S  G  F  Y
K    900
     B4>
CCGACTTACAACTTAGGTGACTATGTATGGGAAGATACAAATAAAAACGGTGTTCAAGATAAAGATGAAAAGGGCATTTCAGGTGT
AACA
      P  T  Y  N  L  G  D  Y  V  W  E  D  T  N  K  N  G  V  Q  D  K  D  E  K  G  I  S  G  V
```

*FIG. 8C*

```
                                                                    T   930
GTTACGTTAAAAGATGAAAACGACAAAGTTTTAAAAACAGTTACAACAGATGAAAATGGTAAATATCAATTCACTGATTTAAACAA
TGGA
 V  T  L  K  D  E  N  D  K  V  L  K  T  V  T  T  D  E  N  G  K  Y  Q  F  T  D  L  N  N
G   960
ACTTATAAAGTTGAATTCGAGACACCATCAGGTTATACACCAACTTCAGTAACTTCTGGAAATGATACTGAAAAAGATTCTAATGG
TTTA
 T  Y  K  V  E  F  E  T  P  S  G  Y  T  P  T  S  V  T  S  G  N  D  T  E  K  D  S  N  G
L   990
                                                                                    B5>
ACAACAACAGCTCTCATTAAAGATGCAGATAACATGACATTAGACAGTGGTTTCTATAAAACACCAAAATATAGTTTAGGTGATTA
TGTT
 T  T  T  C  V  I  K  D  A  D  N  M  T  L  D  S  G  F  Y  K  T  P  K  Y  S  L  G  D  Y
V   1020
TGGTACGACAGTAATAAAGACGGCAAACAAGATTCAACTGAAAAAGGTATCAAAGATGTTAAAGTTACTTTATTAAATGAAAAAGG
CGAA
 W  Y  D  S  N  K  D  G  K  Q  D  S  T  E  K  G  I  K  D  V  K  V  T  L  L  N  E  K  G
E   1050
GTAATTGGAACAACTAAAACAGATGAAAATGGTAAATACTGCTTTGATAATTTAGATAGCGGTAAATACAAAGTTATTTTTGAAAA
GCCT
 V  I  G  T  T  K  T  D  E  N  G  K  Y  C  F  D  N  L  D  S  G  K  Y  K  V  I  F  E  K
P   1080
GCTGGCTTAACACAAACAGGTACAAATACAACTGAAGATGATAAACATGCAGATGGTGGCGAAGTTGACGTAACAATTACGGATCA
TGAT
 A  G  L  T  Q  T  G  T  N  T  T  E  D  D  K  D  A  D  G  G  E  V  D  V  T  I  T  D  H
D   1110
R>
GATTTCACACTTGATAATGGCTACTACGAAGAAGAAACATCAGATAGCGACTCAGATTCGGACAGCGACTCAGATTCAGACAGAGA
CTCA
 D  F  T  L  D  N  G  Y  Y  E  E  E  T  S  D  S  D  S  D  S  D  S  D  S  D  R  D
S   1140
GACTCAGATAGTGATTCAGACTCGGATAGCGATTCAGATTCAGACAGCGATTCAGATTCAGATAGCGATTCAGATTCAGACAGAGA
CTCA
 D  S  D  S  D  S  D  S  D  S  D  S  D  S  D  S  D  S  D  S  D  S  D  S  D  R  D
S   1170
GATAGTGATTCAGACTCAGATAGCGACTCAGATTCAGACAGCGACTCAGATTCAGACAGCGACTCAGACTCAGATAGTGATTCAGA
CTCA
 D  S  D  S  D  S  D  S  D  S  D  S  D  S  D  S  D  S  D  S  D  S  D  S  D  S  D  S  D
S   1200
GATAGCGACTCAGATTCGGATAGCGACTCAGATTCAGACAGCGACTCAGACTCGGATAGTGATTCAGACTCAGATAGCGACTCAGA
CTCA
 D  S  D  S  D  S  D  S  D  S  D  S  D  S  D  S  D  S  D  S  D  S  D  S  D  S  D  S  D
S   1230
```

*FIG. 8D*

```
                                                                     W>
GATAGCGATTCAGATTCAGATAGCGACTCAGACTCAGACAGCGATTCAGACTCAGACAGCGACTCAGACTCAGATGCAGGTAAGCA
CACA
 D  S  D  S  D  S  D  S  D  S  D  S  D  S  D  S  D  S  D  S  D  A  G  K  H
T  1260
CCTGTTAAACCAATGAGTACTACTAAAGACCATCACAATAAAGCAAAAGCATTACCAGAAACAGGTAATGAAAATAGCGGCTCAAA
TAAC
  P  V  K  P  M  S  T  T  K  D  H  H  N  K  A  K  A  L  P  E  T  G  N  E  S  G  S
N  1290
M>
GCAACGTTATTTGGCGGATTATTCGCAGCATTAGGATCATTATTGTTATTCGGTCGTCGTAAAAAACAAAATAAA
  A  T  L  F  G  G  L  F  A  A  L  G  S  L  L  L  F  G  R  R  K  K  Q  N  K
1315
```

*FIG. 8E*

S>
ATGATTAACAGGGATAATAAAAAGGCAATAACAAAAAAGGGTATGATTTCAAATCGCTTAAACAAATTTTCGATTAGAAAGTATAC
TGTA
  M  I  N  R  D  N  K  K  A  I  T  K  K  G  M  I  S  N  R  L  N  K  F  S  I  R  K  Y  T
V    30

A>
GGAACTGCATCGATTTTAGTAGCTACGACATTGATTTTTGGTCTAGGGAACCAAGAAGCCTAAAGCTCCTGAAAACACTAGTACAGA
AAAT
  G  T  A  S  I  L  V  G  T  T  L  I  F  G  L  G  N  Q  E  A  K  A  A  E  N  T  S  T  E
N    60
GCAAAACAAGATGATGCAACGACTAGTGATAATAAAGAAGTAGTGTCGGAAACTGAAAATAATTCGACAACAGAAAATAATTCAAC
AAAT
  A  K  Q  D  D  A  T  T  S  D  N  K  E  V  V  S  E  T  E  N  N  S  T  T  E  N  N  S  T
N    90
CCAATTAAGAAAGAAACAAATACTGATTCACAACCAGAAGCTAAAAAAGAATCAACTTCATCAAGTACTCAAAAACAGCAAAATAA
CGTT
  P  I  K  K  E  T  N  T  D  S  Q  P  E  A  K  K  E  S  T  S  S  S  T  Q  K  Q  Q  N  N
V    120
ACAGCTACAACTGAAACTAAGCCTCAAAACATTGAAAAAGAAAATGTTAAACCTTCAACTGATAAAACTGCGACAGAAGATACATC
TGTT
  T  A  T  T  E  T  K  P  Q  N  I  E  K  E  N  V  K  P  S  T  D  K  T  A  T  E  D  T  S
V    150
ATTTTAGAAGAGAAGAAAGCACCAAATAATACAAATAACGATGTAACTACAAAACCATCTACAAGTGAACCATCTACAAGTGAAAT
TCAA
  I  L  E  E  K  K  A  P  N  N  T  N  N  D  V  T  T  K  P  S  T  S  E  P  S  T  S  E  I
Q    180
ACAAAACCAACTACACCTCAAGAATCTACAAATATTGAAAATTCACAACCGCAACCAACGCCTTCAAAAGTAGACAATCAAGTTAC
AGAT
  T  K  P  T  T  P  Q  E  S  T  N  I  E  N  S  Q  P  Q  P  T  P  S  K  V  D  N  Q  V  T
D    210
GCAACTAATCCAAAAGAACCAGTAAATGTGTCAAAAGAAGAACTTAAAAATAATCCTGAGAAATTAAAAGAATTGGTTAGAAATGA
TAGC
  A  T  N  P  K  E  P  V  N  V  S  K  E  E  L  K  N  N  P  E  K  L  K  E  L  V  R  N  D
S    240
AATACAGATCATTCAACTAAACCAGTTGCTACAGCTCCAACAAGTGTTGCACCAAAAACGTGTAAACGCAAAAATGCGCTTTGCAGT
TGCA
  N  T  D  H  S  T  K  P  V  A  T  A  P  T  S  V  A  P  K  R  V  N  A  K  M  R  F  A  V
A    270
CAACCAGCAGCAGTTGCTTCAAACAATGTAAATGATTTAATTAAAGTGACGAAGCAAACAATCAAAGTTGGCGATGGTAAAGATAA
TGTG
  Q  P  A  A  V  A  S  N  N  V  N  D  L  I  K  V  T  K  Q  T  I  K  V  G  D  G  K  D  N
V    300
GCAGCAGCGCATGACGGTAAAGATATTGAATATGATACAGAGTTTACAATTGACAATAAAGTCaAAAAAGGCGATACAATGACGAT

*FIG. 9A*

```
                                                TAAT
      A  A  A  H  D  G  K  D  I  E  Y  D  T  E  F  T  I  D  N  K  V  K  K  G  D  T  M  T  I
N 330
TATGATAAGAATGTAATTCCTTCGGATTTAACAGATAAAAATGATCCTATCGATATTACTGATCCATCAGGAGAGGTCATTGCTAA
AGGA
      Y  D  K  N  V  I  P  S  D  L  T  D  K  N  D  P  I  D  I  T  D  P  S  G  E  V  I  A  K
G 360
ACATTTGATAAAGCAACTAAGCAAATCACATATACATTTACAGACTATGTAGATAAATATGAAGATATAAAATCACGCTTAACTCT
ATAT
      T  F  D  K  A  T  K  Q  I  T  Y  T  F  T  D  Y  V  D  K  Y  E  D  I  K  S  R  L  T  L
Y 390
TCGTATATTGATAAAAAAACAGTTCCAAATGAGACAAGTTTGAATTTAACATTTGCTACAGCAGGTAAAGAAACAAGCCAAAATGT
CACT
      S  Y  I  D  K  K  T  V  P  N  E  T  S  L  N  L  T  F  A  T  A  G  K  E  T  S  Q  N  V
T 420
GTTGATTATCAAGATCCAATGGTCCATGGTGATTCAAACATTCAATCTATCTTTACAAAATTAGATGAAGATAAGCAAACTATTGA
ACAA
      V  D  Y  Q  D  P  M  V  H  G  D  S  N  I  Q  S  I  F  T  K  L  D  E  D  K  Q  T  I  E
Q 450
CAAATTTATGTTAACCCATTGAAAAAATCAGCAACCAACACTAAAGTTGATATAGCTGGTAGTCAAGTAGATGATTATGGAAATAT
TAAA
      Q  I  Y  V  N  P  L  K  K  S  A  T  N  T  K  V  D  I  A  G  S  Q  V  D  D  Y  G  N  I
K 480
CTAGGAAATGGTAGCACCATTATTGACCAAAATACAGAAATAAAGGTTTATAAAGTTAACTCTGATCAACAATTGCCTCAAAGTAA
TAGA
      L  G  N  G  S  T  I  I  D  Q  N  T  E  I  K  V  Y  K  V  N  S  D  Q  Q  L  P  Q  S  N
R 510
ATCTATGATTTTAGTCAATACGAAGATGTAACAAGTCAATTTGATAATAAAAAATCATTTAGTAATAATGTAGCAACATTGGATTT
TGGT
      I  Y  D  F  S  Q  Y  E  D  V  T  S  Q  F  D  N  K  K  S  F  S  N  N  V  A  T  L  D  F
G 540
GATATTAATTCAGCCTATATTATCAAAGTTGTTAGTAAATATACACCTACATCAGATGGCGAACTAGATATTGCCCAAGGTACTAG
TATG
      D  I  N  S  A  Y  I  I  K  V  V  S  K  Y  T  P  T  S  D  G  E  L  D  I  A  Q  G  T  S
M 570
AGAACAACTGATAAATATGGTTATTATAATTATGCAGGATATTCAAACTTCATCGTAACTTCTAATGACACTGGCGGTGGCGACGG
TACT
      R  T  T  D  K  Y  G  Y  Y  N  Y  A  G  Y  S  N  F  I  V  T  S  N  D  T  G  G  D  G
T 600
                                    B1>
GTTAAACCTGAAGAAAAGTTATACAAAATTGGTGACTATGTATGGGAAGACGTTGATAAAGACGGTGTTCAAGGTACAGATTCAAA
AGAA
      V  K  P  E  E  K  L  Y  K  I  G  D  Y  V  W  E  D  V  D  K  D  G  V  Q  G  T  D  S  K
```

FIG. 9B

E    630
AAACCAATGGCAAACGTTTTAGTTACATTAACTTACCCGGACGGTACTACAAAATCAGTAAGAACAGATGCTAATGGTCATTATGAATTC
 K  P  M  A  N  V  L  V  T  L  T  Y  P  D  G  T  T  K  S  V  R  T  D  A  N  G  H  Y  E
F    660
GGTGGTTTGAAAGACGGAGAAACTTATACAGTTAAATTCGAAACGCCAACTGGATATCTTCCAACAAAAGTAAATGGAACAACTGATGGT
 G  G  L  K  D  G  E  T  Y  T  V  K  F  E  T  P  T  G  Y  L  P  T  K  V  N  G  T  T  D
G    690
B2>
GAAAAAGACTCAAATGGTAGTTCGGTTACTGTTAAAATTAATGGTAAAGATGATATGTCTTTAGATACTGGTTTTTACAAAGAACCTAAA
 E  K  D  S  N  G  S  S  V  T  V  K  I  N  G  K  D  D  M  S  L  D  T  G  F  Y  K  E  P
K    720
TACAACTTAGGTGACTATGTATGGGAAGATACTAATAAAGATGGTATCCAAGATGCAAATGAGCCAGGAATCAAAGATGTTAAGGTTACA
 Y  N  L  G  D  Y  V  W  E  D  T  N  K  D  G  I  Q  D  A  N  E  P  G  I  K  D  V  K  V
T    750
TTAAAAGATAGTACTGGAAAAGTTATTGGTACAACTACTACTGATGCCTCGGGTAAATATAAATTTACAGATTTAGATAATGGTAACTAT
 L  K  D  S  T  G  K  V  I  G  T  T  T  T  D  A  S  G  K  Y  K  F  T  D  L  D  N  G  N
Y    780
ACAGTAGAATTTGAAACACCAGCAGGTTACACGCCAACGGTTAAAAATACTACAGCTGATGATAAAGATTCTAATGGTTTAACAACAACA
 T  V  E  F  E  T  P  A  G  Y  T  P  T  V  K  N  T  T  A  D  D  K  D  S  N  G  L  T  T
T    810
                                                                              B3>
GGTGTCATTAAAGATGCAGATAATATGACATTAGACAGGGGTTTCTATAAAACACCAAAATACAGTTTAGGTGATTATGTTTGGTACGAC
 G  V  I  K  D  A  D  N  M  T  L  D  R  G  F  Y  K  T  P  K  Y  S  L  G  D  Y  V  W  Y
D    840
AGTAATAAAGACGGCAAACAAGATTCAACTGAAAAAGGTATCAAAGATGTGACAGTTACATTGCAAAACGAAAAAGGCGAAGTAATTGGA
 S  N  K  D  G  K  Q  D  S  T  E  K  G  I  K  D  V  T  V  T  L  Q  N  E  K  G  E  V  I
G    870
ACAACTAAAACAGATGAAAATGGTAAATATCGTTTCGATAATTTAGATAGCGGTAAATACAAAGTTATTTTTGAAAAGCCTGCTGGCTTA
 T  T  K  T  D  E  N  G  K  Y  R  F  D  N  L  D  S  G  K  Y  K  V  I  F  E  K  P  A  G
L    900
ACACAAACAGTTACAAATACAACTGAAGATGATAAAGATGCAGATGGTGGCGAAGTTGACGTAACAATTACGGATCATGATGATTTCACA
 T  Q  T  V  T  N  T  T  E  D  D  K  D  A  D  G  G  E  V  D  V  T  I  T  D  H  D  D  F
T    930

*FIG. 9C*

```
                                                  R>
CTTGATAACGGATACTTCGAAGAAGATACATCAGACAGCGATTCAGACTCAGATAGTGACTCAGACAGCGACTCAGACTCAGACAG
CGAC
  L  D  N  G  Y  F  E  E  D  T  S  D  S  D  S  D  S  D  S  D  S  D  S  D  S  D  S  D  S
D   960
TCAGACTCAGACAGTGATTCAGATTCAGACAGCGACTCAGATTCAGATAGCGACTCAGATTCGGACAGCGATTCAGACTCAGATAG
CGAC
  S  D  S  D  S  D  S  D  S  D  S  D  S  D  S  D  S  D  S  D  S  D  S  D  S  D  S  D  S
D   990
TCAGATTCAGATAGCGATTCAGACTCAGACAGCGACTCAGATTCAGATAGCGATTCGGACTCAGACAGCGATTCAGACTCAGATAG
CGAC
  S  D  S  D  S  D  S  D  S  D  S  D  S  D  S  D  S  D  S  D  S  D  S  D  S  D  S  D  S
D   1020
TCAGACTCAGACAGCGACTCAGATTCAGATAGCGATTCGGACTCAGATAGCGACTCAGATTCAGACAGCGATTCAGACTCAGATAG
CGAC
  S  D  S  D  S  D  S  D  S  D  S  D  S  D  S  D  S  D  S  D  S  D  S  D  S  D  S  D  S
D   1050
TCAGATTCAGACAGCGATTCAGACTCAGATAGCGACTCAGACTCAGACAGTGATTCAGATTCAGACAGCGACTCAGACTCAGATAG
CGAC
  S  D  S  D  S  D  S  D  S  D  S  D  S  D  S  D  S  D  S  D  S  D  S  D  S  D  S  D  S
D   1080
                                                                                    W>
TCAGATTCAGACAGCGACTCAGACTCAGATAGCGACTCAGACTCAGACAGTGATTCAGACAGCGATTCAGACTCGGATGCAGGAAA
ACAT
  S  D  S  D  S  D  S  D  S  D  S  D  S  D  S  D  S  D  S  D  S  D  S  D  S  D  A  G  K
H   1110
ACACCTGTTAAACCAATGAGTACTACTAAAGACCATCACAATAAAGCAAAAGCATTACCAGAAACAGGTAGTGAAAATAACGGCTC
AAAT
  T  P  V  K  P  M  S  T  T  K  D  H  H  N  K  A  K  A  L  P  E  T  G  S  E  N  N  G  S
N   1140
                                              M>
AACGCAACGTTATTTGGTGGATTATTTGCAGCATTAGGTTCATTATTGTTATTCGGTCGTCGCAAAAAACAAAACAAA
  N  A  T  L  F  G  G  L  F  A  A  L  G  S  L  L  L  F  G  R  R  K  K  Q  N  K
1166
```

*FIG. 9D*

| %    | ClfB | SdrC | SdrD | SdrE |
|------|------|------|------|------|
| ClfA | 27   | 20   | 24   | 25   |
| ClfB |      | 24   | 25   | 23   |
| SdrC |      |      | 24   | 23   |
| SdrD |      |      |      | 30   |

FIG. 11

1.
| | | |
|---|---|---|
| SdrD | TVDDKVKSGDYFTIK | 296 |
| SdrE | TIDNKVKKGDTMTIN | 330 |
| ClfB | TVTDKVKSGDYFTAK | 269 |
| SdrC | TIDDSVKEGDTFTFK | 241 |
| ClfA | SVPNSAVKGDTFKIT | 278 |
| | :: :.. .** :. . | |

2.
| | | |
|---|---|---|
| SdrD | ETIATAKHDTANNLITYTFTDYVD | 347 |
| SdrE | EVIAKGTFDKATKQITYTFTDYVD | 378 |
| ClfB | DVVAKATYDILTKTYTFVFTDYVN | 314 |
| SdrC | NIIAKGIYDSTTNTTTYTFTNYVD | 289 |
| ClfA | QVLANGVIDSDGN-VIYTFTDYVN | 324 |
| | : .*.. * : .:: | |

3.
| | | |
|---|---|---|
| SdrD | TDIKIYQVPK | 472 |
| SdrE | TEIKVYKVNS | 501 |
| ClfB | TKLRIFEVND | 438 |
| SdrC | --FKIYEVTD | 398 |
| ClfA | TSIKVYKVDN | 440 |
| | :::::* . | |

4.
| | | |
|---|---|---|
| SdrD | DVTNQ | 493 |
| SdrE | DVTSQ | 523 |
| ClfB | EVTDQ | 461 |
| SdrC | DVTDQ | 419 |
| ClfA | DVTNS | 461 |
| | :**.. | |

5.
| | |
|---|---|
| SdrCB1 | KYNLGDYVWEDTNKDGKQ--DANEKGIKGVYVILKDSNGK-ELDRTTTDENGKYQFTGLS |
| SdrCB2 | KYSLGDYVWYDSNKDGKR--DSTEKGIKGVKVTLQNEKGE-VIGTTETDENGKYRFDNLD |
| SdrDB1 | VYKIGNYVWEDTNKNGVQ--ELGEKGVGNVTVTVFDNNTNTKVGEAVTKEDGSYLIPNLP |
| SdrDB2 | KYNLGDYVWEDTNKNGIQ--DQDEKGISGVTVTLKDENGN-VLKTVTTDADGKYKFTDLD |
| SdrDB3 | KYNLGNYVWEDTNKDGKQ--DSTEKGISGVTVTLKNENGE-VLQTTKTDKDGKYQFTGLE |
| SdrDB4 | TYNLGDYVWEDTNKNGVQ--DKDEKGISGVTVTLKDENDK-VLKTVTTDENGKYQFTDLN |
| SdrDB5 | KYSLGDYVWYDSNKDGKQ--DSTEKGIDVKVTLLNEKGE-VIGTTKTDENGKYCFDNLD |
| SdrEB1 | LYKIGDYVWEDVDKDGVQGTDSKEKPMANVLVTLTYPDG--TTKSVRTDANGHYEFGGLK |
| SdrEB2 | KYNLGDYVWEDTNKDGIQ--DANEPGIKDVKVTLKDSTGK-VIGTTTTDASGKYKFTDLD |
| SdrEB3 | KYSLGDYVWYDSNKDGKQ--DSTEKGIKDVTVTLQNEKGE-VIGTTKTDENGKYRFDNLD |
| | *.*:*.**:* ; * .** : . ,.* *. : .* |

*FIG. 12A*

```
SdrCB1   NG-TYSVEFST-PAGYTPTTANVGTDDAVDSDGLTTTGVIKDADNMTLDSGFYKTP-
SdrCB2   SG-KYKVIFEK-PAGLTQTGTNTTEDD-KDADGGEVDVTITDHDDFTLDNGYYEEET
SdrDB1   NG-DYRVEFSNLPKGYEVTPSKQGNNEELDSNGLSSVITVNGKDNLSADLGIYKP--
SdrDB2   NG-NYKVEFTT-PEGYTPTTVTSGSDIEKDSNGLTTTGVINGADNMTLDSGFYKTP-
SdrDB3   NG-TYKVEFET-PSGYTPTQVGSGTDEGIDSNGTSTTGVIKDKDNDTIDSGFYKP--
SdrDB4   NG-TYKVEFET-PSGYTPTSVTSGNDTEKDSNGLTTTGVIKDADNMTLDSGFYKTP-
SdrDB5   SG-KYKVIFEK-PAGLTQTGTNTTEDD-KDADGGEVDVTITDHDDFTLDNGYYEEET
SdrEB1   DGETYTVKFET-PTGYLPTKVNGTTDGEKDSNGSSVTVKINGKDDMSLDTGFYKEP-
SdrEB2   NG-NYTVEFET-PAGYTPTVKNTTADD-KDSNGLTTTGVIKDADNMTLDRGFYKTP-
SdrEB3   SG-KYKVIFEK-PAGLTQTVTNTTEDD-KDADGGEVDVTITDHDDFTLDNGYFEDT
         .  * * *  . * *   *          :   *::*       ..  *: : * * ::
```

FIG. 12B

*Staphylococcus aureus* Consensus and Variable Motif

| Protein | Motif | | | | | | | |
|---|---|---|---|---|---|---|---|---|
| ClfA | I | Y | T | F | T | D | Y | V | N |
| ClfB | T | F | V | F | T | D | Y | V | N |
| SdrC | T | Y | T | F | T | D | Y | V | D |
| SdrD | T | Y | T | F | T | D | Y | V | D |
| SdrE | T | Y | T | F | T | D | Y | V | D |
| Consensus | T | Y | T | F | T | D | Y | V | D |
| Variable Motif | T/I | Y/F | T/V | F | T | D/N | Y | V | D/N |

FIG. 20

SDRE PROTEIN FROM *STAPHYLOCOCCUS AUREUS* AND DIAGNOSTIC KITS INCLUDING SAME

CROSS REFERENCE TO RELATED APPLICATIONS

The present application is a divisional application of U.S. application Ser. No. 10/744,616, filed Dec. 24, 2003 now abandoned, which is a divisional application of U.S. application Ser. No. 09/200,650, filed Nov. 25, 1998, now U.S. Pat. No. 6,680,195, and claims the benefit of U.S. Provisional Application No. 60/066,815 filed Nov. 25, 1997 and Ser. No. 60/098,427, filed Aug. 31, 1998, all of said applications incorporated herein by reference.

The U.S. Government has rights in this invention arising out of National Institutes of Health grant number A120624.

FIELD OF THE INVENTION

The present invention is in the fields of microbiology and molecular biology. The invention includes the isolation and use of extracellular matrix-binding proteins and genes that express the proteins from *Staphylococcus aureus* to inhibit, prevent and diagnose *S. aureus* infection.

BACKGROUND OF THE INVENTION

In hospitalized patients *Staphylococcus aureus* is a major cause of infections associated with indwelling medical devices, such as catheters and prostheses, and related infections of surgical wounds. A significant increase in *Staphylococcus aureus* isolates that exhibit resistance to most known antibiotics has been observed in hospitals throughout the world. The recent emergence of resistance to vancomycin, the last remaining antibiotic for treating methicillin-resistant *Staphylococcus aureus* (MRSA) infections, has emphasized the need for alternative prophylactic or vaccine strategies to reduce the risk of nosocomial *S. aureus* infections.

Initial localized infections of wounds or indwelling medical devices can lead to serious invasive infections such as septicemia, osteomyelitis, and endocarditis. In infections associated with medical devices, plastic and metal surfaces become coated with host plasma and extracellular matrix proteins such as fibrinogen and fibronectin shortly after implantation. The ability of *S. aureus* to adhere to these proteins is of crucial importance for initiating infection. Vascular grafts, intravenous catheters, artificial heart valves, and cardiac assist devices are thrombogenic and prone to bacterial colonization. *S. aureus* is the most damaging pathogen to cause such infections.

Fibrin is the major component of blood clots, and fibrinogen/fibrin is one of the major plasma proteins deposited on implanted biomaterials. Considerable evidence exists to suggest that bacterial adherence to fibrinogen/fibrin is important in the initiation of device-related infection. For example, as shown by Vaudaux et al., *S. aureus* adheres to in vitro plastic that has been coated with fibrinogen in a dose-dependent manner (J. Infect. Dis. 160:865-875 (1989)). In addition, in a model that mimics a blood clot or damage to a heart valve, Herrmann et al. demonstrated that *S. aureus* binds avidly via a fibrinogen bridge to platelets adhering to surfaces (J. Infect. Dis. 167: 312-322 (1993)). *S. aureus* can adhere directly to fibrinogen in blood clots formed in vitro, and can adhere to cultured endothelial cells via fibrinogen deposited from plasma acting as a bridge (Moreillon et al., *Infect. Immun.* 63:4738-4743 (1995); Cheung et al., *J. Clin. Invest.* 87:2236-2245 (1991)). As shown by Vaudaux et al. and Moreillon et al., mutants defective in the fibrinogen-binding protein clumping factor (ClfA) exhibit reduced adherence to fibrinogen in vitro, to explanted catheters, to blood clots, and to damaged heart valves in the rat model for endocarditis (Vaudaux et al., *Infect. Immun.* 63:585-590 (1995); Moreillon et al., *Infect. Immun.* 63: 4738-4743 (1995)).

An adhesin for fibrinogen, often referred to as "clumping factor," is located on the surface of *S. aureus* cells. The interaction between the clumping factor on bacteria and fibrinogen in solution results in the instantaneous clumping of bacterial cells. The binding site on fibrinogen is located in the C-terminus of the gamma chain of the dimeric fibrinogen glycoprotein. The affinity is very high and clumping occurs in low concentrations of fibrinogen. Scientists have recently shown that clumping factor also promotes adherence to solid phase fibrinogen, to blood clots, and to damaged heart valves (McDevitt et al., *Mol. Microbiol.* 11: 237-248 (1994); Vaudaux et al., *Infect. Immun.* 63:585-590 (1995); Moreillon et al., *Infect. Immun.* 63: 4738-4743 (1995)).

The gene for a clumping factor protein, designated ClfA, has been cloned, sequenced and analyzed in detail at the molecular level (McDevitt et al., *Mol. Microbiol.* 11: 237-248 (1994); McDevitt et al., *Mol. Microbiol.* 16:895-907 (1995)). The predicted protein is composed of 933 amino acids. A signal sequence of 39 residues occurs at the N-terminus followed by a 520 residue region (region A), which contains the fibrinogen binding domain. A 308 residue region (region R), composed of 154 repeats of the dipeptide serine-aspartate, follows. The R region sequence is encoded by the 18 basepair repeat GAYTCNGAYT CNGAYAGY (SEQ ID NO: 9) in which Y equals pyrimidines and N equals any base. The C-terminus of ClfA has features present in many surface proteins of Gram-positive bacteria such as an LPDTG (SEQ ID NO: 10) motif, which is responsible for anchoring the protein to the cell wall, a membrane anchor, and positive charged residues at the extreme C-terminus.

The platelet integrin alpha IIbβ3 recognizes the C-terminus of the gamma chain of fibrinogen. This is a crucial event in the initiation of blood clotting during coagulation. ClfA and alpha IIbβ3 appear to recognize precisely the same sites on fibrinogen gamma chain because ClfA can block platelet aggregation, and a peptide corresponding to the C-terminus of the gamma chain (198-411) can block both the integrin and ClfA interacting with fibrinogen (McDevitt et al., *Eur. J. Biochem.* 247:416-424 (1997)). The fibrinogen binding site of alpha IIbβ3 is close to, or overlaps, a $Ca^{2+}$ binding determinant referred to as an "EF hand". ClfA region A carries several EF hand-like motifs. A concentration of $Ca^{2+}$ in the range of 3-5 mM blocks these ClfA-fibrinogen interactions and changes the secondary structure of the ClfA protein. Mutations affecting the ClfA EF hand reduce or prevent interactions with fibrinogen. $Ca^{2+}$ and the fibrinogen gamma chain seem to bind to the same, or to overlapping, sites in ClfA region A.

The alpha chain of the leucocyte integrin, alpha Mβ2, has an insertion of 200 amino acids (A or I domain) which is responsible for ligand binding activities. A novel metal ion-dependent adhesion site (MIDAS) motif in the I domain is required for ligand binding. Among the ligands recognized is fibrinogen. The binding site on fibrinogen is in the gamma chain (residues 190-202). It was recently reported that *Candida albicans* has a surface protein, alpha Int1p, having properties reminiscent of eukaryotic integrins. The surface protein has amino acid sequence homology with the I domain of alpha Mβ2, including the MIDAS motif. Furthermore, alpha Int1p binds to fibrinogen.

ClfA region A also exhibits some degree of sequence homology with alpha IntIp. Examination of the ClfA region A sequence has revealed a potential MIDAS motif Mutations in supposed cation coordinating residues in the DXSXS (SEQ ID NO: 13) portion of the MIDAS motif in ClfA results in a significant reduction in fibrinogen binding. A peptide corresponding to the gamma-chain binding site for alpha Mβ2 (190-202) has been shown by O'Connell et al. to inhibit ClfA-fibrinogen interactions (O'Connell et al., *J. Biol. Chem.*, in press). Thus it appears that ClfA can bind to the gamma-chain of fibrinogen at two separate sites. The ligand binding sites on ClfA are similar to those employed by eukaryotic integrins and involve divalent cation binding EF-hand and MIDAS motifs.

Scientists have recently shown that *S. aureus* expresses proteins other than ClfA that may bind fibrinogen (Boden and Flock, *Mol. Microbiol.* 12:599-606 (1994)). One of these proteins is probably the same as the broad spectrum ligand-binding protein reported by Homonylo-McGavin et al., *Infect. Immun.* 61:2479-2485 (1993). Another is coagulase, as reported by Boden and Flock, *Infect. Immun.* 57:2358-2363 (1989), a predominantly extracellular protein that activates the plasma clotting activity of prothrombin. Coagulase binds prothrombin at its N-terminus and also interacts with soluble fibrinogen at its C-terminus Cheung et al., *Infect. Immun.* 63:1914-1920 (1995) have described a variant of coagulase that binds fibrinogen. There is some evidence that coagulase can contribute, in a minor way, to the ability of *S. aureus* cells to bind fibrinogen. As shown by Wolz et al., *Infect. Immun.* 64:3142-3147 (1996), in an agr regulatory mutant, where coagulase is expressed at a high level, coagulase appears to contribute to the binding of soluble fibrinogen to bacterial cells. Also, as shown by Dickinson et al., *Infect. Immun.* 63:3143-3150 (1995), coagulase contributes in a minor way to the attachment of *S. aureus* to plasma-coated surfaces under flow. However, it is clear that clumping factor ClfA is the major surface-located fibrinogen-binding protein responsible for bacterial attachment to immobilized fibrinogen/fibrin.

The identification and isolation of additional *S. aureus* extracellular matrix binding proteins would be useful for the development of therapies, diagnosis, prevention strategies and research tools for *S. aureus* infection.

Accordingly it is an object of the present invention to provide 15 isolated cell-wall associated extracellular matrix-binding proteins of *S. aureus* and active fragments thereof.

It is a further object of the invention to provide methods for preventing, diagnosing, treating or monitoring the progress of therapy for bacterial infections caused by *S. aureus*.

It is a further object of the present invention to provide isolated *S. aureus* surface proteins that are related in amino acid sequence to ClfA and are able to promote adhesion to the extracellular matrix or host cells.

It is another object of the present invention to generate antisera and antibodies to cell-wall associated extracellular matrix-binding proteins of *S. aureus*, or active fragments thereof.

It is a further object of the present invention to provide *S. aureus* vaccines, including a DNA vaccine.

It is a further object of the present invention to provide improved materials and methods for detecting and differentiating *S. aureus* organisms in clinical and laboratory settings.

It is a further object of the invention to provide nucleic acid probes and primers specific for *S. aureus*.

It is a further object of the invention to provide isolated extracellular matrix-binding proteins or peptides of *S. aureus*.

SUMMARY OF THE INVENTION

Isolated extracellular matrix-binding proteins, designated ClfB, SdrC, SdrD and SdrE, and their corresponding amino acid and nucleic acid sequences and motifs are described. The proteins, peptides, fragments thereof or antigenic portions thereof are useful for the prevention, inhibition, treatment and diagnosis of *S. aureus* infection and as scientific research tools. Further, antibodies or antibody fragments to the proteins, peptides, fragments thereof or antigenic portions thereof are also useful for the prevention, inhibition, treatment and diagnosis of *S. aureus* infection. The proteins, peptides, peptide fragments, antibodies, or antibody fragments can be administered in an effective amount to a patient in need thereof in any appropriate manner, preferably intravenously or otherwise by injection, to impart active or passive immunity. In an alternative embodiment, the proteins or antibodies thereof can be administered to wounds or used to coat biomaterials to act as blocking agents to prevent or inhibit the binding of *S. aureus* to wounds or biomaterials.

Specifically, extracellular matrix-binding proteins from *S. aureus* designated as ClfB, SdrC, SdrD, and SdrE are provided.

ClfB is a fibrinogen binding protein. The nucleic acid and amino acid sequences of ClfB are provided in FIG. 5. The amino acid sequence of ClfB is SEQ ID NO: 1, and the nucleic acid sequence of ClfB is SEQ ID NO:2.

SdrC has been discovered to bind to several extracellular matrix proteins of the host, including for example, bone sialoprotein (BSP), decorin, plasmin, fibrinogen and vitronectin. The amino acid and nucleic acid sequences of SdrC are SEQ ID NOS:3 and 4 respectively and are provided in FIG. 7.

Another of the discovered proteins, SdrD, binds at least vitronectin. The amino acid and nucleic acid sequences of SdrD are SEQ ID NOS:5 and 6 respectively and are provided in FIG. 8.

SdrE binds to extracellular matrix proteins, for example, bone sialoprotein (BSP). The amino acid and nucleic acid sequences of SdrE are SEQ ID NOS:7 and 8 respectively and are provided in FIG. 9.

ClfB has a predicted molecular weight of approximately 88 kDa and an apparent molecular weight of approximately 124 kDa. ClfB is a cell-wall associated protein and binds both soluble and immobilized fibrinogen. In addition, ClfB binds both the alpha and beta chains of fibrinogen and acts as a clumping factor. SdrC, SdrD and SdrE are cell-wall associated proteins that exhibit cation-dependent ligand binding of extracellular matrix proteins such as decorin, plasmin, fibrinogen, vitronectin and BSP.

It has been discovered that in the A region of SdrC, SdrD, SdrE, ClfA, and ClfB, there is highly conserved amino acid sequence that can be used to derive a consensus TYTFT-DYVD (SEQ ID NO: 18) motif (see FIG. 20). The motif can be used in vaccines to impart broad spectrum immunity against bacterial infections. The motif can also be used as an antigen in the production of monoclonal or polyclonal antibodies to impart broad spectrum passive immunity. In an alternative embodiment, any combination of the variable sequence motif (T/I) (Y/F) (T/V) (F) (T) (D/N) (Y) (V) (D/N) can be used as an immunogen or antigen, or in the preparation of antibodies.

The ClfB, SdrC, SdrD and SdrE proteins or the consensus or variable motifs thereof are useful as scientific research tools to identify *S. aureus* binding sites on the extracellular matrix. They are further useful as research tools to promote an understanding of the mechanisms of bacterial pathology and the development of antibacterial therapies.

The ClfB, SdrC, SdrD and SdrE nucleic acid sequences or selected fragments thereof, including the sequences encoding the consensus or variable motifs, are useful as nucleic acid probes for the identification of other S. aureus extracellular matrix-binding proteins. Alternatively, the amino acid sequences of the proteins, or selected fragments thereof, can be used as probes to identify the corresponding nucleic acid sequences.

The ClfB, SdrC, SdrD and SdrE nucleic acid sequences or the sequences encoding the consensus or variable motifs are further useful as polynucleotides which comprise contiguous nucleic acid sequences capable of being expressed. The nucleic acid sequences may be inserted into a vector and placed in a microorganism for the production of recombinant ClfB, SdrC, SdrD and SdrE proteins or the variable or consensus amino acid motifs. This allows for the production of the gene product upon introduction of said polynucleotide into eukaryotic tissues in vivo. The encoded gene product preferably either acts as an immunostimulant or as an antigen capable of generating an immune response. Thus, the nucleic acid sequences in this embodiment encode an MSCRAMM (Microbial Surface Components Recognising Adhesive Matrix Molecules) immunogenic epitope, and optionally a cytokine or a T-cell costimulatory element, such as a member of the B7 family of proteins.

There are several advantages of immunization with a gene rather than its gene product. The first is the relative simplicity with which native or nearly native antigen can be presented to the immune system. A second advantage of DNA immunization is the potential for the immunogen to enter the MHC class I pathway and evoke a cytotoxic T cell response. Cell-mediated immunity is important in controlling infection. Since DNA immunization can evoke both humoral and cell-mediated immune responses, its greatest advantage may be that it provides a relatively simple method to survey a large number of S. aureus genes for their vaccine potential.

Antibodies immunoreactive with ClfB, SdrC, SdrD and SdrE proteins, or their active fragments, including with the consensus or variable amino acid motifs, are provided herein. Vaccines or other pharmaceutical compositions containing the proteins or amino acid motifs are additionally provided herein.

Antibodies and antisera to the consensus TYTFTDYVD (SEQ ID NO: 18) sequence epitope or the variable (T/I) (Y/F) (T/V) (F) (T) (D/N) (Y) (V) (D/N) sequence, specifically TYTFTNYVD (SEQ ID NO: 19) in SdrC, TYTFTDYVD (SEQ ID NO: 18) in SdrD and SdrE, TFVFTDYVN (SEQ ID NO: 20) in ClfB or IYTFTDYVN (SEQ ID NO: 21) in ClfA are provided herein. Vaccines or other pharmaceutical compositions containing the epitopes are also provided herein.

In addition, diagnostic kits containing nucleic acid molecules, the proteins, antibodies or antisera to ClfB, SdrC, SdrD, SdrE or their active fragments, including the consensus or variable amino acid motifs and the appropriate reagents for reaction with a sample are also provided.

In one embodiment of the invention, the diagnostic kit is used to identify patients or animals that have levels of antibodies to ClfB ClfB, SdrC, SdrD, or SdrE that are above a population norm. The plasma of the patients or animals can be obtained, processed, and administered to a host in need of passive immunity to S. aureus infection.

BRIEF DESCRIPTION OF THE FIGURES

FIG. 1 is a schematic representation comparing features of unprocessed ClfA and ClfB proteins. S indicates the signal sequence. A indicates the conserved region (region A). P indicates the proline-rich region (repeats are indicated by gray boxes). R indicates the SD repeat region (region R). W indicates the wall-spanning region. M indicates the membrane spanning and anchoring regions. EF hand I of ClfA and its partial homologue on ClfB are indicated by black vertical bars. The MIDAS motifs are indicated by hatched (DXSXS) (SEQ ID NO: 13) and narrow vertical lines (downstream T and D residues) connected by dashed lines.

FIG. 2 is a schematic representation of general plasmid and probe constructions for sequencing clfB. A repeat-carrying EcoRI fragment was cloned from phage clone A1-1 into pGEM 7Z (f)+to give pA1-1E (top), and subsequently reduced by deletion of an XbaI fragment to give pA1-1EX, which contains the entire clfB gene. A SmaI fragment containing clfB and 500 by of upstream DNA was cloned into pCU1 for overexpression and complementation work (pA1-1EA). The HpaI probe used to screen mutants, and the hybridizing BamHI fragment are also indicated.

FIG. 3 is a schematic representation showing construction of a cassette for allele replacement. clfB was interrupted by blunt-end cloning the Tc determinant from pT181 into the HpaI site in the middle of the gene in pA1-1EX. pTS2 was then cloned into the SmaI site of the cassette to enable temperature sensitive propagation in S. aureus.

FIGS. 5A-5D show the nucleic acid sequence of ClfB and flanking DNA, and amino acid translation of the ORF. The likely start codon is double underlined, and the principal regions indicated using the abbreviations of FIG. 1. Two salient features of region A, the DYSNS (SEQ ID NO: 11) of the putative MIDAS motif, and the sequence FTDYVN (SEQ ID NO: 12), the longest region of identity with ClfB, are underlined. Vertical bars indicate the repeats in the proline-rich region. An inverted repeat specifying a possible transcription termination signal is underlined.

FIG. 6 is an amino acid sequence alignment of part of region A of the ClfB and ClfA proteins in the region of strongest similarity. EF hand I of ClfA is underlined. Identical residues are denoted by an asterisk; conservative substitutions are denoted by a period. The DXSXS (SEQ ID NO: 13) portion of the MIDAS motif of ClfB is double underlined.

FIGS. 7A-7D show the nucleic acid sequence and amino acid translation of the sdrC gene. The consensus TYTFTDYVD (SEQ ID NO: 18) motif, expressed in SdrC as TYTFTNYVD (SEQ ID NO: 19), the EF hands in the B repeats, and the LPXTG (SEQ ID NO: 14) motif are underlined. Major regions, such as the signal sequence (S), region A (A), B repeats (B) region R(R), the wall-spanning domain (W), and the membrane-anchoring domain (M), are indicated.

FIGS. 8A-8E show the nucleic acid sequence and amino acid translation of the sdrD gene. The consensus TYTFTDYVD (SEQ ID NO: 18) motif, the EF hands in the B repeats, and the LPXTG (SEQ ID NO: 14) motif are underlined. Major regions, such as the signal sequence (S), region A (A), B repeats (B) region R(R), the wall-spanning domain (W), and the membrane-anchoring domain (M), are indicated.

FIGS. 9A-9D show the nucleic acid sequence and amino acid translation of the sdrE gene. The consensus TYTFTDYVD (SEQ ID NO: 18) motif, the EF hands in the B repeats, and the LPXTG (SEQ ID NO: 14) motif are underlined. Major regions, such as the signal sequence (S), region A (A), B repeats (B) region R(R), the wall-spanning domain (W), and the membrane-anchoring domain (M), are indicated.

FIG. 11 is a chart showing similarities between A regions ClfA, ClfB, SdrC, SdrD and SdrE. Each sequence was aligned in pairwise combinations and the percent identical residues given.

FIGS. 12A-12B show Clustal™ multiple sequence alignments of areas of similarity of the A and B regions of the region R containing genes of strain Newman. An asterisk denotes identity of amino acids, and a colon represents increasing similarity of polarity and hydrophobicity/hydrophilicity of side chains of amino acids. Alignments 1-4 show areas from region A. Alignments 1, 3 and 4 show the common motifs. Alignment 2 shows homology in the vicinity of the ClfA EF-hand (underlined), with the consensus TYTFTDYVD (SEQ ID NO: 18) sequence conserved in all five genes. Alignment 5 shows the B repeats of proteins SdrC, SdrD and SdrE with possible EF hands underlined.

FIG. 20 is a table which shows the highly conserved amino acid sequences in the A region of ClfA, ClfB, SdrC, SdrD and SdrE, which are used to provide consensus and variable motifs.

DETAILED DESCRIPTION OF THE INVENTION

Figure 4:
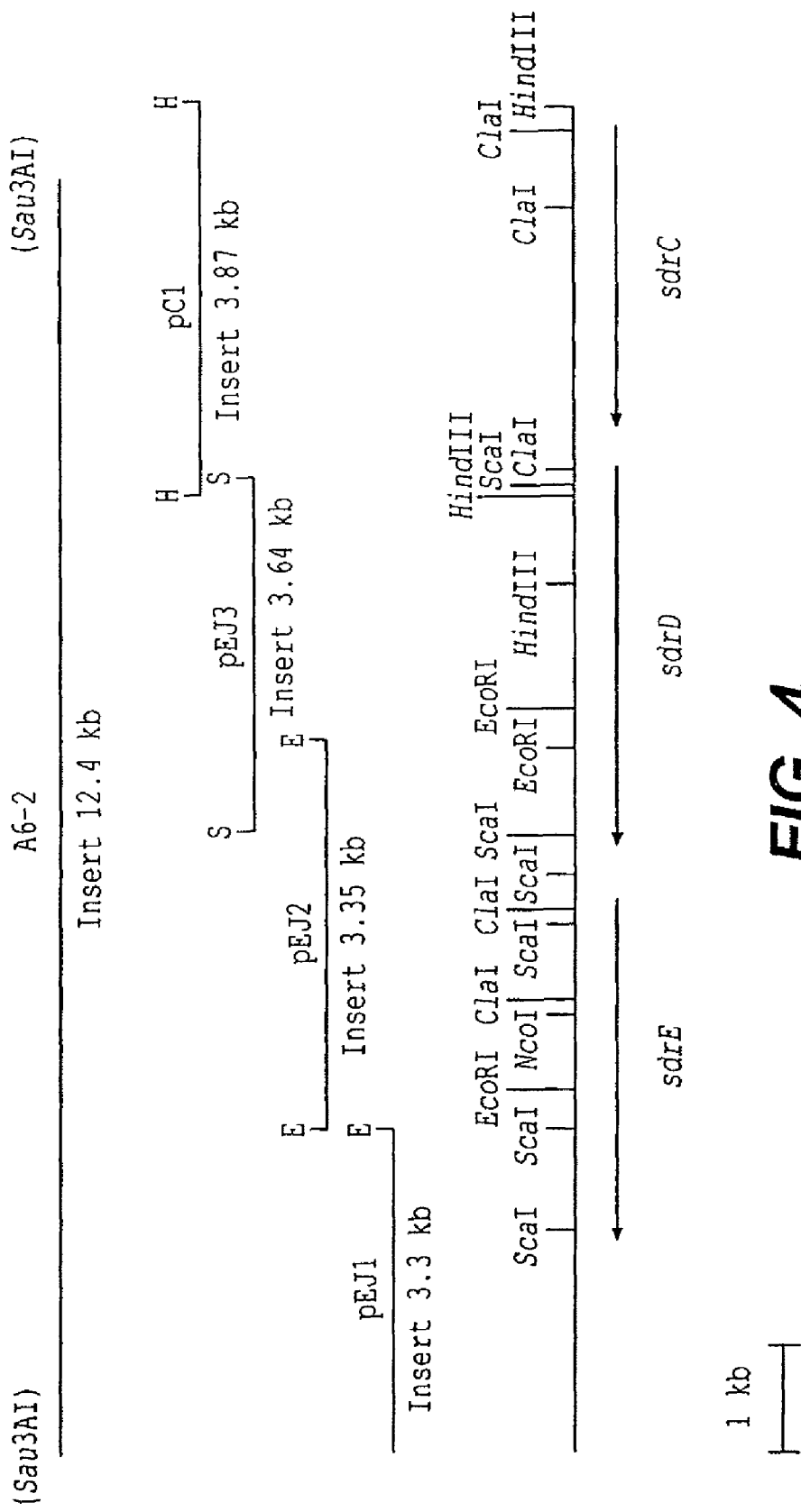
FIG. 4 is a schematic representation of a physical map of the sdrC sdrD sdrE locus in S. aureus strain Newman. The extents of the plasmid clones are delineated. A6-2 is a LambdaGEM®-12 clone. pEJ1, pEJ2 and pEJ3 are A6-2 fragments subcloned in the pGEM 7Z (f)+(pEJ 1 and pEJ2) and the pBluescript KS+vector (pEJ3). pC1 is a HindIII fragment directly cloned from strain Newman in the pBluescript KS+vector. Arrows indicate the direction of transcription of sdrC, sdrD and sdrE.

Isolated extracellular matrix-binding proteins, designated ClfB, SdrC, SdrD and SdrE, and their corresponding amino acid and nucleic acid sequences and motifs are described. The proteins, peptides, fragments thereof or antigenic portions thereof are useful for the prevention, inhibition, treatment and diagnosis of *S. aureus* infection and as scientific research tools. Further, antibody or antibody fragments to the proteins, peptides, fragments thereof or antigenic portions thereof are also useful for the prevention, inhibition, treatment and diagnosis of *S. aureus* infection. In particular, the proteins or antibodies, or active fragments thereof may be administered as vaccines to induce either passive or cellular immunity.

ClfB Binds to at Least Fibrinogen.

SdrC has been discovered to bind to extracellular matrix proteins of the host, including for example, BSP, decorin, plasmin, vitronectin and fibrinogen. SdrD binds to at least vitronectin. SdrE binds to extracellular matrix proteins, for example, bone sialoprotein (BSP).

The amino acid sequence of ClfB is SEQ ID NO: 1. The nucleic acid sequence encoding ClfB is SEQ ID NO:2. The nucleic acid and amino acid sequences of ClfB are also provided in FIG. 5. The amino acid and nucleic acid sequences of SdrC are SEQ ID NOS:3 and 4 respectively and are provided in FIG. 7. The amino acid and nucleic acid sequences of SdrD are SEQ ID NOS:5 and 6 respectively and are provided in FIG. 8. The amino acid and nucleic acid sequences of SdrE are SEQ ID NOS:7 and 8 respectively and are provided in FIG. 9. The term "isolated" is defined herein as free from at least some of the components with which it naturally occurs. In a preferred embodiment, an isolated component is at least 90% pure, and more preferably 95%.

ClfB has a predicted molecular weight of approximately 88 kDa and an apparent molecular weight of approximately 124 kDa. ClfB is a cell-wall associated protein and binds both soluble and immobilized fibrinogen. In addition, ClfB binds both the alpha and beta chains of fibrinogen and acts as a clumping factor. Despite the low level of identity between ClfA and ClfB, both proteins bind fibrinogen (on different chains) by a mechanism that is susceptible to inhibition by divalent cations, despite not sharing obvious metal binding motifs. The ClfB protein has been demonstrated to be a virulence factor in experimental endocarditis.

The SdrC, SdrD and SdrE proteins are related in primary sequence and structural organization to the ClfA and ClfB proteins and are localized on the cell surface. The SdrC, SdrD and SdrE proteins are cell wall-associated proteins, having a signal sequence at the N-terminus and an LPXTG (SEQ ID NO: 14) motif, hydrophobic domain and positively charged residues at the C-terminus. Each also has an SD repeat containing region R of sufficient length to allow, along with the B motifs, efficient expression of the ligand binding domain region A on the cell surface. With the A region of the SdrC, SdrD and SdrE proteins located on the cell surface, the proteins can interact with proteins in plasma, the extracellular matrix or with molecules on the surface of host cells. The Sdr proteins share some limited amino acid sequence similarity with ClfA and ClfB. Like ClfA and ClfB, SdrC, SdrD and SdrE also exhibit cation-dependent ligand binding of extracellular matrix proteins.

It was surprising to learn that the disclosed extracellular matrix-binding proteins share a unique dipeptide repeat region (region R) including predominately aspartate and serine residues. It had been reported by McDevitt et al., *Mol. Microbiol.* 11: 237-248 (1994); McDevitt et al., *Mol. Microbiol.* 16:895-907 (1995) that ClfA also has this R repeat region. He reported that that there were genes in *S. epidermidus* that hybridized to the gene encoding the R domain containing protein. However, McDevitt et al did not know the function of the R region and had not discovered that other cell surface proteins from *S. aureus*, *S. hemolyticus*, *S. lugdenensis*, *S. schleriferi* share this unusual motif. Therefore, in one aspect of this invention, a method is provided for the identification of genes and encoding proteins from *S. aureus* (other than ClfA), *S. hemolyticus*, *S. lugdenensis*, *S. schleriferi* useful for the prevention, treatment, and diagnosis of bacterial infection that includes using the R repeat region as an identifying probe.

The DS repeat is encoded by 18 nucleotide repeats with the consensus (where Y equals pyrimidines and N equals any base) GAYTCNGAYT CNGAYAGY (SEQ ID NO: 9, with TCN as the first and second serine codons and AGY as the third serine codon. The R region is near the C-terminus of the proteins and typically contains between 40 and 300 DS residues, or more particularly, greater than 40, 60, 80, 100, 125, 150, 200 or 250 repeating units, of which greater than 90, 95 or even 98% of the amino acids are D or S. The R region DS repeat varies in length between proteins, and while the R region itself does not bind extracellular matrix proteins, the R region enables the presentation of the binding regions of the protein on the cell surface of *S. aureus*. Thus, probes to the consensus DNA encoding the DS repeat (see above) can be used to identify other genes encoding different binding proteins essential to the attachment of *S. aureus* to host tissues. Antibodies to an R region can be used to discover such additional binding proteins as well.

The sdr genes are closely linked and tandemly arrayed. The Sdr proteins have both organizational and sequence similarity to ClfA and ClfB. At the N-terminus secretory signal sequences precede A regions which are approximately 500 residues in length. The A regions of the Sdr and Clf proteins exhibit only 20-30% residue identity when aligned with any other member of the family.

It has been discovered that in the A region of SdrC, SdrD, SdrE, ClfA, and ClfB, there is highly conserved amino acid sequence that can be used to derive a consensus TYTFT-DYVD (SEQ ID NO: 18) motif The motif exhibits slight variation between the different proteins. This variation, along with the consensus sequence of the motif is depicted in FIG. 20. In the Clf-Sdr proteins, this motif is highly conserved. The motif can be used in vaccines to impart broad spectrum cellular immunity to bacterial infections, and also can be used as an antigen in the production of monoclonal or polyclonal antibodies. Such an antibody can be used to impart broad spectrum passive immunity.

The Sdr proteins differ from ClfA and ClfB by having two to five additional 110-113 residue repeated sequences (B-motifs) located between region A and the R-region. Each B-motif contains a consensus $Ca^{2+}$-binding EF-hand loop normally found in eukaryotic proteins. The structural integrity of a recombinant protein comprising the five B-repeats of SdrD was shown by bisANS fluorescence analysis to be $Ca^{2+}$-dependent, suggesting that the EF-hands are functional. When $Ca^{2+}$ was removed the structure collapsed to an unfolded conformation. The original structure was restored by addition of $Ca^{2+}$. The C-terminal R-domains of the Sdr proteins contain 132-170 SD residues. These are followed by conserved wall-anchoring regions characteristic of many surface proteins of Gram positive bacteria. The sdr locus was present in all 31 *S. aureus* strains from human and bovine sources tested by Southern hybridization, although in a few strains it contained two rather than three genes.

In the Sdr and Clf proteins this B motif is highly conserved while a degenerate version occurs in fibronectin binding MSCRAMMS, as well as the collagen binding protein Cna. The B motifs, in conjunction with the R regions, are necessary for displaying the ligand-binding domain at some distance from the cell surface.

The repeated B motifs are one common denominator of the sub-group of SD repeat proteins described herein. These motifs are found in different numbers in the three Sdr proteins from strain Newman. There are clear distinctions between the individual B motifs. The most conserved units are those located adjacent to the R regions (SdrC B2, SdrD B5 and SdrE B3). They differ from the rest at several sites, especially in the C-terminal half. A noteworthy structural detail is that adjacent B repeats are always separated by a proline residue present in the C-terminal region, but a proline never occurs between the last B repeats and the R region. Instead this linker is characterized by a short acidic stretch. These differences are evidence that the end units have a different structural or functional role compared to the other B motifs. The N-terminal B motifs of SdrD and SdrE have drifted apart from the others, and there are numerous amino acid alterations, including small insertions and deletions whereas the remaining internal B motifs are more highly conserved. Note that each of the three Sdr proteins has at least one B motif of each kind.

The C-terminal R-domains of the Sdr proteins contain 132-170 SD residues. These are followed by conserved wall-anchoring regions characteristic of many surface proteins of Gram positive bacteria.

Figure 10:
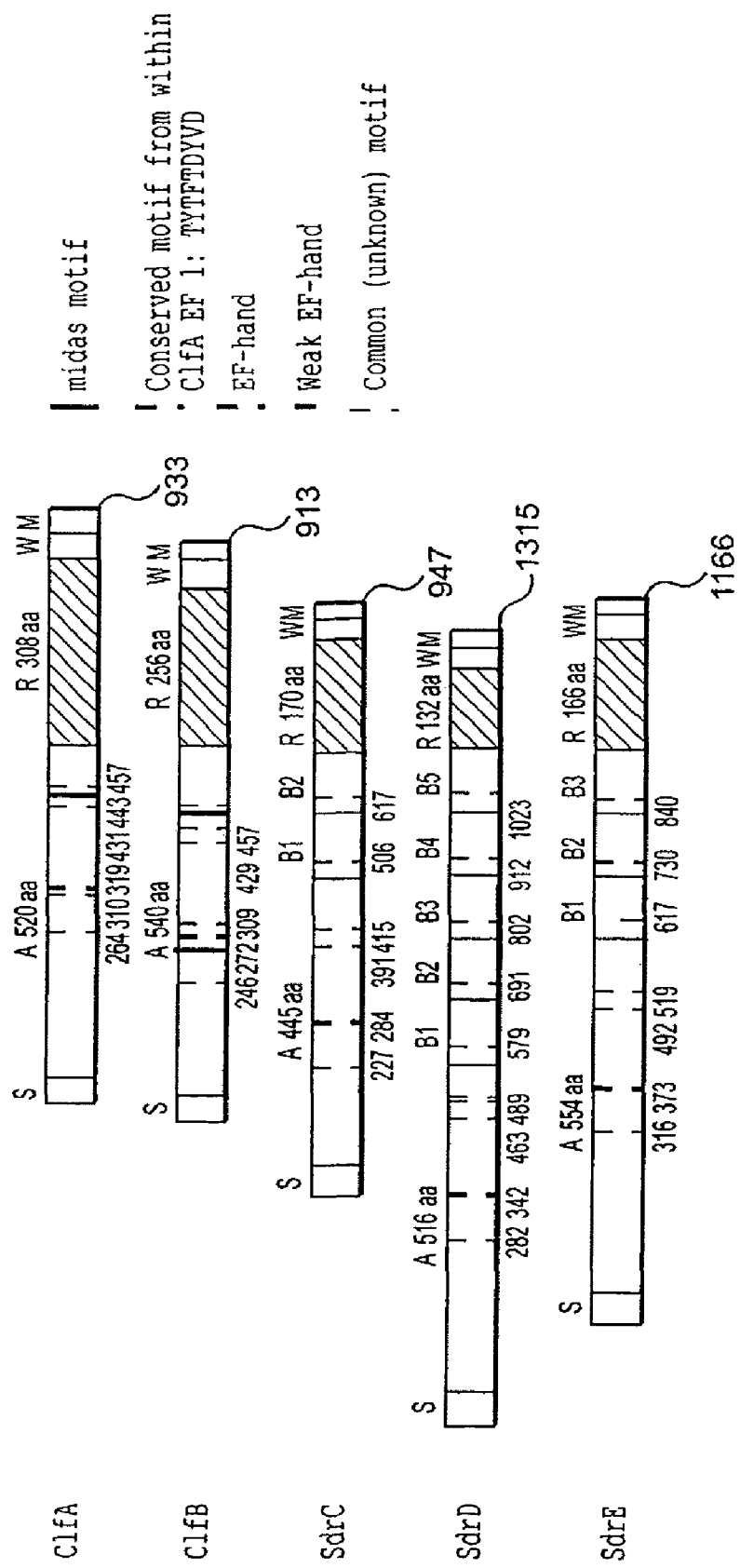
FIG. 10 is a schematic diagram of the region R-containing proteins. Numerals over the proteins denote numbers of amino acids in the regions, numerals under the proteins denote the location on the amino acid sequence of the motifs counted from the beginning of the signal peptide. Abbreviations: S: Signal peptide; A: Region A; B: B repeat; R: Region R; W. M: Wall and membrane spanning regions.

ClfB, SdrC, SdrD and SdrE subdomains are shown in FIG. 10 and, depending on the protein, include subdomains A and B1-B5.

The terms ClfB protein, SdrC protein, SdrD protein and SdrE protein are defined herein to include ClfB, SdrC, SdrD and SdrE subdomains, and active or antigenic fragments of ClfB, SdrC, SdrD and SdrE proteins, such as consensus or variable sequence amino acid motifs. Active fragments of ClfB, SdrC, SdrD, SdrE and consensus or variable sequence amino acid motifs peptides or proteins are defined herein as peptides or polypeptides capable of blocking the binding of S. aureus to extracellular matrix proteins. Antigenic fragments of ClfB, SdrC, SdrD, SdrE proteins or the consensus or variable amino acid motifs are defined herein as peptides or polypeptides capable of producing an immunological response.

Nucleic Acid Sequences

The nucleic acid sequences encoding ClfB, SdrC, SdrD, SdrE and the consensus or variable sequence amino acid motifs are useful for the production of recombinant extracellular matrix-binding proteins. They are further useful as nucleic acid probes for the detection of S. aureus-binding proteins in a sample or specimen with high sensitivity and specificity. The probes can be used to detect the presence of S. aureus in the sample, diagnose infection with the disease, quantify the amount of S. aureus in the sample, or monitor the progress of therapies used to treat the infection. The nucleic acid and amino acid sequences are also useful as laboratory research tools to study the organism and the disease, thus furthering the development of therapies and treatments for the disease.

It will be understood by those skilled in the art that ClfB, SdrC, SdrD, SdrE and the consensus or variable sequence amino acid motifs are also encoded by sequences substantially similar to the nucleic acid sequences provided in the sequence listing. By "substantially similar" is meant a DNA sequence which, by virtue of the degeneracy of the genetic code, is not identical with that shown in any of SEQ ID NOS: 2, 4, 6, and 8, but which still encodes the same amino acid sequence; or a DNA sequence which encodes a different amino acid sequence but retains the activities of the proteins, either because one amino acid is replaced with another similar amino acid, or because the change (whether it be substitution, deletion or insertion) does not affect the active site of the protein. In the latter case, the sequence has substantial homology to the disclosed sequence if it encodes a protein with at least 70% 80%, 90%, 95% or even 98% of the same amino acids.

Also provided herein are sequences of nucleic acid molecules that selectively hybridize with nucleic acid molecules encoding the extracellular matrix-binding proteins from S. aureus described herein or complementary sequences thereof. By "selective" or "selectively" is meant a sequence which does not hybridize with other nucleic acids to prevent adequate detection of ClfB, SdrC, SdrD, SdrE or the consensus or variable sequence amino acid motifs. Therefore, in the design of hybridizing nucleic acids, selectivity will depend upon the other components present in a sample. The hybridizing nucleic acid should have at least 70% complementarity with the segment of the nucleic acid to which it hybridizes. As used herein to describe nucleic acids, the term "selectively hybridizes" excludes the occasional randomly hybridizing nucleic acids, and thus, has the same meaning as "specifically hybridizing". The selectively hybridizing nucleic acids of the invention can have at least 70%, 80%, 85%, 90%, 95%, 97%, 98%, and 99% complementarity with the segment of the sequence to which it hybridizes.

The invention contemplates sequences, probes and primers which selectively hybridize to the encoding DNA or the complementary, or opposite, strand of DNA as those specifically provided herein. Specific hybridization with nucleic acid can occur with minor modifications or substitutions in the nucleic acid, so long as functional species-specific hybridization capability is maintained. By "probe" is meant nucleic acid sequences that can be used as probes or primers for selective hybridization with complementary nucleic acid sequences for their detection or amplification, which probes can vary in length from about 5 to 100 nucleotides, or preferably from about 10 to 50 nucleotides, or most preferably about 18-24 nucleotides. Therefore, the terms "probe" or "probes" as used herein are defined to include "primers". Isolated nucleic acids are provided herein that selectively hybridize with the species-specific nucleic acids under stringent conditions and should have at least 5 nucleotides complementary to the sequence of interest as described by Sambrook, J., E. F. Fritsch, and T. Maniatis. 1989. MOLECULAR CLONING: A LABORATORY MANUAL, 2nd ed. Cold Spring Harbor Laboratory, Cold Spring Harbor, N.Y.

If used as primers, the composition preferably includes at least two nucleic acid molecules which hybridize to different regions of the target molecule so as to amplify a desired region. Depending on the length of the probe or primer, the target region can range between 70% complementary bases and full complementary and still hybridize under stringent conditions. For example, for the purpose of diagnosing the presence of the S. aureus, the degree of complementary between the hybridizing nucleic acid (probe or primer) and the sequence to which it hybridizes (e.g., S. aureus DNA from a sample) is at least enough to distinguish hybridization with a nucleic acid from other bacteria.

The nucleic acid sequences encoding ClfB, SdrC, SdrD, SdrE active fragments thereof or consensus or variable sequence amino acid motifs can be inserted into a vector, such as a plasmid, and recombinantly expressed in a living organism to produce recombinant ClfB, SdrC, SdrD and SdrE proteins or fragments thereof, such as consensus or variable sequence amino acid motifs. For example, DNA molecules producing recombinant ClfB, SdrC, and both SdrD and SdrE were deposited in plasmids pA1-1EX, pC1 and lambda phage A6-2, respectively, at the NCIMB under the Accession Nos. 40903, 40902 and 40904, respectively on Oct. 13, 1997.

Methods for the Detection and Identification of S. aureus

Methods of using the nucleic acids described herein to detect and identify the presence of S. aureus are provided. The methods are useful for diagnosing S. aureus infections and disease such as upper respiratory tract infections (such as otitis media, bacterial tracheitis, acute epiglottitis, thyroiditis), lower respiratory infections (such as emphysema, lung abscess), cardiac (such as infective endocarditis), gastrointestinal (such as secretory diarrhea, splenic abscess, retroperitoneal abscess), central nervous system (such as cerebral abscess), ocular (such as blepharitis, conjunctivitis, keratitis, endophthalmitis, preseptal and orbital cellulitis, darcryocystitis), kidney and urinary tract (such as epididymitis, intrarenal and perinephric abscess, toxic shock syndrome), skin (such as impetigo, folliculitis, cutaneous abscesses, cellulitis, wound infection, bacterial myositis, bone and joint (such as septic arthritis, osteomyelitis).

The method involves the steps of obtaining a sample suspected of containing S. aureus The sample may be taken from an individual, such as a wound, blood, saliva, tissues, bone, muscle, cartilage, or skin. The cells can then be lysed, and the DNA extracted, precipitated and amplified. Detection of S. aureus DNA is achieved by hybridizing the amplified DNA with a S. aureus probe that selectively hybridizes with the DNA as described above. Detection of hybridization is indicative of the presence of S. aureus.

Preferably, detection of nucleic acid (e.g. probes or primers) hybridization can be facilitated by the use of detectable moieties. For example, the probes can be labeled with biotin and used in a streptavidin-coated microtiter plate assay. Other detectable moieties include radioactive labeling, enzyme labeling, and fluorescent labeling, for example.

DNA may be detected directly or may be amplified enzymatically using polymerase chain reaction (PCR) or other amplification techniques prior to analysis. RNA or cDNA can be similarly detected. Increased or decreased expression of ClfB, SdrC, SdrD, SdrE and consensus or variable sequence amino acid motifs can be measured using any of the methods well known in the art for the quantitation of nucleic acid molecules, such as, amplification, PCR, RT-PCR, RNase protection, Northern blotting, and other hybridization methods.

Diagnostic assays which test for the presence of the ClfB or SdrC, SdrD or SdrE proteins, peptides, motifs, fragments thereof or antibodies to any of these may also be used to detect the presence of an infection. Assay techniques for determining protein or antibody levels in a sample are well known to those skilled in the art and include methods such as radioimmunoassay, Western blot analysis and ELISA (Enzyme-Linked Immunosorbant Assay) assays.

Amino Acid Sequences

It will be understood by those skilled in the art that minor amino acid substitutions or deletions may be present in functional ClfB, SdrC, SdrD, SdrE and consensus or variable sequence amino acid motifs, peptides, proteins, or fragments thereof. The amino acid sequences set forth herein and substantially similar amino acid sequences can be used to produce synthetic ClfB, SdrC, SdrD, SdrE and consensus or variable sequence amino acid motifs, peptides, proteins or active fragments thereof. Active ClfB, SdrC, SdrD, SdrE or consensus or variable sequence amino acid motifs, peptide or protein fragments are defined herein as ClfB, SdrC, SdrD, SdrE or consensus or variable sequence amino acid motifs, portions or peptides that bind to extracellular matrix proteins or compete with or prevent S. aureus organisms from binding to extracellular matrix proteins such as decorin, plasmin, fibrinogen, vitronectin or bone sialoprotein.

When used in conjunction with amino acid sequences, the term "substantially similar" means an amino acid sequence which is not identical to SEQ ID NOS:1, 3, 5, or 7, but which produces a protein having the same functionality and retaining the activities of ClfB, SdrC, SdrD, SdrE and consensus or variable sequence amino acid motifs, either because one amino acid is replaced with another similar amino acid, or because the change (whether it be substitution, deletion or insertion) does not affect the active site of the protein or peptide. Two amino acid sequences are "substantially homologous" when at least about 70%, (preferably at least about 80%, and most preferably at least about 90% or 95%) of the amino acids match over the defined length of the sequences.

Extracellular Matrix-Binding Protein Antibodies

The isolated, recombinant or synthetic ClfB, SdrC, SdrD, SdrE or consensus or variable sequence amino acid motifs, or peptides or active fragments thereof or fusion proteins thereof, are useful as scientific research tools to identify S. aureus binding sites on the extracellular matrix. This will promote an understanding of the mechanisms of bacterial pathology and the development of antibacterial therapies. Furthermore, the isolated, recombinant or synthetic protein, or antigenic portions thereof (including epitope-bearing fragments), or fusion proteins thereof can be administered to humans or animals as immunogens or antigens. It can be administered alone or in combination with an adjuvant, for the production of antisera reactive with ClfB, SdrC, SdrD, SdrE or motifs or peptides thereof. In addition, the peptides or proteins can be used to screen antisera for hyperimmune patients from whom can be derived antibodies having a very high affinity for the proteins.

Antibodies isolated from the antisera are useful for the specific detection of S. aureus or S. aureus extracellular matrix-binding proteins or as research tools. The term "antibodies" as used herein includes monoclonal antibodies, polyclonal, chimeric, single chain, bispecific, simianized, and humanized antibodies as well as Fab fragments, including the products of an Fab immunoglobulin expression library.

Monoclonal antibodies are generated by methods well known to those skilled in the art. The preferred method is a modified version of the method of Kearney, et al., J. Immunol. 123:1548-1558 (1979), which is incorporated by reference herein. Briefly, animals such as mice or rabbits are inoculated with the immunogen in adjuvant, and spleen cells are harvested and mixed with a myeloma cell line, such as P3X63Ag8,653. The cells are induced to fuse by the addition of polyethylene glycol. Hybridomas are chemically selected by plating the cells in a selection medium containing hypoxanthine, aminopterin and thymidine (HAT). Hybridomas producing the preferred antibodies are cloned, expanded and stored frozen for future production.

Techniques for the production of single chain antibodies are known to those skilled in the art and described in U.S. Pat. No. 4,946,778 and can be used to produce single chain antibodies to the proteins described herein. Phage display technology may be used to select antibody genes having binding activities for ClfB, SdrC, SdrD, SdrE, and consensus or variable sequence amino acid motifs, or antigenic portions thereof, from PCR-amplified v genes of lymphocytes from humans screened for having antibodies to ClfB, SdrC, SdrD, SdrE or consensus or variable sequence amino acid motifs or naive libraries. Bispecific antibodies have two antigen binding domains wherein each domain is directed against a different epitope.

The antibody may be labeled directly with a detectable label for identification and quantitation of S. aureus. Labels for use in immunoassays are generally known to those skilled in the art and include enzymes, radioisotopes, and fluorescent, luminescent and chromogenic substances including colored particles such as colloidal gold and latex beads. Suitable immunoassays include enzyme-linked immunosorbent assays (ELISA).

Alternatively, the antibody may be labeled indirectly by reaction with labeled substances that have an affinity for immunoglobulin, such as protein A or G or second antibodies. The antibody may be conjugated with a second substance and detected with a labeled third substance having an affinity for the second substance conjugated to the antibody. For example, the antibody may be conjugated to biotin and the antibody-biotin conjugate detected using labeled avidin or streptavidin. Similarly, the antibody may be conjugated to a hapten and the antibody-hapten conjugate detected using labeled anti-hapten antibody. These and other methods of labeling antibodies and assay conjugates are well known to those skilled in the art.

Antibodies to the disclosed proteins may also be used in production facilities or laboratories to isolate additional quantities of the protein, such as by affinity chromatography.

The proteins, or antigenic portions thereof, are useful in the diagnosis of S. aureus bacterial infections and in the development of anti-S. aureus vaccines for active or passive immunization. When administered to a wound or used to coat polymeric biomaterials in vitro and in vivo, both the proteins and antibodies thereof are useful as blocking agents to prevent or inhibit the initial binding of S. aureus to the wound site or biomaterials. Preferably, the antibody is modified so that it is less immunogenic in the patient to whom it is administered. For example, if the patient is a human, the antibody may be "humanized" by transplanting the complimentarily determining regions of the hybridoma-derived antibody into a human monoclonal antibody as described by Jones et al., *Nature* 321:522-525 (1986) or Tempest et al. *Biotechnology* 9:266-273 (1991).

Medical devices or polymeric biomaterials to be coated with the antibodies, proteins and active fragments described herein include, but are not limited to, staples, sutures, replacement heart valves, cardiac assist devices, hard and soft contact lenses, intraocular lens implants (anterior chamber, posterior chamber or phakic), other implants such as corneal inlays, kerato-prostheses, vascular stents, epikeratophalia devices, glaucoma shunts, retinal staples, scleral buckles, dental prostheses, thyroplastic devices, laryngoplastic devices, vascular grafts, soft and hard tissue prostheses including, but not limited to, pumps, electrical devices including stimulators and recorders, auditory prostheses, pacemakers, artificial larynx, dental implants, mammary implants, penile implants, cranio/facial tendons, artificial joints, tendons, ligaments, menisci, and disks, artificial bones, artificial organs including artificial pancreas, artificial hearts, artificial limbs, and heart valves; stents, wires, guide wires, intravenous and central venous catheters, laser and balloon angioplasty devices, vascular and heart devices (tubes, catheters, balloons), ventricular assists, blood dialysis components, blood oxygenators, urethral/ureteral/urinary devices (Foley catheters, stents, tubes and balloons), airway catheters (endotracheal and tracheostomy tubes and cuffs), enteral feeding tubes (including nasogastric, intragastric and jejunal tubes), wound drainage tubes, tubes used to drain the body cavities such as the pleural, peritoneal, cranial, and pericardial cavities, blood bags, test tubes, blood collection tubes, vacutainers, syringes, needles, pipettes, pipette tips, and blood tubing.

It will be understood by those skilled in the art that the term "coated" or "coating", as used herein, means to apply the protein, antibody, or active fragment to a surface of the device, preferably an outer surface that would be exposed to *S. aureus* infection. The surface of the device need not be entirely covered by the protein, antibody or active fragment.

Immunological and Pharmaceutical Compositions

Immunological compositions, including vaccine, and other pharmaceutical compositions containing the ClfB, SdrC, SdrD, SdrE or consensus or variable sequence amino acid motif, peptides or proteins are included within the scope of the present invention. One or more of the ClfB, SdrC, SdrD, SdrE or consensus or variable sequence amino acid motif, peptides, proteins, or active or antigenic fragments thereof, or fusion proteins thereof can be formulated and packaged, alone or in combination with other antigens, using methods and materials known to those skilled in the art for vaccines. The immunological response may be used therapeutically or prophylactically and may provide antibody immunity or cellular immunity such as that produced by T lymphocytes such as cytotoxic T lymphocytes or CD4+ T lymphocytes.

The immunological compositions, such as vaccines, and other pharmaceutical compositions can be used alone or in combination with other blocking agents to protect against human and animal infections caused by *S. aureus*. In particular, the compositions can be used to protect humans against endocarditis or to protect humans or ruminants against mastitis caused by *S. aureus* infections. The vaccine can also be used to protect canine and equine animals against similar *S. aureus* infections.

To enhance immunogenicity, the proteins may be conjugated to a carrier molecule. Suitable immunogenic carriers include proteins, polypeptides or peptides such as albumin, hemocyanin, thyroglobulin and derivatives thereof, particularly bovine serum albumin (BSA) and keyhole limpet hemocyanin (KLH), polysaccharides, carbohydrates, polymers, and solid phases. Other protein derived or non-protein derived substances are known to those skilled in the art. An immunogenic carrier typically has a molecular weight of at least 1,000 daltons, preferably greater than 10,000 daltons. Carrier molecules often contain a reactive group to facilitate covalent conjugation to the hapten. The carboxylic acid group or amine group of amino acids or the sugar groups of glycoproteins are often used in this manner. Carriers lacking such groups can often be reacted with an appropriate chemical to produce them. Preferably, an immune response is produced when the immunogen is injected into animals such as mice, rabbits, rats, goats, sheep, guinea pigs, chickens, and other animals, most preferably mice and rabbits. Alternatively, a multiple antigenic peptide comprising multiple copies of the protein or polypeptide, or an antigenically or immunologically equivalent polypeptide may be sufficiently antigenic to improve immunogenicity without the use of a carrier.

The ClfB, SdrC, SdrD, SdrE or consensus or variable sequence amino acid motif, peptide, protein or proteins may be administered with an adjuvant in an amount effective to enhance the immunogenic response against the conjugate. At this time, the only adjuvant widely used in humans has been alum (aluminum phosphate or aluminum hydroxide). Saponin and its purified component Quil A, Freund's complete adjuvant and other adjuvants used in research and veterinary applications have toxicities which limit their potential use in human vaccines. However, chemically defined preparations such as muramyl dipeptide, monophosphoryl lipid A, phospholipid conjugates such as those described by Goodman-Snitkoff et al. *J. Immunol.* 147:410-415 (1991) and incorporated by reference herein, encapsulation of the conjugate within a proteoliposome as described by Miller et al., *J. Exp. Med.* 176:1739-1744 (1992) and incorporated by reference herein, and encapsulation of the protein in lipid vesicles such as Novasome™ lipid vesicles (Micro Vescular Systems, Inc., Nashua, N.H.) may also be useful.

The term "vaccine" as used herein includes DNA vaccines in which the nucleic acid molecule encoding ClfB, SdrC, SdrD, SdrE and consensus or variable sequence amino acid motifs, or nucleic acid molecules which are not identical to the disclosed sequences, but which are substantially homologous thereto and encode peptides or proteins which have the same functionality and activities, or antigenic portions thereof in a pharmaceutical composition is administered to a patient. For genetic immunization, suitable delivery methods known to those skilled in the art include direct injection of plasmid DNA into muscles (Wolff et al., *Hum. Mol. Genet.* 1:363 (1992)), delivery of DNA complexed with specific protein carriers (Wu et al., *J. Biol. Chem.* 264:16985 (1989), coprecipitation of DNA with calcium phosphate (Benvenisty and Reshef, *Proc. Natl. Acad. Sci.* 83:9551 (1986)), encapsulation of DNA in liposomes (Kaneda et al., *Science* 243:375 (1989)), particle bombardment (Tang et al., *Nature* 356:152 (1992) and Eisenbraun et al., *DNA Cell Biol.* 12:791 (1993)), and in vivo infection using cloned retroviral vectors (Seeger et al., *Proc. Natl. Acad. Sci.* 81:5849, 1984).

Methods of Administration and Dose of Pharmaceutical Compositions

Pharmaceutical compositions containing the ClfB, SdrC, SdrD or SdrE proteins, nucleic acid molecules, antibodies, or fragments thereof may be formulated in combination with a pharmaceutical carrier such as saline, dextrose, water, glycerol, ethanol, other therapeutic compounds, and combinations thereof. The formulation should be appropriate for the mode of administration. The compositions are useful for interfering with, modulating, or inhibiting S. aureus host cell binding interactions with the extracellular matrix.

Suitable methods of administration include, but are not limited to, topical, oral, anal, vaginal, intravenous, intraperitoneal, intramuscular, subcutaneous, intranasal and intradermal administration.

For topical administration, the composition is formulated in the form of an ointment, cream, gel, lotion, drops (such as eye drops and ear drops), or solution (such as mouthwash). Wound or surgical dressings, sutures and aerosols may be impregnated with the composition. The composition may contain conventional additives, such as preservatives, solvents to promote penetration, and emollients. Topical formulations may also contain conventional carriers such as cream or ointment bases, ethanol, or oleyl alcohol.

In a preferred embodiment, a vaccine is packaged in a single dosage for immunization by parenteral (i.e., intramuscular, intradermal or subcutaneous) administration or nasopharyngeal (i.e., intranasal) administration. The vaccine is most preferably injected intramuscularly into the deltoid muscle. The vaccine is preferably combined with a pharmaceutically acceptable carrier to facilitate administration. The carrier is usually water or a buffered saline, with or without a preservative. The vaccine may be lyophilized for resuspension at the time of administration or in solution.

The carrier to which the protein may be conjugated may also be a polymeric delayed release system. Synthetic polymers are particularly useful in the formulation of a vaccine to effect the controlled release of antigens. For example, the polymerization of methyl methacrylate into spheres having diameters less than one micron has been reported by Kreuter, J., MICROCAPSULES AND NANOPARTICLES IN MEDICINE AND PHARMACOLOGY, M. Donbrow (Ed). CRC Press, p. 125-148.

Microencapsulation of the protein will also give a controlled release. A number of factors contribute to the selection of a particular polymer for microencapsulation. The reproducibility of polymer synthesis and the microencapsulation process, the cost of the microencapsulation materials and process, the toxicological profile, the requirements for variable release kinetics and the physicochemical compatibility of the polymer and the antigens are all factors that must be considered. Examples of useful polymers are polycarbonates, polyesters, polyurethanes, polyorthoesters polyamides, poly (d,l-lactide-co-glycolide-) (PLGA) and other biodegradable polymers. The use of PLGA for the controlled release of antigen is reviewed by Eldridge, J. H., et al. CURRENT TOPICS IN MICROBIOLOGY AND IMMUNOLOGY, 146:59-66 (1989).

One typical dose for human administration is from 0.01 mg/kg to 10 mg/kg. Based on this range, equivalent dosages for heavier body weights can be determined. The dose should be adjusted to suit the individual to whom the composition is administered and will vary with age, weight and metabolism of the individual. The vaccine may additionally contain stabilizers such as thimerosal (ethyl(2-mercaptobenzoate-S) mercury sodium salt) (Sigma Chemical Company, St. Louis, Mo.) or physiologically acceptable preservatives.

Protein-Label Conjugates

When labeled with a detectable biomolecule or chemical, the extracellular matrix-binding proteins described herein are useful for purposes such as in vivo and in vitro diagnostics and laboratory research. Various types of labels and methods of conjugating the labels to the proteins are well known to those skilled in the art. Several specific labels are set forth below. The labels are particularly useful when conjugated to a protein such as an antibody or receptor.

For example, the protein can be conjugated to a radiolabel such as, but not restricted to, $^{32}P$, $^{3}H$, $^{4}C$, $^{35}S$, $^{125}I$, or $^{131}I$. Detection of a label can be by methods such as scintillation counting, gamma ray spectrometry or autoradiography.

Bioluminescent labels, such as derivatives of firefly luciferin, are also useful. The bioluminescent substance is covalently bound to the protein by conventional methods, and the labeled protein is detected when an enzyme, such as luciferase, catalyzes a reaction with ATP causing the bioluminescent molecule to emit photons of light.

Fluorogens may also be used to label proteins. Examples of fluorogens include fluorescein and derivatives, phycoerythrin, allo-phycocyanin, phycocyanin, rhodamine, and Texas Red. The fluorogens are generally detected by a fluorescence detector.

The protein can alternatively be labeled with a chromogen to provide an enzyme or affinity label. For example, the protein can be biotinylated so that it can be utilized in a biotin-avidin reaction, which may also be coupled to a label such as an enzyme or fluorogen. For example, the protein can be labeled with peroxidase, alkaline phosphatase or other enzymes giving a chromogenic or fluorogenic reaction upon addition of substrate. Additives such as 5-amino-2,3-dihydro-1,4-phthalaz-inedione (also known as Luminol™) (Sigma Chemical Company, St. Louis, Mo.) and rate enhancers such as p-hydroxybiphenyl (also known as p-phenylphenol) (Sigma Chemical Company, St. Louis, Mo.) can be used to amplify enzymes such as horseradish peroxidase through a luminescent reaction; and luminogeneic or fluorogenic dioxetane derivatives of enzyme substrates can also be used. Such labels can be detected using enzyme-linked immunoassays (ELISA) or by detecting a color change with the aid of a spectrophotometer. In addition, proteins may be labeled with colloidal gold for use in immunoelectron microscopy in accordance with methods well known to those skilled in the art.

The location of a ligand in cells can be determined by labeling an antibody as described above and detecting the label in accordance with methods well known to those skilled in the art, such as immunofluorescence microscopy using procedures such as those described by Warren and Nelson, *Mol. Cell. Biol.* 7: 1326-1337 (1987).

Screening Methods

The ClfB, SdrC, SdrD and SdrE proteins, or fragments thereof, such as consensus or variable amino acid motifs, are useful in a method for screening materials to identify substances that inhibit *S. aureus* host cell binding interactions with the extracellular matrix. In accordance with the method for screening, the substance of interest is combined with one or more of the ClfB, SdrC, SdrD, or SdrE proteins, or fragments thereof, such as consensus or variable sequence amino acid motif peptides, and the degree of binding of the molecule to the extracellular matrix is measured or observed. If the presence of the substance results in the inhibition of binding, then the substance may be useful for inhibiting *S. aureus* in vivo or in vitro. The method could similarly be used to identify substances that promote *S. aureus* interactions with the extracellular matrix.

The method is particularly useful for identifying substances having bacteriostatic or bacteriocidal properties.

For example, to screen for *S. aureus* agonists or antagonists, a synthetic reaction mixture, a cellular compartment (such as a membrane, cell envelope or cell wall) containing one or more of the ClfB, SdrC, SdrD, SdrE proteins, or fragments thereof, such as consensus or variable sequence amino acid motifs, and a labeled substrate or ligand of the protein is incubated in the presence of a substance under investigation. The ability of the substance to agonize or antagonize the protein is shown by a decrease in the binding of the labeled ligand or decreased formation of substrate product. Substances that bind well and increase the rate of product formation from substrate are agonists. Detection of the rate or level of formation of product from substrate may be enhanced by use of a reporter system, such as a calorimetric labeled substrate converted to product, a reporter gene that is responsive to changes in ClfB, SdrC, SdrD, SdrE or consensus or variable amino acid sequence motifs' nucleic acid or protein activity, and binding assays known to those skilled in the art. Competitive inhibition assays can also be used.

Potential antagonists include small organic molecules, peptides, polypeptides and antibodies that bind to ClfB, SdrC, SdrD, SdrE or consensus or variable sequence amino acid motifs' nucleic acid molecules or proteins and thereby inhibit their activity or bind to a binding molecule (such as fibrinogen) to prevent the binding of the ClfB, SdrC, SdrD, SdrE or consensus or variable sequence amino acid motifs' nucleic acid molecules or proteins to the binding molecule. For example, a compound that inhibits ClfB, SdrC, SdrD, SdrE or consensus or variable sequence amino acid motifs' activity may be a small molecule that binds to and occupies the binding site of the ClfB, SdrC, SdrD, SdrE or consensus or variable sequence amino acid motif peptide or protein, thereby preventing binding to cellular binding molecules. Examples of small molecules include, but are not limited to, small organic molecules, peptides or peptide-like molecules. Other potential antagonists include antisense molecules. Preferred antagonists include compounds related to and variants or derivatives of ClfB, SdrC, SdrD, SdrE or consensus or variable sequence amino acid motif peptides or proteins.

The nucleic acid molecules described herein may also be used to screen compounds for antibacterial activity.

Therapeutic Applications

In addition to the therapeutic compositions and methods described above, the ClfB, SdrC, SdrD, SdrE or consensus or variable amino acid motifs, peptides or proteins, nucleic acid molecules or antibodies are useful for interfering with the initial physical interaction between a pathogen and mammalian host responsible for infection, to mammalian extracellular matrix proteins on indwelling devices or to extracellular matrix proteins in wounds they are further useful to block ClfB, SdrC, SdrD, SdrE, or active fragments thereof, including consensus or variable amino acid motifs, peptide or protein-mediated mammalian cell invasion. In addition, these molecules are useful to mediate tissue damage and to block the normal progression of pathogenesis in infections.

S. aureus Detection Kit

The invention further contemplates a kit containing one or more ClfB, SdrC, SdrD, SdrE proteins, peptides, or active fragments thereof, including consensus or variable amino acid motif-encoding nucleic acid probes. These probes can be used for the detection of S. aureus or S. aureus extracellular matrix-binding proteins in a sample. Such a kit can also contain the appropriate reagents for hybridizing the probe to the sample and detecting bound probe.

In an alternative embodiment, the kit contains one or more ClfB, SdrC, SdrD, or SdrE proteins, peptides or consensus or variable amino acid motif-specific antibodies, which can be used for the detection of S. aureus organisms or S. aureus extracellular matrix-binding proteins in a sample.

In yet another embodiment, the kit contains one or more ClfB, SdrC, SdrD or SdrE-proteins, or active fragments thereof, such as the consensus or variable sequence amino acid motifs, which can be used for the detection of S. aureus organisms or S. aureus extracellular matrix-binding antibodies in a sample.

The kits described herein may additionally contain equipment for safely obtaining the sample, a vessel for containing the reagents, a timing means, a buffer for diluting the sample, and a calorimeter, reflectometer, or standard against which a color change may be measured.

In a preferred embodiment, the reagents, including the protein or antibody, are lyophilized, most preferably in a single vessel. Addition of aqueous sample to the vessel results in solubilization of the lyophilized reagents, causing them to react. Most preferably, the reagents are sequentially lyophilized in a single container, in accordance with methods well known to those skilled in the art that minimize reaction by the reagents prior to addition of the sample.

EXAMPLES

The present invention is further illustrated by the following non-limiting examples, which are not to be construed in any way as imposing limitations upon the scope thereof. On the contrary, it is to be clearly understood that resort may be had to various other embodiments, modifications, and equivalents thereof which, after reading the description herein, may suggest themselves to those skilled in the art without departing from the spirit of the present invention.

Example 1

Gene Cloning, Sequencing and Expression

A fibrinogen-binding protein gene, designated clfB, was isolated, cloned and sequenced as follows:

Bacterial Strains and Growth Conditions

The E. coli and S. aureus strains used for the cloning and sequencing of clfB are listed in Table 1, below. Escherichia coli was routinely grown on L-broth or agar. S. aureus was routinely grown on trypticase soy broth (Oxoid) or agar. The following antibiotics were incorporated into media where appropriate: ampicillin (Ap), 100 µg/ml; tetracycline (Tc), 2 µg/ml; chloramphenicol (Cm), 5 µg/ml; erythromycin (Em) 10 µg/ml.

| Bacterial Strain | Genotype | Relevant properties/ Use in present study | Source/reference |
|---|---|---|---|
| E. Coli | | | |
| C600 | F⁻, lacY1, leuB6, supE44, thi-1, thr-1, tonA21 | Propagation of lambda recombinants | Appleyard, Genetics 39: 440-452 (1954) |
| DH5α | F⁻, ø80dlacZM15, deoR, | Recombination deficient, host | Hanahan et al, J. Mol. |

| Bacterial Strain | Genotype | Relevant properties/ Use in present study | Source/reference |
|---|---|---|---|
| | endA1, gyrA96, hsdR17, (r$_{k-}$, m$_{k+}$), (lacZYA-argF) U169, recA1, relA1, supE44, thi-1 | strain for plasmids and for DNA sequencing | Biol. 166: 557-580 (1983) |
| JM101 | supE, thi-1, (lac-proAB), [F' traD36, proAB, lacI$^q$M15] | Host strain for plasmid bank and for sequencing | Stratagene (La Jolla, CA) |
| LE392 | F$^-$, (r$_{k-}$, m$_{k+}$), galK3, galT22, hsdR574, lacY1 or (lacIZY)6, metB1, supE44, supF58, trpR55 | Propagation of lambda recombinants | Promega Corp. (Madison, WI) |
| XL-1 Blue | | [F' proAB, lacI$^q$ZM15. Tn10(tc$^r$)], endA1, gyrA96, hsdR17, lac, recA1, relA1, supE44, thi-1 | Propagation of plasmids Stratagene |
| *S. aureus* | | | |
| Newman | | Strong adherence to fibrinogen | NCTC 8178; Duthie and Lorenz, J. Gen. Microbiol. 6: 95-107 (1952) |
| DU5876 | | clfA2::Tn917, Em$_r$ | McDevit et al., Mol. Microbiol. 11: 237-248 (1994) |
| DU5943 | | clfB::Tc$_r$, Tc$_r$ | described herein |
| DU5944 | | clfAclfB, Em$_r$, Tc$_r$ | described herein |
| DU5874 | | spa:: Tc$_r$ | Protein A-defective mutant of NewmanMcDevitt et al., Mol. Microbiol. 16: 895-907 (1995) |
| Δ map | | | McDevitt, unpublished |
| 8325-4 | | NCTC 8325 cured of prophages | Novick, Virology 33: 155-166 (1967) |
| ISP546 | | agr::Tn551 | 8325-4 agrBrown and Pattee, Infect. Immun. 30: 36-42 (1980) |
| RN4220 | | Restriction deficient derivative of 8325-4 | Kreiswirth et al., Nature 305: 709-712 (1983) |
| V8 | | Classic V8 protease producer, produces PV leukocidin | ATCC 27733 |
| Cowan 1 | | Classic protein A producer, adheres well to fibrinogen and fibronectin | ATCC 12598 |
| RN4282 | | TSST-1 producer | Kreiswirth et al., 1983 (as 3-14) |
| Phillips | | Collagen binding strain | Patti et al., Infect. Immun. 62: 152-161 (1994) |
| V13 | | Septicaemia isolate | O'Reilly et al., Mol. Microbiol. 4: 1947-1955 (1990) |
| GH13 | | Methicillin resistant | Poston and Li Saw Hee, J. Med. Microbiol. 34: 193-201 (1991) |
| P1 | | Rabbit virulent strain | Sherertz er al., J. Infect. Dis. 167: 98-106 (1993) |
| M60 | | Bovine mastitis isolate | Anderson, Zentralbl Bakteriol Parasitenkd Infektionskr Hyg Abt. 1 Orig Reihe A 5(Suppl.): 783-790 (1976) |

DNA Manipulation

Unless otherwise specified, DNA manipulations were done according to standard methods as described by Ausubel et al., CURRENT PROTOCOLS IN MOLECULAR BIOLOGY. New York, John Wiley and Sons (1987) and Sambrook et al., MOLECULAR CLONING: A LABORATORY MANUAL, 2nd ed. Cold Spring Harbour, N.Y., Cold Spring Harbour Laboratory Press (1989). Enzymes for DNA manipulation were obtained from New England Biolabs (Beverly, Mass.) and Promega (Madison, Wis.), and used as directed by the manufacturer. Genomic DNA from *S. aureus* Newman was prepared according to methods of Muller et al., *Infect.*

*Immun.* 61:551-558 (1993). Smaller scale preparations were made by lysing cells in phosphate buffered saline (PBS) containing 12 µg/ml lysostaphin and 20 mM EDTA (ethylenediaminetetraacetic acid), followed by protease K treatment (500 µg/ml in 1% SDS) for 1 hour at 60° C., extraction with phenol and chloroform, and dialysis against 10 mM Tris HCl, pH 8.0, 1 mM EDTA. Plasmid DNA was prepared from *S. aureus* according to the method of Vriesema et al., *Appl. Environ. Microbiol.* 62:3527-3529 (1996). *E. coli* plasmid DNA for use in polymerase chain reaction (PCR) and sequencing was routinely made by the modified alkaline lysis method of Feliciello and Chinali, *Anal. Biochem.* 212:394-401 (1993), and occasionally by large scale isolation and dye-buoyant density centrifugation. Screening of *E. coli* transformants for chimeric plasmids was routinely done by the rapid colony lysis procedure of Le Gouill and Dery, *Nucl. Acids Res.* 19:6655 (1994).

Cloning of Repeat-Containing Loci

A genomic library of *S. aureus* Newman was constructed in the LambdaGEM-12 replacement vector (obtained as prepared XhoI half-site arms from Promega Madison, Wis.)) according to the manufacturer's instructions. Oligonucleotide probes specific for regions A and R of *S. aureus* Newman were made by polymerase chain amplification of these regions from the cloned gene on pCF14, as described by McDevitt and Foster, *Microbiology* 141:937-943 (1995), and random-primer labeled with [alpha-$^{32}$P]dATP using the Promega Prime-a-Gene™ kit (Promega). The bank was screened by Southern blotting, using an overnight hybridization temperature of 65° C. Selected clones were single plaque purified twice, and plate-lysate stocks made for storage and for inoculation of liquid cultures for the large-scale preparation of phage for DNA isolation.

A 3.87-kb HindIII fragment containing homology to region R DNA was cloned from the genome of *S. aureus*. HindIII-cleaved genomic DNA in the range of 3-4 kb was excised from an agarose gel, purified, and ligated to the pBluescript cloning vector. Plasmids were transformed into *E. coli* JM101 and identification of a recombinant *E. coli* containing a region R DNA insert was identified by PCR screening. PCR products were generated using primers specific for region R DNA. Individual colonies within a pool producing a positive PCR reaction were then analyzed for their potential to generate a PCR product. One transformant, pC1, was identified and found to contain the 3.87-kb fragment with homology to region R.

DNA Sequencing

The DNA sequence of clfB was obtained from pA1-1EX, a plasmid containing a fragment subcloned from recombinant phage A1-1 into pGEM 7Z (f)+. Nested deletions were made using the Erase-a-Base™ Kit (Promega). The Flash Dye Primer Sequencing Kit (Genpak) was used for sequencing in a Model 373A sequencing system (Applied Biosystems, Foster City, Calif.). Confirmatory sequencing in the forward direction was carried out. Double stranded sequencing of sdrD and sdrE was done on the subclones pEJ1, pEJ2 and pEJ3, containing fragments subcloned from recombinant phage A6-2 in pGEM 7Z (f)+, by nested deletions and primer walking. Automated sequence analysis of sdrC and the 5' end of sdrD on plasmid clone pC1 was performed. Sequence analysis was performed on both strands by primer extension to known sequences.

Screening of *S. aureus* Strains for clfB Homologues

A probe specific for the region A-encoding portion of clfB was made by excising a 614 by internal AccI fragment from pA1-1EX, purifying from an agarose gel using the GENECLEAN II™ kit (BIO 101 Inc., La Jolla, Calif.), and labeling with [alpha-$^{32}$P]dATP as described in FIG. 2. A probe was similarly made to distal regions of the gene (encoding region R, the wall and membrane-spanning regions, and about 100 by of downstream DNA), using a 1.2 kb BamHI fragment from pA1-1EX. HindIII digests of genomic DNA from a panel of strains were Southern blotted and screened using these probes.

Expression of clfB Region A

Region A (encoding residues S45 to N542) of clfB was amplified from pA1-1EX by PCR using the following primers:

```
                                              (SEQ ID NO: 15)
Forward:   5' CGAGGATCCTCAGGACAATCGAACGATACAACG 3'

(SEQ ID NO: 16)
Reverse:   CGAGGTACCATTTACTGCTGAATCACC 3'.
```

Cleavage sites for BamHI and KpnI (underlined) were appended to the 5' ends of the respective primers to introduce these sites into the product and facilitate its cloning into expression vectors. The forward primer was subsequently found to include a single base mismatch (G, underlined), changing an E codon to a G codon. Reaction mixtures (50 µl) contained 2 mM dNTPs, 1.5 mM MgCl.sub.2, 1 ng pA1-1EX, 50 nM primers and 1.25 U Taq polymerase in standard Promega (Madison, Wis.) Taq reaction buffer. Amplification proceeded in a Perkin Elmer Cetus (Foster City, Calif.) thermocycler with an initial denaturation at 94° C. for 4 minutes, followed by 30 cycles with denaturation at 94.degree. C. for 1 minute, annealing at 50° C., and extension at 72° C. for 1.5 minutes, with minimum heating and cooling between steps. The final extension was for 10 minutes. A single product was obtained, which was purified using the Wizard™ PCR purification kit (Promega). The product was initially cloned into the His-tag expression vector pQE30. However, because high-level expression was not obtained in this system, the product was recloned into an alternative vector, the GST fusion vector pGEX-KG, between the BamHI and HindIII sites. The recombinant protein was recovered from lysates by affinity chromatography on glutathione-sepharose (GST Gene Fusion System™ Pharmacia, Piscataway, N.J.) and from the glutathione-S-transferase fusion partner by thrombin cleavage.

Cloning of Repeat Carrying Loci

A library of *S. aureus* Newman genomic DNA was made using the replacement lambda vector LambdaGEM™-12. About 10 000 plaques were screened using the region R-specific probe. Of the 60 positive plaques retained, 26 were purified and counter-screened with a clfA region A-specific probe. One plaque hybridized with the latter, indicating that it contained the clfA gene; of the remaining, non-hybridizing plaques, three were selected at random, and the DNA isolated. The DNA was cut with several restriction enzymes and analyzed by Southern blotting using the region R probe. Clones A1-1 and A2-3 appeared to contain overlapping sequences. Restriction mapping and Southern blotting indicated that these clones contained a single region R homologue. Clone A6-2 was found to contain three region R homologues, since cleavage with EcoRV yielded three fragments hybridizing to the region R probe.

Clone A1-1 was chosen for more detailed study, as the hybridizing fragment was slightly longer than in clone A2-3. A 7.4 kb EcoRI fragment containing the repeat region was subcloned from lambda clone A1-1 into plasmid pGEM 7Z f(+) to generate plasmid pA1-1E. This insert was reduced to approximately 3 kb by excision of a 4.4 kb XbaI segment to form pA1-1EX as shown in FIGS. 2 and 3.

Clone A6-2 was restriction mapped and fragments subcloned into plasmid vectors for sequencing as shown in FIG. 4. Southern blotting with the region R probe and preliminary sequencing suggested that there were three tandemly arrayed genes carrying region R encoding sequences. On A6-2 there were two complete ORFs, sdrD and sdrE, and one incomplete ORF, sdrC.

The two complete ORFs were sequenced on fragments subcloned from lambda A6-2 into plasmid vectors pGEM7Z f(+) (subclones pEJ1 and pEJ2) and pBluescript KS+(subclone pEJ3). sdrC was cloned separately from *S. aureus* genomic DNA. A 3.87-kb HindIII fragment of strain Newman was cloned directly into plasmid pBluescript KS+, generating clone pC1 (FIG. 4). This clone, containing a region R DNA insert, was identified by PCR screening. The sequence of sdrC and the 162 by at the 5' end of sdrD were determined from pC1.

Plasmid pA1-1EX, carrying the clfB gene, was deposited at the National Collections of Industrial and Marine Bacteria on Oct. 13, 1997 under the Accession No. 40903. Plasmid pC1, carrying the gene for sdrC, was deposited at the National Collections of Industrial and Marine Bacteria under the Accession No. NCIMB 40902 on Oct. 13, 1997 and a recombinant lambda phage A6-2, carrying the sdrD and sdrE genes, was deposited at the NCIMB on Oct. 13, 1997 under the Accession No. NCIMB 40904. All deposits comply with the terms of the Budapest Treaty.

Features of ClfB

The translated open reading frame (ORF) contained within pA1-1EX is shown in FIG. 5. The ORF shows features reminiscent of secreted proteins of Gram positive cocci. Although the entire ORF is shown in FIG. 5, the start codon is unlikely to be the N codon. There is no ATG codon at the 5' end of the ORF. However, GTG and TTG are occasionally used as translational start codons in *S. aureus*, although methionine is the actual amino acid residue inserted, e.g., the fibronectin binding proteins (GTG), and protein A (TTG). The first TTG codon (L) may well be the initiation codon, as a possible ribosome binding site, GGAG, is suitably located upstream, starting at position-12. The N-terminal 44 amino acid residue region thus predicted has properties similar to signal sequences of secreted proteins of Gram positive cocci, i.e., an initial stretch of 19 mostly polar residues, with an overall positive charge, followed by 18 neutral residues with a high content of hydrophobic residues, and finally a short stretch of mainly polar residues with a good consensus cleavage site, AQA-S.

If the above prediction of the signal sequence is correct, region A of ClfB is 498 residues long, and shows 26.3% residue identity with the equivalent region in ClfA, or 44.4% homology when conservative substitutions are included. The most marked stretch of amino acid similarity between ClfA and ClfB occurs between residues 314-329 (ClfA) and 304-319 (ClfB), with 7 identical and 5 conserved residues. In ClfA, the stretch overlaps the C-terminal half of a putative $Ca^{2+}$ binding loop, EF hand I, required for fibrinogen binding as shown in FIG. 6. The sequence DYSNS (SEQ ID NO: 11), which obeys the consensus for the N-terminal moiety of a MIDAS motif, occurs a short distance upstream. Accordingly, the downstream sequence was inspected for D and T residues to complete the motif. D and T occur frequently throughout the protein, and T 339 is suitably located, 63 residues downstream. However, the consensus would require a D residue 14-23 residues downstream from the T, and in the present case, the nearest D residues are 9 or 28 residues away (D 348 and D 367).

At the C-terminal end of region A, a prominent proline-rich region occurs (21/42 residues are P; as shown in FIG. 5). There is a 14-residue repeat within this sequence. The DNA encoding the P-rich repeats is highly conserved. Of the three base substitutions, only one results in an amino acid replacement, a conservative substitution of S for T.

Region R is somewhat shorter in clfB than in clfA (272 residues instead of 308). The region R encoding sequence comprises the 18-bp consensus repeat observed in the equivalent part of clfA.

Following region R is a short stretch of predominantly hydrophilic residues, containing the distinctive LPETG (SEQ ID NO: 22) motif near its C-terminal end, presumably the cell sorting signal. The C-terminal region of the predicted protein shows strong homology with the corresponding region in ClfA, with an initial stretch of mostly hydrophobic residues and a final stretch rich in positively charged residues, reminiscent of membrane spanning and anchoring domains, respectively. The general organization of ClfA and ClfB is compared in FIG. 1.

A putative transcription termination signal occurs 3' to clfB. No open reading frames occur within 260 by 5' or 200 by 3', suggesting that the gene is not part of an operon.

Features of SdrC, SdrD and SdrE

The DNA sequences and the translated amino acid sequences of sdrC, sdrD and sdrE are shown in FIGS. 7, 8 and 9. Each predicted protein has a putative signal sequence, an approximately 500 residue "region A" with limited homology to region A of ClfA (see FIG. 10), variable numbers of B repeats, an SD repeat containing region R, an LPXTG (SEQ ID NO: 14) cell wall sorting motif, a hydrophilic membrane anchor, and positively charged residues at the extreme C terminus.

The organization of the five region R containing proteins is shown in FIG. 10. The A regions of SdrC, SdrD and SdrE have limited sequence similarity to each other and to those of ClfA and ClfB as shown in FIG. 11. Alignments of those sequences more strongly conserved between all five proteins are shown in FIG. 12. The consensus motif TYTFTDYVD (SEQ ID NO: 18) overlaps the EF hand 1 motif of ClfA (alignment 2, FIG. 12). This region of ClfA has been shown to be of crucial significance in its ligand (fibrinogen) binding activity as described by O'Connell et al., *J. Biol. Chem.*, 273:6821-6829 (1998), and may also be of importance in the biological activity of the new proteins.

The three proteins SdrC, SdrD and SdrE form a separate subgroup of region R containing proteins: in addition to regions R and A they contain variable numbers of B repeats, located between region A and region R. The B repeats are 110-113 amino acids long and show considerable similarity (alignment 5, FIG. 12). The repeats SdrC B2, SdrD B5 and SdrE B3 adjacent to region R are 93-95% identical. There is a strongly conserved EF hand near the N-terminal end of each repeat.

clfB Homologues in other *S. aureus* Strains

Nine strains of *S. aureus* were screened for the clfB gene by Southern blotting. Genomic DNA was cut to completion with HindIII, and probed with an internal 0.6 kb AccI fragment of the region A coding sequence of clfB, shown in FIG. 2. The probe recognized a single HindIII fragment varying from 2 to 3 kb in length in all nine strains, indicating that each possesses a single clfB allele. A probe made from the region R and distal regions of clfB recognized an identical band in all strains, indicating that the clfB homologues in other strains also contain region R.

Expression of clfB

Figure 13:
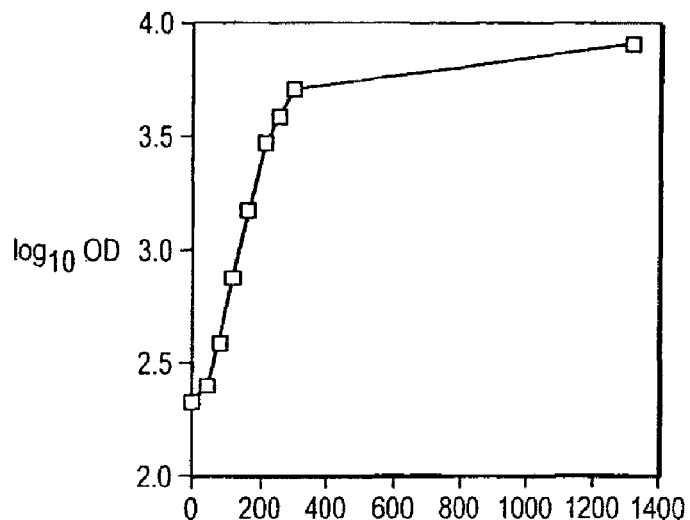
FIG. 13 is a time-course graph of ClfB expression in *S. aureus* Newman versus time, monitored by Western blotting. Shake flask cultures were sampled at specific time intervals. A standard number of cells was used to prepare lysates.

The portion of clfB encoding region A was amplified by PCR using primers incorporating suitable 5' restriction sites, and cloned into the *E. coli* expression vector pGEX-KG. A protein of 94.3 kDa was detected in lysates of induced bacteria. The GST-ClfB fusion protein was immobilized on a glutathione sepharose affinity column, cleaved with thrombin, and examined by SDS-PAGE. The predominant band was 42 kDa, whereas the calculated molecular weight of region A is 54 kDa. This protein was used to raise antibody in rabbits, to probe Western blots of cell lysates made from strain Newman grown under a variety of conditions, as described below. The antibody failed to detect any antigens in lysates made from plate cultures, statically grown broth cultures, or shake-flask cultures grown to stationary phase. A single 124-kDa band was detected in lysates made from exponential phase shake-flask cultures of strain Newman and derivatives. If it is assumed that processing removes the signal sequence and the C-terminal portion of the protein from the last G of the LPETG (SEQ ID NO: 22), the predicted molecular weight of ClfB is 88.3 kDa. In a time-course of ClfB production by a shake-flask culture of strain Newman, the ClfB protein was most abundant in the early exponential phase and showed a sharp decline toward the end of exponential phase, after which levels became undetectable. The results of the time-course study are shown in FIG. 13.

Example 2

Production of Anti-ClfB Serum

Antibodies to recombinant region A were raised in two young New Zealand white rabbits (2 kg) showing no prior reaction with *E. coli* or *S. aureus* antigens in Western blots. Injections, given subcutaneously, contained 25 µg of the antigen, diluted to 500 ml in phosphate buffered saline (PBS) emulsified with an equal volume of adjuvant. The initial injection contained Freund's complete adjuvant; the two to three subsequent injections, given at two-week intervals, contained Freund's incomplete adjuvant. When the response to the recombinant protein was judged adequate, the rabbits were bled, serum recovered, and total IgG purified by affinity chromatography on protein A sepharose (Sigma Chemical Co., St. Louis, Mo.).

SDS-PAGE and Western Blotting

Samples were analyzed by SDS-PAGE in 10 or 12% acrylamide gels. Isolated proteins and *E. coli* cell lysates were prepared for electrophoresis by boiling for five minutes in denaturation buffer. For *S. aureus*, cells were suspended to an $OD_{600}$ of 40 units in 100 mM PBS containing 10 mM EDTA. To each 500 µl sample, 40 µl protease inhibitors (Complete™ cocktail, Boehringer Mannheim, Indianapolis, Ind.), 5 µl each of DNAse and RNAse (from 10 mg/ml stocks, Sigma Chemical Co.), and 60 µl of a 2 mg/ml lysostaphin stock (Ambicin L™ recombinant lysostaphin, Applied Microbiology Inc., Tarrytown, N.Y.) were then added and the suspension incubated in a 37° C. water bath until it cleared. The samples were then processed as usual. Gels were stained with Coomassie blue or transferred to Nytran™ membrane by Western blotting in the Bio-Rad Semidry™ system (Bio-Rad Laboratories, Richmond, Calif.). For detection of native ClfB in *S. aureus*, blots were processed using the BM Chemiluminescence Detection System™ (POD) of Boehringer Mannheim, according to the manufacturer's instructions. Primary anti-ClfB antibody was used at a {fraction (1/1000)} dilution, for a two hour incubation at room temperature. Protein A conjugated with horse radish peroxidase (Sigma Chemical Co.) was used to detect bound antibody, diluted {fraction (1/2000)} for a one hour incubation at room temperature. Blots requiring less sensitivity were treated in a similar way, except that 5% skim milk was used as a blocking agent, and the blots were developed using chloronaphthol and hydrogen peroxide.

To determine whether ClfB is cell wall-associated, whole cells from an exponential phase culture were treated with lysostaphin in buffer supplemented with 30% raffinose to stabilize the protoplasts. The protoplasts were harvested, and the protoplasts and supernatant analyzed separately by Western blotting. ClfB protein was detected only in the supernatant, indicating that all ClfB was cross-linked to the peptidoglycan, and could be released by lysostaphin without disruption of the protoplast.

ClfB expression was enhanced by growth in rich media, such as tryptone soy broth or brain heart infusion.

Several *S. aureus* strains known to contain clfB alleles were screened for ClfB production by Western blotting. Cultures were harvested in early exponential phase to maximize expression. Of the nine strains examined, 83254, RN4282, and V13 expressed immunoreactive antigens of similar size and intensity to that of Newman, whereas strains GH13 and P1 had very weak bands of this size. Strains P1, Cowan and M60 expressed smaller immunoreactive antigens which may be degradation products. Strains V8 and Phillips expressed no detectable ClfB protein. Strain RN4220, which was derived from 8325-4, expressed exceptionally high levels of ClfB.

Example 3

Immunoassay for ClfB using Biotinylated Recombinant ClfB Region A

The DNA encoding region A of clfB (encoding residues S45 to N542) was amplified from genomic DNA of *S. aureus* Newman using the following primers:

```
                                        (SEQ ID NO: 17)
Forward: 5' CGAAAGCTTGTCAGAACAATCGAACGATACAACG 3'

(SEQ ID NO: 16)
Reverse: 5' CGAGGATCCATTTACTGCTGAATCACC 3'
```

Cleavage sites for HindIII and BamHI (underlined) were appended to the 5' ends of the respective primers to facilitate cloning of the product into the His-tag expression vector pV4. Cloning employed *E. coli* JM101 as a host strain. The recombinant region A was purified by nickel affinity chromatography.

Enzyme Linked Immunosorbent Assay (ELISA)

Immulon 1™ plates (Dynatech™, Dynal, Inc., Great Neck, N.Y.) were coated overnight with 100 µl of 10 µg/ml human fibrinogen (Chromogenix). They were then blocked with 200 µl of 5 mg/ml bovine serum albumin (BSA) for one hour. The plates were then incubated for three hours with 100 µl biotinylated ClfB (His-tag recombinant region A) diluted to 0.1-10 µg/ml. They were then given three five-minute washes with PBS containing 0.02% Tween 20 and 1 mg/ml BSA. The plates were then incubated for one hour with 100 µl of a 1/10 000 dilution of streptavidin conjugated with alkaline phosphatase (Boehringer Mannheim, Indianapolis, Ind.), and washed as before. The plates were then developed for 30 minutes at 37° C. with 100 µl of 1 M diethanolamine, pH 9.8, containing 1 mg/ml p-nitrophenyl phosphate (Sigma Chemical Co.). Plates coated with BSA only were used as negative controls. The absorbance was measured at 405 nm.

Western Affinity Blotting

A 20 μg quantity of human fibrinogen (Chromogenix) was subjected to SDS-PAGE on a 15% acrylamide gel for two hours. Proteins were transferred to nitrocellulose at 100 V for two hours. The membrane was blocked overnight in PBS containing 10% nonfat dry milk. The blot was then incubated with 2.5 μg/ml biotinylated ClfB (His-tag recombinant region A) for one hour with shaking, the biotinylation being performed with EZ link-sulfo-NHS-LC-Biotin™ (Pierce, Rockford, Ill.). The blot was then given three five-minute washes in PBS containing 0.1% Tween 20. The blot was then incubated for one hour with avidin conjugated with horseradish peroxidase (Boehringer Mannheim) at a 1/200,000 dilution. The blot was then washed as before, and developed using the enhanced chemiluminescence system of Amersham (Little Chalfont, Bucks, UK). The band profile was compared with that obtained by subjecting fibrinogen to SDS-PAGE and Coomassie Blue staining.

In a Western affinity blot, in which biotinylated purified ClfB region A was used to probe blotted fibrinogen, a comparison with a lane of stained fibrinogen indicated that ClfB bound the alpha and beta-chains of fibrinogen. No bands were seen when ClfB was omitted. This experiment shows an important difference with ClfA, which is known to bind to the gamma-chain of fibrinogen.

Example 4

Mutagenesis of clfB

An insertion mutation in clfB was created by introducing a fragment containing a Tc resistance marker into the middle of the gene on pA1-1EX as shown in FIG. 3. The 2.35-kb HindIII fragment from pT181 was filled in with Klenow enzyme, and blunt-end ligated into the HpaI site of pA1-1EX. Plasmid pTS2, with temperature sensitive replication and a $Cm^r$ marker, was cloned into this construct at the SmaI site by cleaving with AvaI. This cloning step was carried out in *E. coli*, and transformants were selected on Ap and incubated at 30° C. to avoid selection of revertants to temperature independence. The plasmid was then purified and transformed into *S. aureus* RN4220 by electroporation and $Tc^r$ transformants selected at 30° C. Five independent broth cultures grown at 30° C. were diluted 1/100 in fresh medium without antibiotics, and grown at 42° C. for six hours or 18 hours. The cultures were then diluted 1/100 and incubated at 42° C. for another time period. Six such dilutions and incubations were made, by which time Tc resistance had declined to approximately 1/1000 colony forming units (CFU). The cultures were then diluted to give approximately 100 CFU per plate on medium containing Tc, and incubated overnight at 37° C. Colonies which were $Tc^r$ but $Cm^s$ were presumed to have undergone a double crossover event between the plasmid and host genome, leading to replacement of the wild-type gene with the mutated one, with subsequent loss of the plasmid. Five hundred colonies were screened per culture. Eleven presumptive mutants were isolated from four of the five cultures. Four representative mutants were selected and genomic DNA isolated. Mutant DU5944, deficient in both clfA and clfB, was constructed by transducing clfA2::Tn917 from strain DU5876 into clfB mutant DU5943, selecting for $Em^r$.

To determine whether mutations known to affect exoprotein expression influenced clfB, strain 8325-4 and the agr mutant ISP546 were compared. No significant differences in the level or dynamics of ClfB expression were noted.

To determine the role of ClfB in bacteria-fibrinogen interactions, a clfB mutant of strain Newman was constructed by allele replacement as shown in FIG. 2. Genomic DNA of the mutant was digested with BamHI and subjected to Southern blotting with a labeled 1.3 kb HpaI fragment from plasmid pA1-1E containing the 5' half of clfB and about 150 by of upstream sequence. A single band hybridized in each case, but as expected, the band was 2.35 kb longer in the mutant than in the wild-type. The mutation was initially isolated in RN4220 and then transduced into strain Newman, forming strain DU5943.

Overexpression of ClfB and Complementation of clfB Mutation

Overproduction of ClfB was enabled by subcloning a SmaI fragment containing the clfB gene and 500 by of upstream DNA from pA1-1E into the high copy number shuttle plasmid pCU1. The construct was then transformed into strain RN4220 and transduced into strain Newman Transductants were selected on Cm. Southern and Western blotting confirmed that the high copy number was maintained in strain Newman, and that ClfB was produced at higher than wild-type levels, indicating that the upstream DNA contained the promoter necessary for expression of the clfB gene. Transduction of the construct into clfB mutants restored ClfB synthesis to higher than wild-type levels. The construct was also transduced into clfAclfB double mutants for use in complementation studies.

To create a clfAclfB double mutant, a clfA::Tn917 mutation was transferred by transduction from strain DU5876 into the clfB::$Tc^r$ mutant DU5943, forming DU5944. The wild-type clfB gene was cloned into shuttle plasmid pCU1 to give plasmid pA1-1EA, which was introduced into the clfAclfB mutant by transduction to test complementation. Western blotting with anti-ClfB serum showed that the ClfB protein was missing in mutant DU5943. It was expressed at a higher level than the wild-type in mutants carrying the complementing plasmid PA1-1EA, indicating overexpression of the protein due to gene dosage effect.

Example 5

ClfB Binding Assays

Clumping Assays

The role of ClfB in binding of *S. aureus* cells to soluble fibrinogen was investigated in clumping assays. Clumping assays were carried out in Sarstedt™ flat-bottomed multiwell test plates, using 50-μl volumes of human fibrinogen (Calbiochem Corp. (San Diego, Calif.) plasminogen free, >95% pure), diluted serially two-fold in PBS from a starting concentration of 1 mg/ml. *S. aureus* cultures were washed once in PBS, resuspended to a final $OD_{600}$ of 6, and 20 μl added to each well. Control wells contained PBS 30 only. The plates were agitated briskly for five minutes and visually examined for clumping. The clumping titer was the lowest concentration of fibrinogen at which clumping occurred. The results are set forth in Table 2, below. Results are the mean of concurrent duplicate assays.

TABLE 2

Clumping titres of S. aureus Newman and mutants from different culture phases

| Strain | Clumping titer, µg/ml fibrinogen phase | Stationary Exponential phase |
|---|---|---|
| Wild-type | 0.98 | 0.98 |
| clfA | 3.91 | >1000.00 |
| clfB | 1.95 | 0.98 |
| clfA clfB | >1000.00 | >1000.00 |
| clfA clfB (pA1-1EA; clfB$^+$) | 2.93 | 250.00 |

The clumping titers of clfA and clfB single mutants were very similar to wild-type when exponential phase cultures were used. However, the double clfAclfB mutant failed to form clumps, even at the highest fibrinogen concentration. In contrast, the double mutant carrying the wild-type clfB gene on pA1-1EA formed clumps with almost the same avidity as the wild-type. These data show unambiguously that ClfB is a clumping factor.

The difference in clumping titer between the single mutants was much greater when stationary phase cultures were used, where only ClfA is present on cells. The wild-type strain and single clfB mutant had identical titers. The single clfA mutant failed to clump, and was thus indistinguishable from the double mutant. Interestingly, there was a slight restoration of clumping when the double mutant was complemented with the overexpressed clfB gene. This probably reflects over expression of the protein.

Plate Adherence Assays

To determine whether ClfB can promote bacterial attachment to immobilized fibrinogen, strains were tested for fibrinogen binding in a microtiter plate adherence assay. Binding of cells to fibrinogen immobilized on plates was measured by the assay of Wolz et al., *Infect. Immun.* 64:3142-3147 (1996). Fibrinogen was diluted in carbonate buffer (15 mM Na$_2$CO$_3$, 35 mM NaHCO$_3$, 3.2 µM NaN$_3$, pH 9.6) and 100 µl used to coat 96-well flat-bottomed ELISA plates (Immulon 4™ Dynatech) overnight at 4° C. Control wells contained carbonate buffer only. After washing in 150 mM NaCl, 0.05% Tween 20™ surfactant, the plates were blocked for one hour at 37.degree. C. in 1% BSA, 0.05% Tween in PBS. After washing as before, 100 µl of a cell suspension (OD$_{600}$ of 0.4 in PBS) was added, and the plates incubated for two hours at 37° C. After gentle washing by hand, adherent cells were fixed by adding 100 µl of 25% aqueous formaldehyde, and incubating at room temperature for at least 30 minutes. The plates were then washed gently once more, stained with crystal violet, washed again, and the plates read by ELISA reader at 570 nm. To avoid inter-assay variation, experiments were designed so that a single plate provided a complete set of results.

Figure 15:
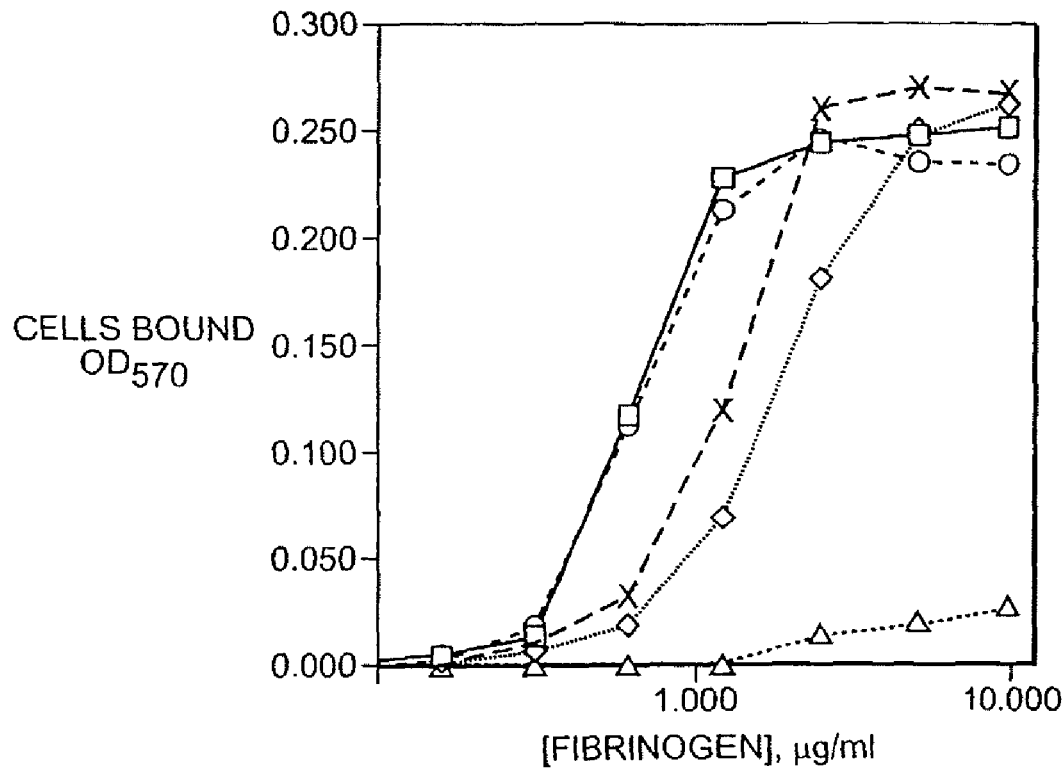
FIG. 15 is a graph of cells bound versus fibrinogen concentration showing adherence of *S. aureus* Newman and mutants to fibrinogen immobilized on ELISA plates. Increasing amounts of fibrinogen were used to coat the plates, and a fixed concentration of cells from exponential phase cultures were added. The square symbol represents wild-type; the diamond symbol represents clfA; the circle symbol represents clfB; the triangle symbol represents clfAclfB; the x symbol represents clfAclfB,clfB+.
Figure 16:
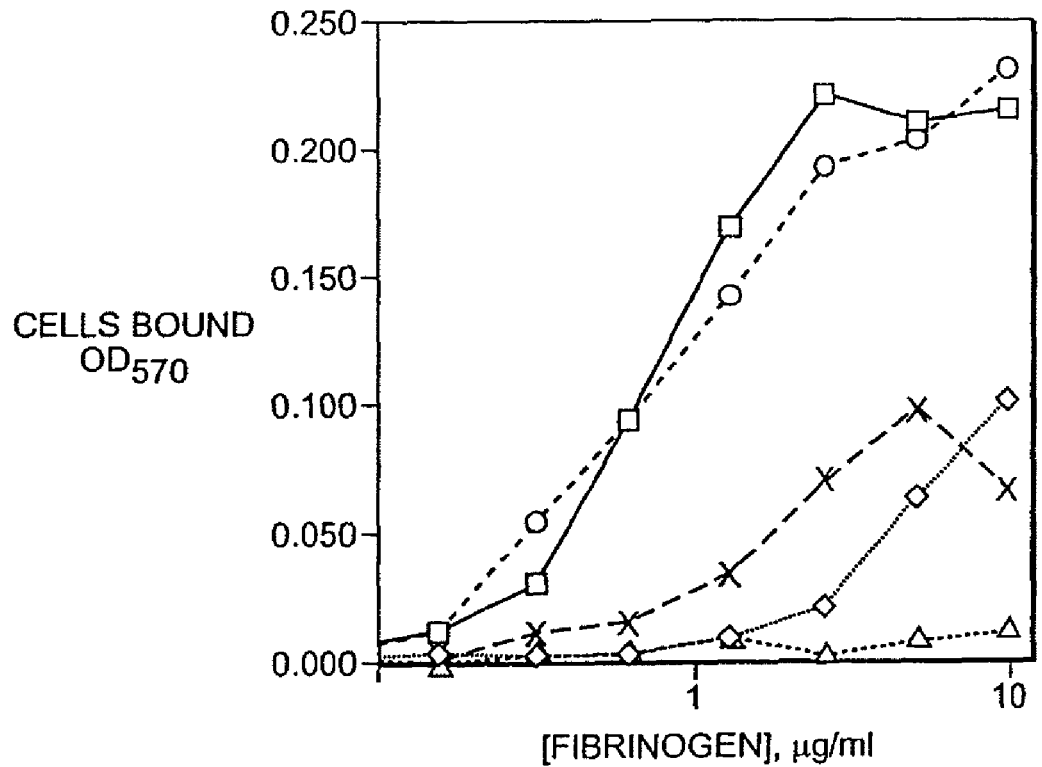
FIG. 16 is a graph of cells bound versus fibrinogen concentration showing adherence of *S. aureus* Newman and mutants to fibrinogen immobilized on ELISA plates. Increasing amounts of fibrinogen were used to coat the plates, and a fixed concentration of cells from stationary phase cultures added. The square symbol represents wild-type; the diamond symbol represents clfA; the circle symbol represents clfB; the triangle symbol represents clfAclfB; the x symbol represents clfAclfB,ClfB+.

The pattern of adherence strongly reflected that obtained in clumping assays (FIG. 15). Assays in which the concentration of cells was varied indicated that binding was approximately half the maximum value at a cell density of 0.4 OD (except for the double mutant), and this cell density was subsequently used routinely. Wild-type, clfA, clfB mutants and clfAclfB (pA1-1EA) showed a fibrinogen concentration-dependent increase in binding (FIG. 16). This increase was less marked for the clfB mutant (expressing ClfA) than for the clfA mutant (expressing ClfB), suggesting that ClfB may be a less avid and/or abundant receptor. With stationary phase cells, the clfB mutant continued to behave like the wild-type strain, whereas the clfA mutant bound much less avidly. As with clumping, adherence was slightly higher with the complemented double mutant, presumably due to a gene dosage effect.

The clumping and adherence assays show that ClfB mediates binding both to soluble and immobilized fibrinogen, closely resembling the activity of ClfA.

Figure 14:
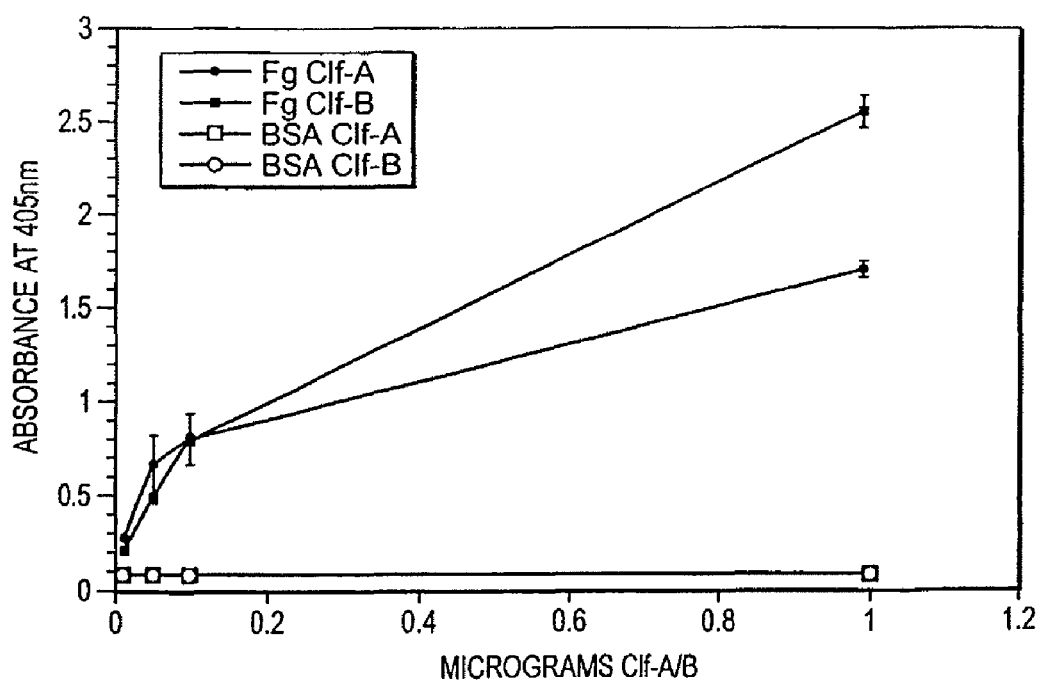
FIG. 14 is a graph of absorbance versus concentration of ClfA/ClfB comparing the binding of increasing concentrations of biotinylated recombinant region A from ClfA and ClfB to fibrinogen coated plates. Binding to BSA-coated plates is shown as a control. The closed square symbol represents fibrinogen-ClfA; the closed circle symbol represents fibrinogen-ClfB; the open square symbol represents BSA-ClfA; the open circle symbol represents BSA-ClfB.

The binding of increasing concentrations of biotinylated purified region A from ClfA and ClfB to solid phase fibrinogen was compared in a direct ELISA. The results are shown in FIG. 14. The adherence profiles of the two proteins were very similar, especially at the lower concentrations. At the highest concentration, binding of ClfA was approximately 50% greater than that of ClfB. Neither protein bound to BSA.

Effect of Anti-ClfB Antibody on Bacterial Adherence to Immobilized Fibrinogen

To study inhibition of fibrinogen binding by IgG, the cells used for the assay were preincubated with serial two-fold dilutions of purified IgG in PBS, starting with a concentration of 500 µg/ml. Preincubation was for two hours at 37° C. in Sarstedt™ multiwell test plates, and the cells were then transferred to ELISA plates coated with fibrinogen (2.5 µg/ml) and blocked as before. The rest of the assay was as before.

Figure 17:
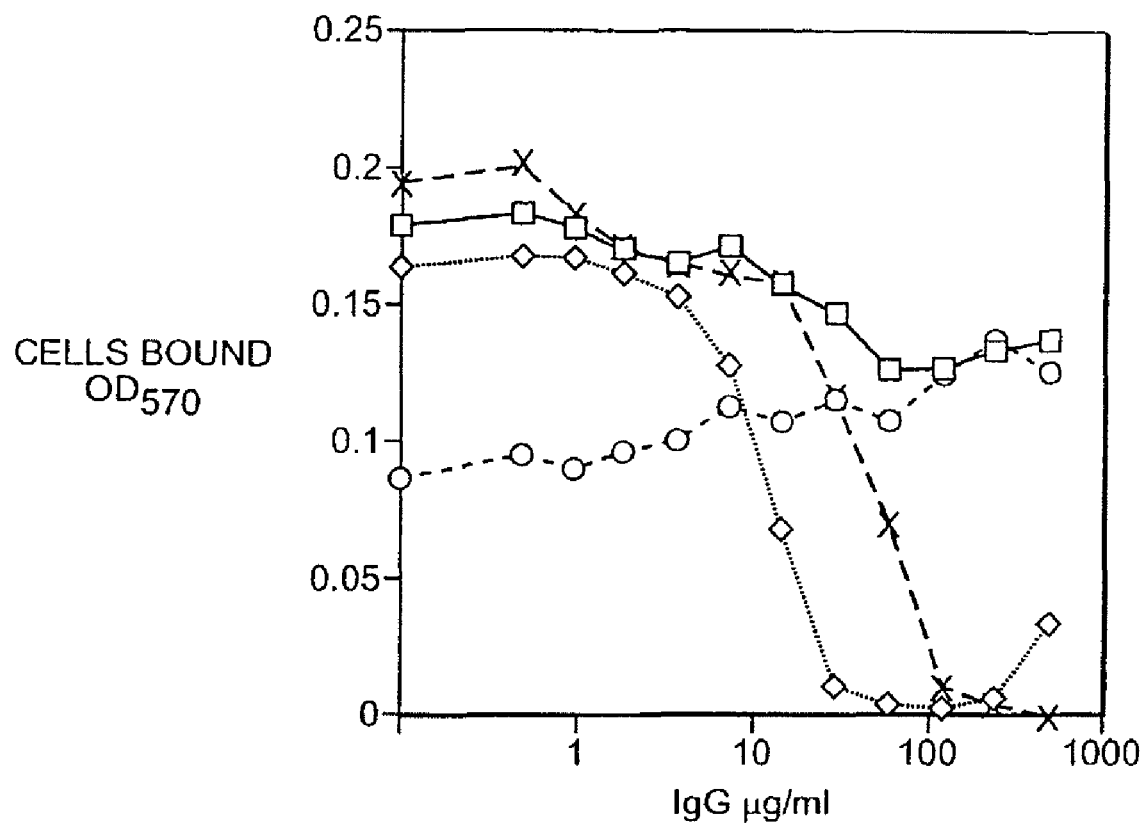
FIG. 17 is a graph of cells bound versus IgG concentration showing effects of preincubation with anti-ClfB IgG on adherence of *S. aureus* Newman and mutants to immobilized fibrinogen. The square symbol represents wild-type; the diamond symbol represents clfA; the circle symbol represents clfB; the x symbol represents clfAclfB,clfB+.

Cells from exponential phase cultures of wild-type and mutant Newman strains were preincubated with increasing concentrations of purified anti-ClfB IgG, and adherence to plastic surfaces coated with 2.5 µg/ml fibrinogen examined. The results are shown in FIG. 17. Binding of the clfB mutant was not inhibited, and binding of wild-type cells was almost unaffected, even at the highest antibody concentration. However, binding of the clfA mutant showed an IgG concentration-dependent decrease, with an IC$_{50}$ of 16 µg/ml. The double mutant carrying clfB on a complementing plasmid was also inhibited by the antibody, although the IC$_{50}$ was higher (50 µg/ml), presumably because more ClfB was being expressed on the cell surface.

Effect of Divalent Cations on Bacterial Adherence to Immobilized Fibrinogen

The effect of metal ions on fibrinogen binding was studied in a similar manner, preincubating the cells with serial two-fold dilutions of MgCl$_2$, MnCl$_2$ or MgCl$_2$ in TBS (50 mM Tris HCl, pH 7.5, 150 mM NaCl), starting with a concentration of 50 mM. TBS was used instead of PBS, which causes precipitation of both calcium and manganese. Since the cells bound less well under these conditions, the starting cell concentration was doubled.

It is known that the interaction of ClfA and fibrinogen is inhibited by Ca$^{2+}$ and Mn$^{2+}$, but not Mg$^{2+}$ ions. The effect of divalent cations on ClfB-promoted adherence to fibrinogen was thus tested. Preincubation of exponential phase cells of the wild-type strain and the clf mutants with CaCl$_2$ inhibited binding to fibrinogen. Those strains expressing ClfB alone showed greater sensitivity than the mutant expressing ClfA alone (clfB). The IC$_{50}$ for the wild-type strain and the clfB mutant were 17 and 14 mM, respectively, whereas for the clfA mutant and the clfB$^+$ complemented double mutant the IC$_{50}$ was 1.05 and 0.60 mM, respectively. MnCl$_2$ also inhibited attachment of the wild-type strain and mutants, with a stronger effect on strains expressing only clfB. The IC$_{50}$ for the wild-type and the clfB mutant was 3.3 and 6.4 mM, respectively, whereas for the clfA mutant and the double mutant carrying clfB+ on a complementing plasmid the IC$_{50}$ was 0.35 and 1.26 mM respectively. MgCl$_2$ had no effect on binding below 12.5 mM.

Thus, clfB promoted adherence of bacteria to immobilized fibrinogen is inhibited by Ca$^{2+}$ and Mn$^{2+}$ at similar concentrations to ClfA-promoted adherence. However, the mechanisms are likely to be different since ClfB does not contain a homologue of EF hand I implicated in Ca$^{2+}$ promoted modulation of ClfA-fibrinogen interactions.

Platelet-Fibrin Clot Adherence Assay

Adherence to platelet-fibrin clots was measured using a modification of an assay employed by Moreillon et al., *Infect. Immun.* 63: 4738-4743 (1995). Fresh canine blood was collected on 10% sodium citrate buffer (Sigma Chemical Co.), and centrifuged at 3000×g for 10 minutes at room temperature. The plasma fraction was removed and placed in a clean tube. Platelet-fibrin clots were made by mixing 0.5 ml volumes of plasma with 0.1 ml volumes of 0.2 mM CaCl$_2$ in 35 mm petri dishes. Thrombin (0.1 ml of 500 U/ml Sigma bovine thrombin) was then added, mixed in quickly, and the clots allowed to form. To measure bacterial adherence, 2 ml of PBS containing 5×10$^3$ cfu/ml of bacteria (from a BHI-grown exponential phase culture) was added to each dish, and the dishes shaken for three minutes on an orbital shaker. The inoculum was drained off and the clots washed twice for five minutes each with 2 ml of PBS. The clots were then overlaid with 3 ml of molten TSA, incubated for 15 hours at 37° C., and the colonies counted. The bacterial suspension used as an inoculum was spread on TSA plates to obtain a total viable count, and the percentage of bound inoculum calculated. Results represent means of 6-10 plates per strain, and were analyzed statistically using the student's T test.

The clfB mutation reduced adherence when compared to the wild-type strain Newman, as did the clfA mutation which was previously shown by Moreillon et al. to have significantly reduced adherence in this model.

Assay for Adherence to Haemodialysis Tubing

In order to demonstrate that ClfB could serve as an adhesin for *S. aureus* in biomaterial-related infections, explanted human haemodialysis tubing was tested for promotion of bacterial adherence in vitro. The tubing was coated with a complex mixture of host plasma proteins including fibrinogen and fibronectin.

Figure 19:
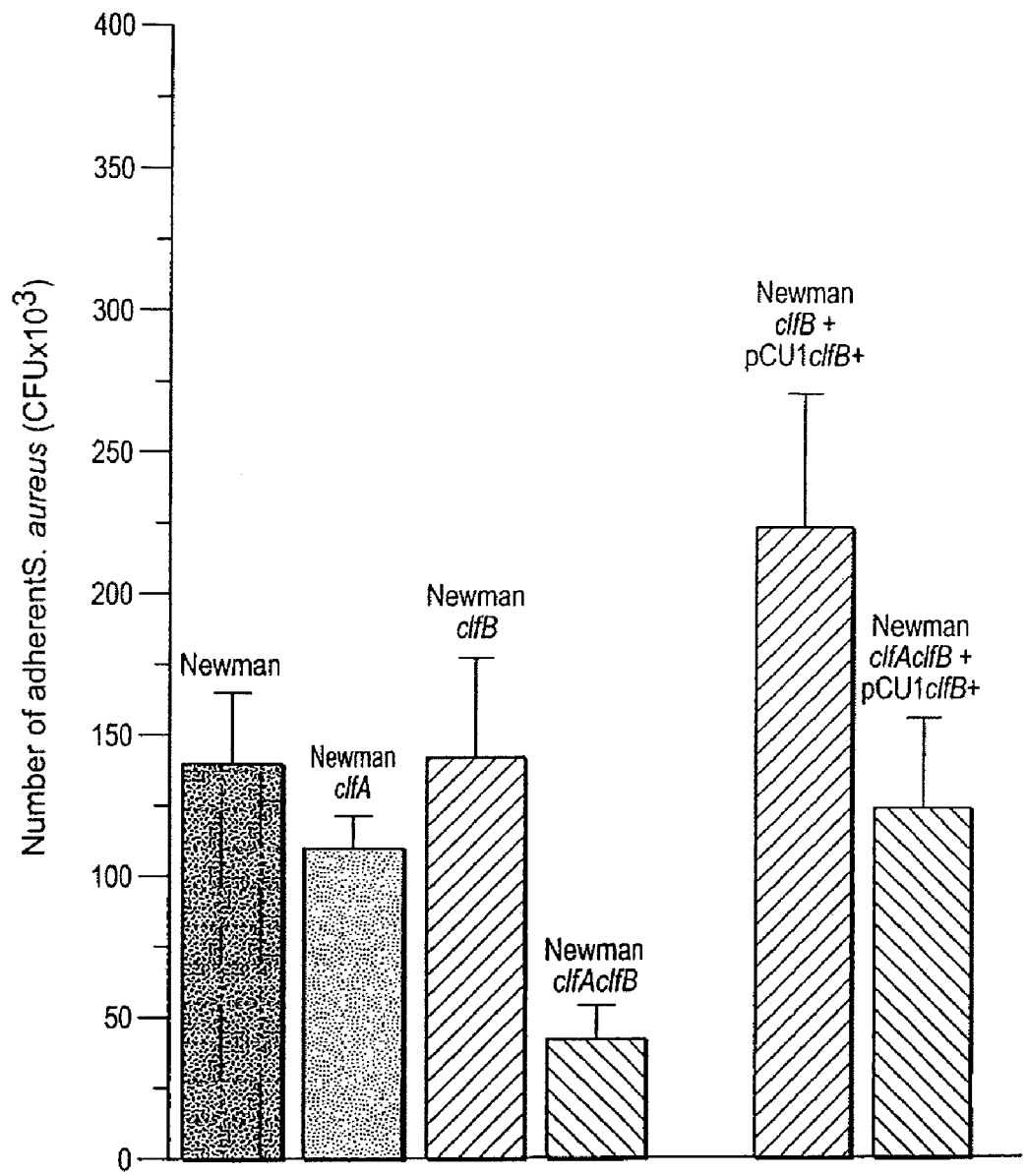
FIG. 19 is a bar graph showing adherence of *S. aureus* Newman and mutants to fibrinogen immobilized on PMMA (polymethylmethacrylate) coverslips. Cells from two hour shake-flask cultures were used. The graph provides the means and SEM of three experiments.

These experiments employed sections of haemodialysis tubing removed from patients 3 to 3.5 hours after implantation. Cultures were grown for two hours with shaking. Results, showing means with SEM of three experiments, are shown in FIG. 19.

Assay for Adherence to Fibrinogen-Coated PMMA Coverslips

Figure 18:
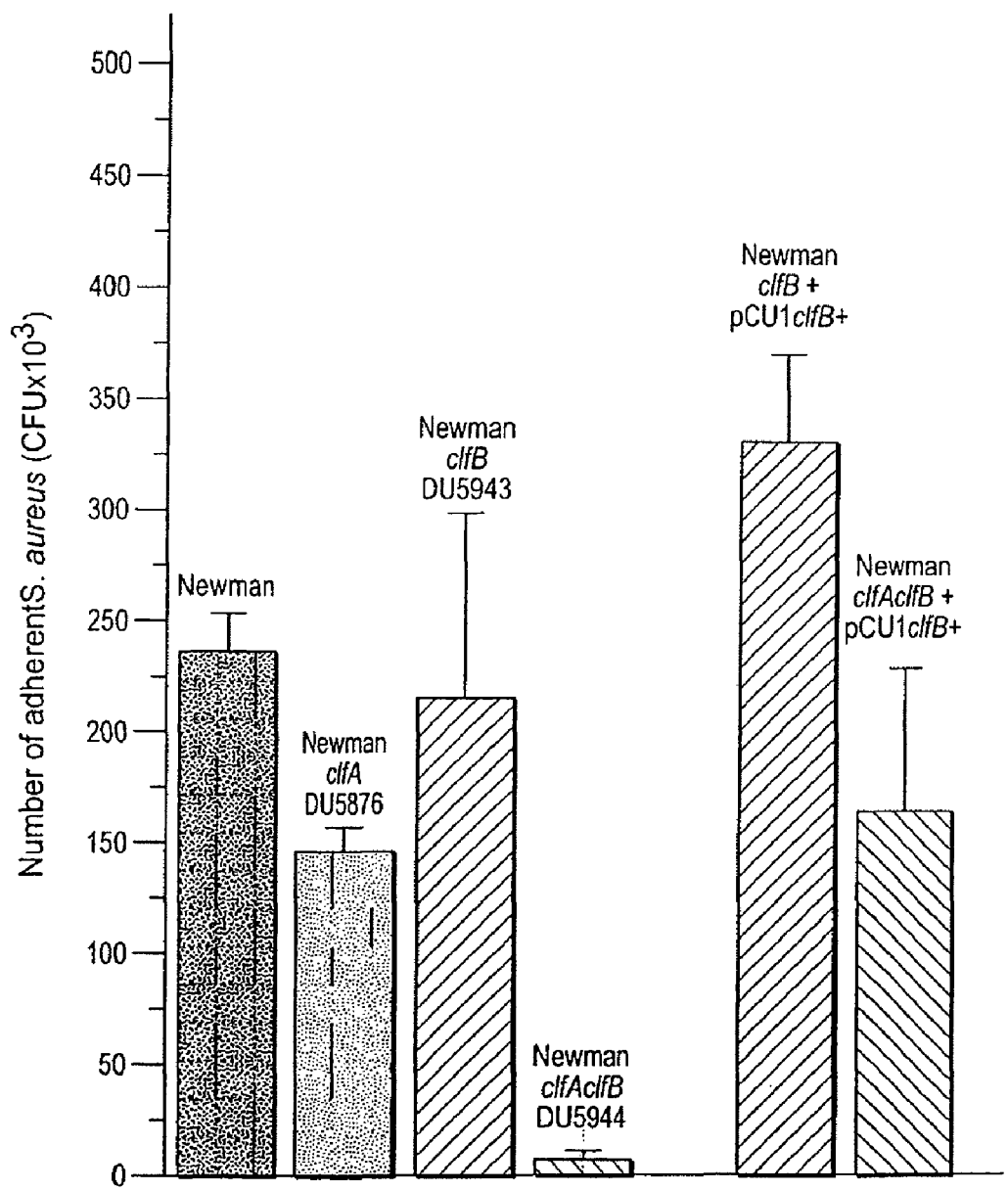
FIG. 18 is a bar graph showing adherence of *S. aureus* Newman and mutants to explanted hemodialysis tubing. Cells from two hour shake-flask cultures were used. The graph provides the means and SEM of three experiments.

Adherence of *S. aureus* Newman and mutants to fibrinogen-coated polymethylmethacrylate (PMMA) coverslips was measured as described by Greene et al., *Mol. Microbiol.* 17:1143-1152 (1995), except that the coverslips were coated with pure fibrinogen (1 µg/ml). Cultures for the assay were grown for two hours with shaking. Results, showing the means and SEM of triplicate experiments, are shown in FIG. 18.

The pattern of adherence to the tubing segments resembled the pattern of binding seen for immobilized fibrinogen in a parallel assay for adherence to fibrinogen immobilized on PMMA coverslips. The single clfA mutants had slightly lower levels of adherence compared to the wild-type whereas the double clfAclfB mutant was reduced to approximately 30% of wild-type level. Complementation of the single clfB mutant with the clfB gene on pA1-1EA restored binding to greater than wild-type levels, whereas complementation of the double mutant with the same plasmid restored binding only to the same level as the single clfA mutant.

Example 6

ClfB as a Virulence Factor in Experimental Endocarditis

Clumping factor A was shown to be a virulence factor promoting adherence to damaged heart valves in the rat model of experimental endocarditis of Moreillon et al., *Infect. Immun.* 63:4738-4743 (1995). Therefore, the role of ClfB in this infection was tested by comparing the infection rate of a clfB mutant and the mutant carrying the complementing clfB plasmid. Rats were infected intravenously at an ID$_{60}$ with 5×10$^3$ cfu. 61% of the wild-type control animals' valves were infected (n=13), whereas only 30% of the clfB mutant infected animals were colonized (n=20). In contrast 77% (n=9) of the complemented mutant became infected. This clearly shows that ClfB is an adhesin and potential virulence factor in the endocarditis model.

Example 7

Generation of TYTFTDYVD (SEQ ID NO:18) Peptide Antibodies

The nanopeptide, TYTFTDYVD (SEQ ID NO:18), was synthesized in multiple antigen peptide format (MAP; Research Genetics, Inc., Huntsville, Ala.). The peptide was conjugated to KLH according to manufacturers' directions (Pierce). Two female New Zealand White rabbits were immunized subcutaneously with the KLH-TYTFTDYVD (SEQ ID NO:18) conjugate emulsified with Freund's Complete Adjuvant. The rabbits were boosted 3 weeks later by subcutaneous injection of KLH-TYTFTDYVD (SEQ ID NO:18) adjuvanted with Freunds Incomplete. A third boost was administered subcutaneously with KLH-TYTFTDYVD (SEQ ID NO:18) in PBS. The animals were analyzed for TYTFTDYVD (SEQ ID NO:18) specific antibodies 21 days after the final boost. For purification of antibodies, antisera was diluted 1:1 with Tris-HCl pH 8.0 and passed over a Protein A-Sepharose® column After sequential washes with Tris-HCl pH 8.0, 0.5 M sodium chloride, the bound antibodies were eluted in 3.5 M MgCl$_2$, and dialyzed into PBS.

Immulon-2 microtiter plates (Dynex Technologies, Chantilly, Va.) were coated for 2 hr at room temperature with 1 µg ClfA, ClfB, or BSA. The protein coated plates were washed three times with PBS, 0.05% Tween 20 and then blocked with PBS, 1% BSA. The blocked plates were washed three times with PBS, 0.05% Tween 20. Fifty µl of the purified rabbit KLH-TYTFTDYVD (SEQ ID NO:18) antibodies were serially diluted in PBS and added to the microtiter plate and incubated at 25° C. on a rocker platform. The wells were washed three times with PBS, 0.05% Tween 20 and the secondary antibody was added to the wells and incubated for 1 hr at room temperature. The secondary antibody was alkaline phosphatase-conjugated goat anti-rabbit IgG (Bio-Rad), diluted 3000-fold in PBS. ELISA plates were developed for 1 hr at 37° C. with 1 mg/ml p-nitrophenyl phosphate (Sigma) in 1 M diethanolamine, 0.5 mM MgCl$_2$, pH 9.8, and quantified at 405 nm on a Perkin Elmer HTS 7000 Bio-Assay reader.

Figure 21:
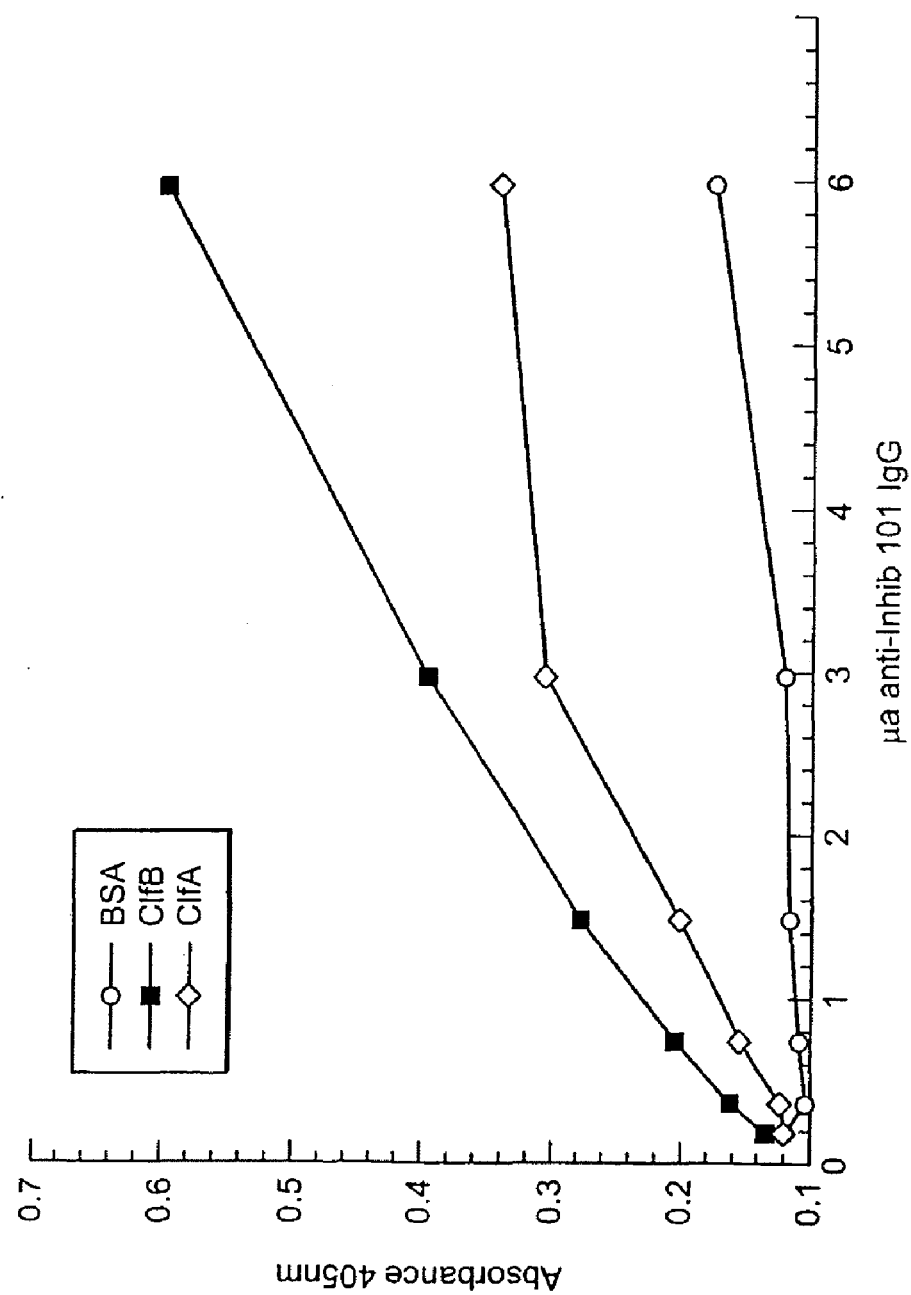
FIG. 21 is a graph of absorbance versus concentration of anti-TYTFTDYVD (SEQ ID NO: 18) antibodies, demonstrating the binding of increasing concentrations of the antibodies to ClfA, ClfB or BSA coated plates. BSA-coated plates are used as a control, and no significant binding is observed. The closed square symbol represents antibody bound to ClfB; the open diamond symbol represents antibody bound to ClfA; the open circle symbol represents BSA.

The data is shown in FIG. 21. These data indicate that the anti-consensus sequence TYTFTDYVD (SEQ ID NO:18) antibodies significantly bind to ClfA and ClfB proteins, but not to the control protein, BSA.

Example 8

Passive Immunization with Rabbit CUB IgG

The DNA encoding region A of clfB (encoding residues S45 to N542) was amplified from genomic DNA of *S. aureus* Newman using the following primers:

```
                                      (SEQ ID NO: 17)
Forward: 5' CGAAAGCTTGTCAGAACAATCGAACGATACAACG 3'

(SEQ ID NO: 16)
Reverse: 5' CGAGGATCCATTTACTGCTGAATCACC 3'
```

Cleavage sites for HindIII and BamHI (underlined) were appended to the 5' ends of the respective primers to facilitate cloning of the product into the His-tag expression vector pV4. Cloning employed *E. coli* JM101 as a host strain. The recombinant region A was purified by nickel affinity chromatography. Antibodies were raised in rabbits with the purified recombinant A region according to standard procedures. Anti-ClfB A region IgG was purified by affinity chromatography on a Protein A sepharose column.

Twenty Swiss Webster mice (23-28 g) were used to determine if passive immunization with purified rabbit anti-ClfB A region IgG could prevent infection mediated by a methicillin resistant *S. aureus*.

Methicillin resistant *S. aureus* strain 601 was cultured on blood agar plates. A single colony was then inoculated into 10 mls of BHI broth and incubated at 37° C. overnight. The culture was diluted to a 1:100 dilution, placed into 10 ml of fresh BHI and grown to an optical density (O.D.) of 1.5-2.0. The culture was then centrifuged and washed in 1.times.PBS. The culture was re-suspended in 1×PBS containing 5% BSA and 10% dimethyl sulfoxide (DMSO) and kept frozen at −20° C. The bacterial solution was thawed, washed, diluted in PBS, and adjusted to the appropriate concentrations before dosing the mice.

The mice were divided into four treatment groups (5 mice per treatment group). Mice were assigned to treatment groups as follows:

| Antibody/Bacteria | Dose CFU/mouse | No. of Mice |
|---|---|---|
| 1 Normal rabbit IgG/*S. aureus* | $3.81 \times 10^7$ | 5 |
| 2 Normal rabbit IgG/*S. aureus* | $7.62 \times 10^7$ | 5 |
| 3 Rabbit anti-ClfB IgG/*S. aureus* | $3.81 \times 10^7$ | 5 |
| 4 Rabbit anti-ClfB IgG/*S. aureus* | $7.62 \times 10^7$ | 5 |

On day −1, ten mice were administered 10 mg rabbit anti-ClfB region A IgG and 10 mice were given 10 mg normal rabbit IgG. Both antibodies were given via intraperitoneal (i.p.) injection. On day 0, all mice were infected intravenously (i.v.) with either $3.81 \times 10^7$ CFU *S. aureus* or $7.62 \times 10^7$ CFU *S. aureus*.

Systemic infection was measured by evaluation of body weight loss. Body weight loss is one of the primary parameters that is evaluated when cases of illness and injury are being assessed in mice. The body weight of each animal was recorded on Day −1 and every other day thereafter, including terminal sacrifice. The animals were weighed to the nearest 0.1 gram.

Mice injected with normal rabbit IgG displayed a significantly larger weight loss at the end of the experiment compared to mice passively immunized with rabbit anti-ClfB region A IgG (see table below). In addition, pathological evaluation of the mice at necropsy revealed a greater number of lesions and foci of infection in the kidneys from the mice receiving normal rabbit IgG compared to the kidneys from mice that were immunized with anti-ClfB region A IgG.

| | % Change in body weight (mean) | | | |
|---|---|---|---|---|
| Day of Study | Normal IgG/ *S. aureus* $3.81 \times 10^7$ | Anti-ClfB IgG/ *S. aureus* $3.81 \times 10^7$ | Normal IgG/ *S. aureus* $7.62 \times 10^7$ | Anti-ClfB IgG/ *S. aureus* $7.62 \times 10^7$ |
| −1 | 0 | 0 | 0 | 0 |
| 1 | 2.9 | 3.6 | 3.9 | 5.8 |
| 3 | 10 | 5.1 | 8.5 | 8.2 |
| 5 | 8.3 | 1.5 | 8.0 | 6.6 |

Example 9

ClfB Region A Binds .alpha. and .beta. Chains of Human Fibrinogen

Figure 22:
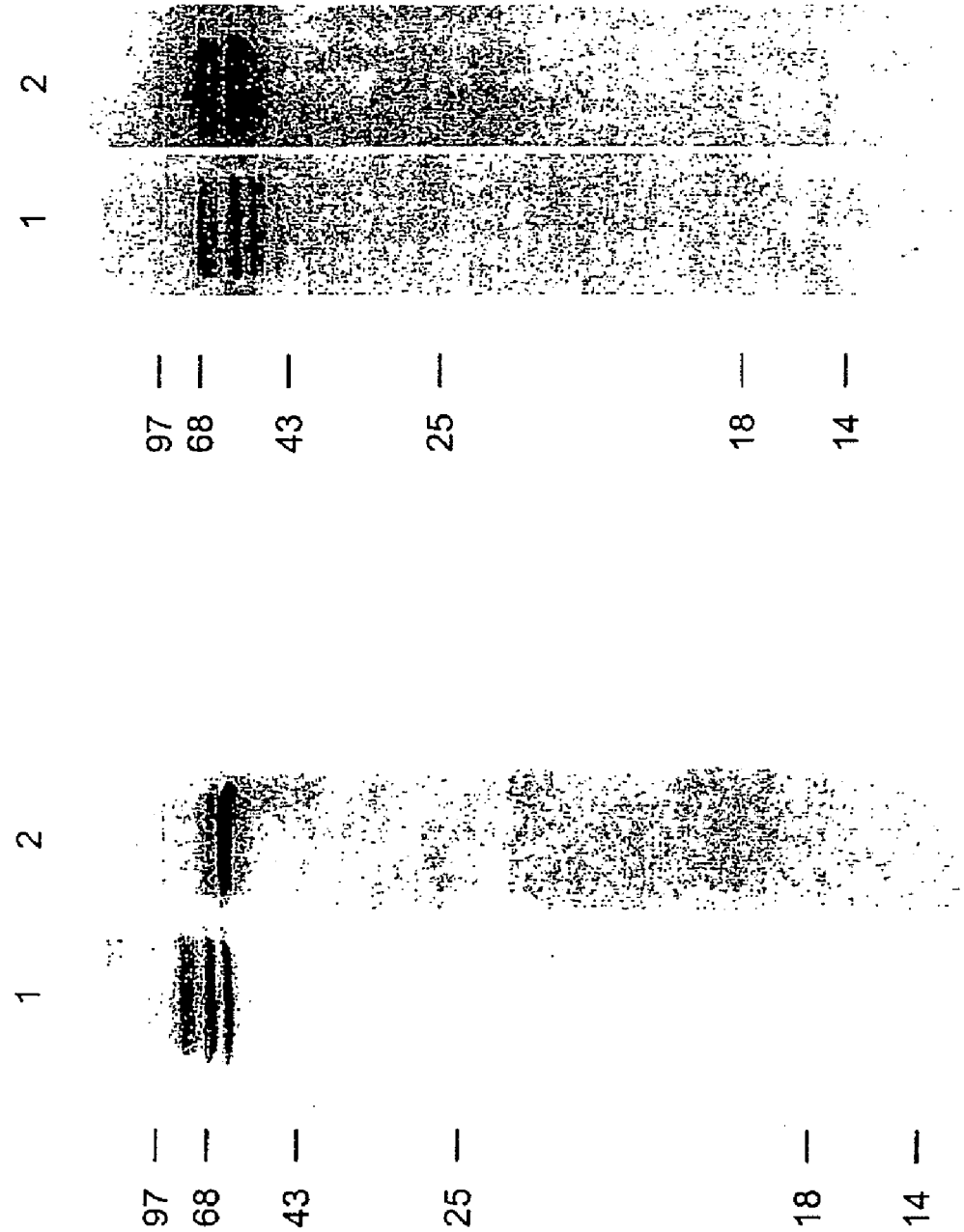
FIGS. 22A-22B show Western Blots which illustrate the differing specificities of ClfA and ClfB in the binding of human fibrinogen. The Western Blot was created by the separation of human fibrinogen, and later, the incubation of the nitrocellulose membrane with the A region of either biotinylated ClfA or ClfB. Biotinylated ClfA region A binds the γ chain of fibrinogen, as is seen in lane A2. Biotinylated ClfB region A binds to both the α and β chains of fibrinogen, as seen in lane B2.
Figure 23:
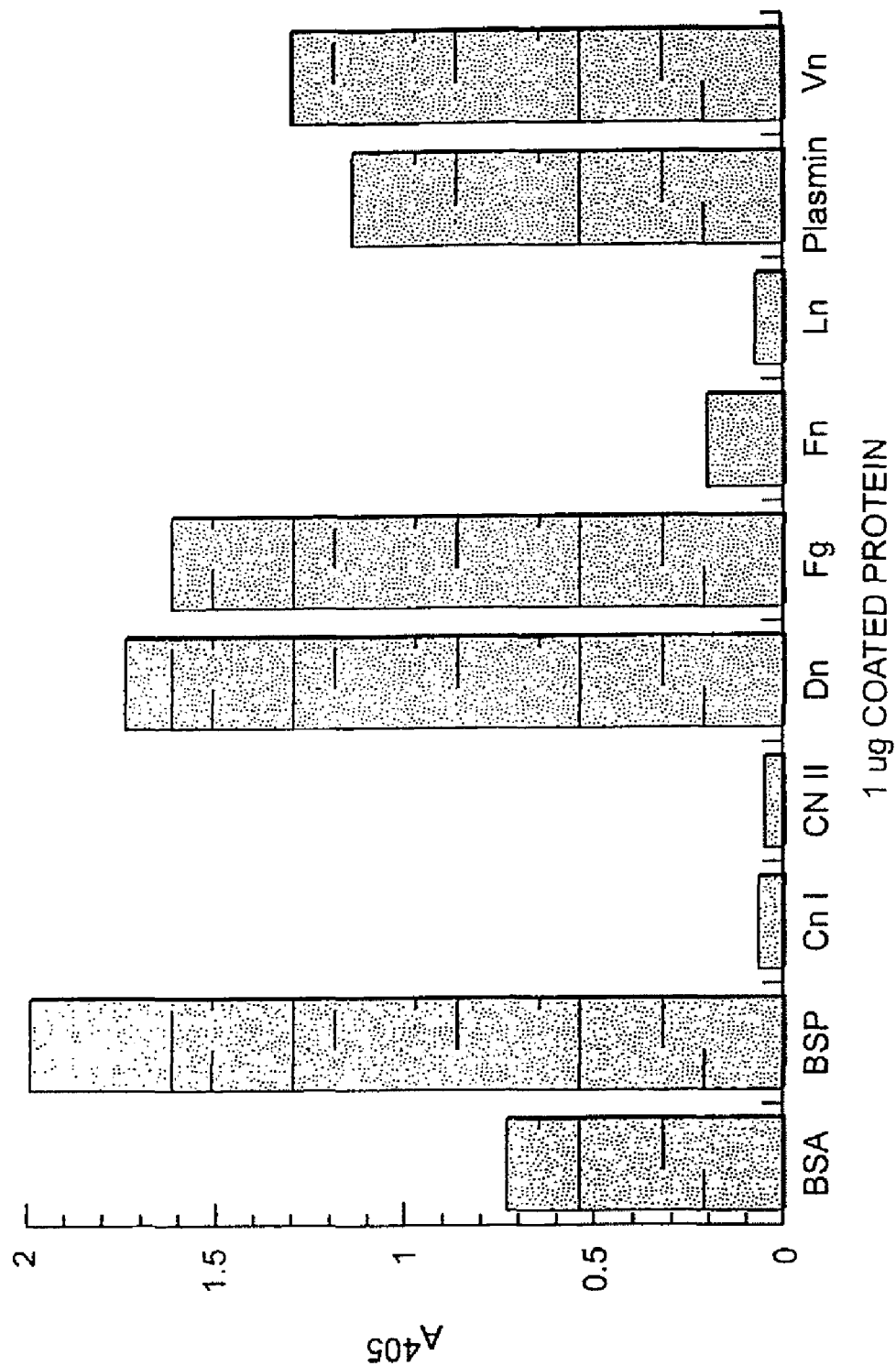
FIG. 23 is a bar graph showing adherence of recombinant SdrC region A (SdrCA) to ten different extracellular matrix proteins, BSA, BSP, two forms of collagen, decorin, fibrinogen, fibronectin, laminin, plasmin and vitronectin. The extracellular matrix proteins were immobilized on microtiter wells. Absorbance tests revealed reactivity of SdrCA with fibrinogen, BSP, decorin, plasmin and vitronectin.

Human fibrinogen (20 µg; Chromogenix) was separated by SDS-PAGE on a 15% acrylamide gel for 2 hours. Proteins were transferred to nitrocellulose at 100 V for 2 h. The membranes were blocked overnight in PBS containing 10% non-fat dry milk and then incubated with 2.5 µg/ml biotinylated ClfB or ClfA region A protein for 1 h with shaking. They were then given 3×5 mm washes with PBS containing 0.1% Tween 20 and incubated for 1 hr with avidin conjugated horseradish peroxidase (Boehringer Mannheim: 1:100,000 dilution). The filters were washed as before and developed using enhanced chemilluminescence (Amersham). The Western Blot (FIG. 22) illustrates the binding of biotinylated ClfA to the γ chain of fibrinogen and the binding of biotinylated ClfB to the α and β chains of fibrinogen.

Example 10

ClfB Region A Binds 75 kD and 50 kD Proteins from Human Rhabdomyosarcoma Cell Line Human Rhabdomyosarcoma Cells were lysed with the SDS-PAGE running buffer and varying amounts (2-10 µl) of the protein lysate were separated by SDS-PAGE on a 15% acrylamide gel for 2 h. Proteins were transferred to nitrocellulose at 100 V for 2 h. The membranes were blocked overnight in PBS containing 10% non-fat dry milk and then incubated with 2.5 µg/ml biotinylated ClfB or ClfA region A protein for 1 hr with constant shaking. They were then given 3.times.5 min washes with PBS containing 0.1% Tween 20 and incubated for 1 hr with avidin conjugated horseradish peroxidase (Boehringer Mannheim; 1:100,000 dilution). The filters were washed as before and developed using enhanced chemilluminescence (Amersham). Two major bands were seen at 50 kD and 75 kD that reacted with the biotinylated ClfB region A protein.

What is claimed is:

1. An isolated protein wherein the protein has an amino acid sequence comprising the sequence of SEQ ID NO: 7.

2. An isolated protein encoded by a nucleic acid sequence comprising the sequence of SEQ ID NO: 8.

3. The protein of claim 1 in a pharmaceutically acceptable carrier.

4. The protein of claim 2 in a pharmaceutically acceptable carrier.

5. The protein of claim 1 immobilized on a solid phase.

6. The protein of claim 2 immobilized on a solid phase.

7. A diagnostic kit comprising the protein according to claim 1 and antibodies binding to said protein.

8. A diagnostic kit comprising the protein according to claim 2 and antibodies binding to said protein.

* * * * *

SEQUENCE LISTING

<160> NUMBER OF SEQ ID NOS: 23

<210> SEQ ID NO 1
<211> LENGTH: 918
<212> TYPE: PRT
<213> ORGANISM: Staphylococcus aureus

<400> SEQUENCE: 1

```
Asn Gly Val Ile Phe Leu Lys Lys Arg Ile Asp Tyr Leu Ser Asn Lys
 1               5                  10                  15

Gln Asn Lys Tyr Ser Ile Arg Arg Phe Thr Val Gly Thr Thr Ser Val
             20                  25                  30

Ile Val Gly Ala Thr Ile Leu Phe Gly Ile Gly Asn His Gln Ala Gln
         35                  40                  45

Ala Ser Glu Gln Ser Asn Asp Thr Thr Gln Ser Ser Lys Asn Asn Ala
     50                  55                  60

Ser Ala Asp Ser Glu Lys Asn Asn Met Ile Glu Thr Pro Gln Leu Asn
 65                  70                  75                  80

Thr Thr Ala Asn Asp Thr Ser Asp Ile Ser Ala Asn Thr Asn Ser Ala
                 85                  90                  95

Asn Val Asp Ser Thr Thr Lys Pro Met Ser Thr Gln Thr Ser Asn Thr
            100                 105                 110

Thr Thr Thr Glu Pro Ala Ser Thr Asn Glu Thr Pro Gln Pro Thr Ala
        115                 120                 125

Ile Lys Asn Gln Ala Thr Ala Ala Lys Met Gln Asp Gln Thr Val Pro
    130                 135                 140

Gln Glu Gly Asn Ser Gln Val Asp Asn Lys Thr Thr Asn Asp Ala Asn
145                 150                 155                 160

Ser Ile Ala Thr Asn Ser Glu Leu Lys Asn Ser Gln Thr Leu Asp Leu
                165                 170                 175

Pro Gln Ser Ser Pro Gln Thr Ile Ser Asn Ala Gln Gly Thr Ser Lys
            180                 185                 190

Pro Ser Val Arg Thr Arg Ala Val Arg Ser Leu Ala Val Ala Glu Pro
        195                 200                 205

Val Val Asn Ala Ala Asp Ala Lys Gly Thr Asn Val Asn Asp Lys Val
    210                 215                 220

Thr Ala Ser Asn Phe Lys Leu Glu Lys Thr Thr Phe Asp Pro Asn Gln
225                 230                 235                 240

Ser Gly Asn Thr Phe Met Ala Ala Asn Phe Thr Val Thr Asp Lys Val
                245                 250                 255

Lys Ser Gly Asp Tyr Phe Thr Ala Lys Leu Pro Asp Ser Leu Thr Gly
            260                 265                 270

Asn Gly Asp Val Asp Tyr Ser Asn Ser Asn Thr Met Pro Ile Ala
        275                 280                 285

Asp Ile Lys Ser Thr Asn Gly Asp Val Val Ala Lys Ala Thr Tyr Asp
    290                 295                 300

Ile Leu Thr Lys Thr Tyr Thr Phe Val Phe Thr Asp Tyr Val Asn Asn
305                 310                 315                 320

Lys Glu Asn Ile Asn Gly Gln Phe Ser Leu Pro Leu Phe Thr Asp Arg
                325                 330                 335

Ala Lys Ala Pro Lys Ser Gly Thr Tyr Asp Ala Asn Ile Asn Ile Ala
            340                 345                 350

Asp Glu Met Phe Asn Asn Lys Ile Thr Tyr Asn Tyr Ser Ser Pro Ile
```

-continued

```
              355                 360                 365
Ala Gly Ile Asp Lys Pro Asn Gly Ala Asn Ile Ser Ser Gln Ile Ile
370                 375                 380

Gly Val Asp Thr Ala Ser Gly Gln Asn Thr Tyr Lys Gln Thr Val Phe
385                 390                 395                 400

Val Asn Pro Lys Gln Arg Val Leu Gly Asn Thr Trp Val Tyr Ile Lys
                    405                 410                 415

Gly Tyr Gln Asp Lys Ile Glu Glu Ser Ser Gly Lys Val Ser Ala Thr
                    420                 425                 430

Asp Thr Lys Leu Arg Ile Phe Glu Val Asn Asp Thr Ser Lys Leu Ser
                435                 440                 445

Asp Ser Tyr Tyr Ala Asp Pro Asn Asp Ser Asn Leu Lys Glu Val Thr
        450                 455                 460

Asp Gln Phe Lys Asn Arg Ile Tyr Tyr Glu His Pro Asn Val Ala Ser
465                 470                 475                 480

Ile Lys Phe Gly Asp Ile Thr Lys Thr Tyr Val Val Leu Val Glu Gly
                    485                 490                 495

His Tyr Asp Asn Thr Gly Lys Asn Leu Lys Thr Gln Val Ile Gln Glu
                500                 505                 510

Asn Val Asp Pro Val Thr Asn Arg Asp Tyr Ser Ile Phe Gly Trp Asn
            515                 520                 525

Asn Glu Asn Val Val Arg Tyr Gly Gly Ser Ala Asp Gly Asp Ser
        530                 535                 540

Ala Val Asn Pro Lys Asp Pro Thr Pro Gly Pro Val Asp Pro Glu
545                 550                 555                 560

Pro Ser Pro Asp Pro Glu Pro Glu Pro Thr Pro Asp Pro Glu Pro Ser
                    565                 570                 575

Pro Asp Pro Glu Pro Glu Pro Ser Pro Asp Pro Asp Pro Asp Ser Asp
                580                 585                 590

Ser Asp Ser Asp Ser Gly Ser Asp Ser Asp Ser Gly Ser Asp Ser Asp
            595                 600                 605

Ser Glu Ser Asp Ser Asp Ser Asp Ser Asp Ser Asp Ser Asp Ser Asp
        610                 615                 620

Ser Asp Ser Glu Ser Asp Ser Asp Ser Glu Ser Asp Ser Asp Ser Asp
625                 630                 635                 640

Ser Asp Ser Asp Ser Asp Ser Asp Ser Asp Ser Asp Ser Asp Ser Asp
                    645                 650                 655

Ser Asp Ser Asp Ser Asp Ser Asp Ser Asp Ser Asp Ser Glu Ser Asp
                660                 665                 670

Ser Asp Ser Glu Ser Asp Ser Glu Ser Asp Ser Asp Ser Asp Ser Asp
            675                 680                 685

Ser Asp Ser Asp Ser Asp Ser Asp Ser Asp Ser Asp Ser Asp Ser Asp
        690                 695                 700

Ser Asp Ser Asp Ser Asp Ser Asp Ser Asp Ser Asp Ser Asp Ser Asp
705                 710                 715                 720

Ser Asp Ser Asp Ser Asp Ser Asp Ser Asp Ser Asp Ser Asp Ser Asp
                    725                 730                 735

Ser Asp Ser Asp Ser Asp Ser Asp Ser Asp Ser Asp Ser Asp Ser Asp
                740                 745                 750

Ser Asp Ser Asp Ser Asp Ser Asp Ser Asp Ser Asp Ser Asp Ser Asp
            755                 760                 765

Ser Asp Ser Asp Ser Asp Ser Asp Ser Asp Ser Asp Ser Asp Ser Asp
        770                 775                 780
```

```
Ser Asp Ser Asp Ser Asp Ser Asp Ser Asp Ser Asp Ser Asp Ser Asp
785                 790                 795                 800

Ser Asp Ser Asp Ser Asp Ser Asp Ser Asp Ser Asp Ser Asp Ser Asp
            805                 810                 815

Ser Asp Ser Asp Ser Asp Ser Asp Ser Asp Ser Asp Ser Asp Ser Asp
        820                 825                 830

Ser Asp Ser Asp Ser Asp Ser Asp Ser Asp Ser Asp Ser Arg Val Thr
    835                 840                 845

Pro Pro Asn Asn Glu Gln Lys Ala Pro Ser Asn Pro Lys Gly Glu Val
        850                 855                 860

Asn His Ser Asn Lys Val Ser Lys Gln His Lys Thr Asp Ala Leu Pro
865                 870                 875                 880

Glu Thr Gly Asp Lys Ser Glu Asn Thr Asn Ala Thr Leu Phe Gly Ala
                885                 890                 895

Met Met Ala Leu Leu Gly Ser Leu Leu Leu Phe Arg Lys Arg Lys Gln
            900                 905                 910

Asp His Lys Glu Lys Ala
        915

<210> SEQ ID NO 2
<211> LENGTH: 2969
<212> TYPE: DNA
<213> ORGANISM: Staphylococcus aureus

<400> SEQUENCE: 2
```

| | | | | |
|---|---|---|---|---|
| tagaaattga aatggagtaa tattttttgaa aaaaagaatt gattatttgt cgaataagca | | | | 60 |
| gaataagtat tcgattagac gttttacagt aggtaccaca tcagtaatag tagggggcaac | | | | 120 |
| tatactattt gggataggca atcatcaagc acaagcttca gaacaatcga acgatacaac | | | | 180 |
| gcaatcttcg aaaaataatg caagtgcaga ttccgaaaaa aacaatatga tagaaacacc | | | | 240 |
| tcaattaaat acaacggcta atgatacatc tgatattagt gcaaacacaa acagtgcgaa | | | | 300 |
| tgtagatagc acaacaaaac caatgtctac acaaacgagc aataccacta acagagcc | | | | 360 |
| agcttcaaca atgaaacac ctcaaccgac ggcaattaaa aatcaagcaa ctgctgcaaa | | | | 420 |
| aatgcaagat caaactgttc ctcaagaagg aaattctcaa gtagataata aaacaacgaa | | | | 480 |
| tgatgctaat agcatagcaa caaacagtga gcttaaaaat tctcaaacat tagatttacc | | | | 540 |
| acaatcatca ccacaaacga tttccaatgc gcaaggaact agtaaaccaa gtgttagaac | | | | 600 |
| gagagctgta cgtagtttag ctgttgctga accggtagta aatgctgctg atgctaaagg | | | | 660 |
| tacaaatgta aatgataaag ttacggcaag taatttcaag ttagaaaaga ctacatttga | | | | 720 |
| ccctaatcaa agtggtaaca catttatggc ggcaaatttt acagtgacag ataaagtgaa | | | | 780 |
| atcagggat tattttacag cgaagttacc agatagttta actggtaatg agacgtgga | | | | 840 |
| ttattctaat tcaataata cgatgccaat tgcagacatt aaaagtacga atggcgatgt | | | | 900 |
| tgtagctaaa gcaacatatg atatcttgac taagacgtat acatttgtct ttacagatta | | | | 960 |
| tgtaaataat aaagaaaata ttaacggaca atttcatta cctttattta cagaccgagc | | | | 1020 |
| aaaggcacct aaatcaggaa catatgatgc gaatattaat attgcggatg aaatgtttaa | | | | 1080 |
| taataaaatt acttataact atagttcgcc aattgcagga attgataaac caatggcgc | | | | 1140 |
| gaacatttct tctcaaatta ttggtgtaga tacagcttca ggtcaaaaca catacaagca | | | | 1200 |
| aacagtattt gttaaccta agcaacgagt tttaggtaat acgtgggtgt atattaaagg | | | | 1260 |
| ctaccaagat aaaatcgaag aaagtagcgg taaagtaagt gctacagata caaaactgag | | | | 1320 |

```
aatttttgaa gtgaatgata catctaaatt atcagatagc tactatgcag atccaaatga    1380
ctctaacctt aaagaagtaa cagaccaatt taaaaataga atctattatg agcatccaaa    1440
tgtagctagt attaaatttg gtgatattac taaaacatat gtagtattag tagaagggca    1500
ttacgacaat acaggtaaga acttaaaaac tcaggttatt caagaaaatg ttgatcctgt    1560
aacaaatcga gactacagta ttttcggttg gaataatgag aatgttgtac gttatggtgg    1620
tggaagtgct gatggtgatt cagcagtaaa tccgaaagac ccaactccag ggccgccggt    1680
tgacccagaa ccaagtccag acccagaacc agaaccaacg ccagatccag aaccaagtcc    1740
agacccagaa ccggaaccaa gcccagaccc ggatccggat tcggattcag acagtgactc    1800
aggctcagac agcgactcag gttcagatag cgactcagaa tcagatagcg attcggattc    1860
agacagtgat tcagattcag acagcgactc agaatcagat agcgattcag aatcagatag    1920
cgactcagat tcagatagcg attcagattc agatagcgat tcagattcag atagcgattc    1980
ggattcagac agtgattcag attcagacag cgactcagaa tcagatagcg actcagaatc    2040
agatagtgag tcagattcag acagtgactc ggactcagac agtgattcag actcagatag    2100
cgattcagac tcagatagcg attcagattc agacagcgac tcagattcag acagcgactc    2160
agactcagat agcgactcag actcagacag cgactcagat tcagatagcg attcagactc    2220
agacagcgac tcagactcag acagcgactc agactcagat agcgactcag attcagatag    2280
cgattcagac tcagacagcg actcagattc agatagcgat tcggactcag acagcgattc    2340
agattcagac agcgactcag actcggatag cgattcagat tcagatagcg attcggattc    2400
agacagtgat tcagattcag acagcgactc agactcggat agcgactcag actcagacag    2460
cgattcagac tcagatagcg actcagactc ggatagcgac tcggattcag atagcgactc    2520
agactcagat agtgactccg attcaagagt tacaccacca aataatgaac agaaagcacc    2580
atcaaatcct aaaggtgaag taaccattcc taataaggta tcaaaacaac acaaaactga    2640
tgctttacca gaaacaggag ataagagcga aaacacaaat gcaactttat ttggtgcaat    2700
gatggcatta ttaggatcat tactattgtt tagaaaacgc aagcaagatc ataaagaaaa    2760
agcgtaaata ctttttttagg ccgaatacat ttgtattcgg ttttttttgtt gaaaatgatt    2820 ttaaagtgaa ttgattaagc gtaaaatgtt gataaagtag aattagaaag gggtcatgac    2880
gtatggctta tatttcatta aactatcatt caccaacaat tggtatgcat caaaatttga    2940
cagtcatttt accggaagaa cgagaattc                                     2969
```

<210> SEQ ID NO 3  
<211> LENGTH: 930  
<212> TYPE: PRT  
<213> ORGANISM: Staphylococcus aureus

<400> SEQUENCE: 3

```
Met Asn Asn Lys Lys Thr Ala Thr Asn Arg Lys Gly Met Ile Pro Asn
 1               5                  10                  15

Arg Leu Asn Lys Phe Ser Ile Arg Lys Tyr Ser Val Gly Thr Ala Ser
            20                  25                  30

Ile Leu Val Gly Thr Thr Leu Ile Phe Gly Leu Ser Gly His Glu Ala
        35                  40                  45

Lys Ala Ala Glu His Thr Asn Gly Glu Leu Asn Gln Ser Lys Asn Glu
    50                  55                  60

Thr Thr Ala Pro Ser Glu Asn Lys Thr Thr Lys Lys Val Asp Ser Arg
65                  70                  75                  80
```

-continued

Gln Leu Lys Asp Asn Thr Gln Thr Ala Thr Ala Asp Gln Pro Lys Val
                85                  90                  95

Thr Met Ser Asp Ser Ala Thr Val Lys Glu Thr Ser Ser Asn Met Gln
            100                 105                 110

Ser Pro Gln Asn Ala Thr Ala Asn Gln Ser Thr Thr Lys Thr Ser Asn
        115                 120                 125

Val Thr Thr Asn Asp Lys Ser Ser Thr Tyr Ser Asn Glu Thr Asp
    130                 135                 140

Lys Ser Asn Leu Thr Gln Ala Lys Asp Val Ser Thr Thr Pro Lys Thr
145                 150                 155                 160

Thr Thr Ile Lys Pro Arg Thr Leu Asn Arg Met Ala Val Asn Thr Val
                165                 170                 175

Ala Ala Pro Gln Gln Gly Thr Asn Val Asn Asp Lys Val His Phe Ser
            180                 185                 190

Asn Ile Asp Ile Ala Ile Asp Lys Gly His Val Asn Gln Thr Thr Gly
        195                 200                 205

Lys Thr Glu Phe Trp Ala Thr Ser Ser Asp Val Leu Lys Leu Lys Ala
    210                 215                 220

Asn Tyr Thr Ile Asp Asp Ser Val Lys Glu Gly Asp Thr Phe Thr Phe
225                 230                 235                 240

Lys Tyr Gly Gln Tyr Phe Arg Pro Gly Ser Val Arg Leu Pro Ser Gln
                245                 250                 255

Thr Gln Asn Leu Tyr Asn Ala Gln Gly Asn Ile Ile Ala Lys Gly Ile
            260                 265                 270

Tyr Asp Ser Thr Thr Asn Thr Thr Thr Tyr Thr Phe Thr Asn Tyr Val
        275                 280                 285

Asp Gln Tyr Thr Asn Val Arg Gly Ser Phe Glu Gln Val Ala Phe Ala
    290                 295                 300

Lys Arg Lys Asn Ala Thr Thr Asp Lys Thr Ala Tyr Lys Met Glu Val
305                 310                 315                 320

Thr Leu Gly Asn Asp Thr Tyr Ser Glu Glu Ile Ile Val Asp Tyr Gly
                325                 330                 335

Asn Lys Lys Ala Gln Pro Leu Ile Ser Ser Thr Asn Tyr Ile Asn Asn
            340                 345                 350

Glu Asp Leu Ser Arg Asn Met Thr Ala Tyr Val Asn Gln Pro Lys Asn
        355                 360                 365

Thr Tyr Thr Lys Gln Thr Phe Val Thr Asn Leu Thr Gly Tyr Lys Phe
    370                 375                 380

Asn Pro Asn Ala Lys Asn Phe Lys Ile Tyr Glu Val Thr Asp Gln Asn
385                 390                 395                 400

Gln Phe Val Asp Ser Phe Thr Pro Asp Thr Ser Lys Leu Lys Asp Val
                405                 410                 415

Thr Asp Gln Phe Asp Val Ile Tyr Ser Asn Asp Asn Lys Thr Ala Thr
            420                 425                 430

Val Asp Leu Met Lys Gly Gln Thr Ser Ser Asn Lys Gln Tyr Ile Ile
        435                 440                 445

Gln Gln Val Ala Tyr Pro Asp Asn Ser Ser Thr Asp Asn Gly Lys Ile
    450                 455                 460

Asp Tyr Thr Leu Asp Thr Asp Lys Thr Lys Tyr Ser Trp Ser Asn Ser
465                 470                 475                 480

Tyr Ser Asn Val Asn Gly Ser Ser Thr Ala Asn Gly Asp Gln Lys Lys
                485                 490                 495

-continued

```
Tyr Asn Leu Gly Asp Tyr Val Trp Glu Asp Thr Asn Lys Asp Gly Lys
            500                 505                 510

Gln Asp Ala Asn Glu Lys Gly Ile Lys Gly Val Tyr Val Ile Leu Lys
            515                 520                 525

Asp Ser Asn Gly Lys Glu Leu Asp Arg Thr Thr Thr Asp Glu Asn Gly
            530                 535                 540

Lys Tyr Gln Phe Thr Gly Leu Ser Asn Gly Thr Tyr Ser Val Glu Phe
545                 550                 555                 560

Ser Thr Pro Ala Gly Tyr Thr Pro Thr Thr Ala Asn Val Gly Thr Asp
            565                 570                 575

Asp Ala Val Asp Ser Asp Gly Leu Thr Thr Gly Val Ile Lys Asp
            580                 585                 590

Ala Asp Asn Met Thr Leu Asp Ser Gly Phe Tyr Lys Thr Pro Lys Tyr
            595                 600                 605

Ser Leu Gly Asp Tyr Val Trp Tyr Asp Ser Asn Lys Asp Gly Lys Arg
            610                 615                 620

Asp Ser Thr Glu Lys Gly Ile Lys Gly Val Lys Val Thr Leu Gln Asn
625                 630                 635                 640

Glu Lys Gly Glu Val Ile Gly Thr Thr Glu Thr Asp Glu Asn Gly Lys
            645                 650                 655

Tyr Arg Phe Asp Asn Leu Asp Ser Gly Lys Tyr Lys Val Ile Phe Glu
            660                 665                 670

Lys Pro Ala Gly Leu Thr Gln Thr Gly Thr Asn Thr Thr Glu Asp Asp
            675                 680                 685

Lys Asp Ala Asp Gly Gly Glu Val Asp Val Thr Ile Thr Asp His Asp
            690                 695                 700

Asp Phe Thr Leu Asp Asn Gly Tyr Tyr Glu Glu Glu Thr Ser Asp Ser
705                 710                 715                 720

Asp Ser Asp Ser Asp Ser Asp Ser Asp Ser Asp Ser Asp Ser Asp Ser
            725                 730                 735

Asp Ser Asp Ser Asp Ser Asp Ser Asp Ser Asp Ser Asp Ser Asp Ser
            740                 745                 750

Asp Ser Asp Ser Asp Ser Asp Ser Asp Ser Asp Ser Asp Ser Asn Ser
            755                 760                 765

Asp Ser Asp Ser Asp Ser Asp Ser Asp Ser Asp Ser Asp Ser Asp Ser
            770                 775                 780

Asp Ser Asp Ser Asp Ser Asp Ser Asp Ser Asp Ser Asp Ser Asp Ser
785                 790                 795                 800

Asp Ser Asp Ser Asp Ser Asp Ser Asp Ser Asp Ser Asp Ser Asp Ser
            805                 810                 815

Asp Ser Asp Ser Asp Ser Asp Ser Asp Ser Asp Ser Asp Ser Asp Ser
            820                 825                 830

Asp Ser Asp Ser Asp Ser Asp Ser Asp Ser Asp Ser Asp Ser Asp Ser
            835                 840                 845

Asp Ser Asp Ser Asp Ser Asp Ser Asp Ser Asp Ser Asp Ser Asp Ser
            850                 855                 860

Asp Ser Asp Ser Asp Ser Asp Ser Asp Ser Asn Asp Ser Asp Ser
865                 870                 875                 880

Asp Ser Asp Ser Asp Ser Asp Ala Gly Lys His Thr Pro Ala Lys Pro
            885                 890                 895

Met Ser Thr Val Lys Asp Gln His Lys Thr Ala Lys Ala Leu Pro Glu
            900                 905                 910

Thr Gly Ser Glu Asn Asn Asn Ser Asn Asn Gly Thr Leu Phe Gly Gly
```

Leu Phe
  930

<210> SEQ ID NO 4
<211> LENGTH: 2841
<212> TYPE: DNA
<213> ORGANISM: Staphylococcus aureus

<400> SEQUENCE: 4

| | | | | | |
|---|---|---|---|---|---|
| atgaataata | aaaagacagc | aacaaataga | aaaggcatga | taccaaatcg | attaaacaaa | 60 |
| ttttcgataa | gaaagtattc | tgtaggtact | gcttcaattt | tagtagggac | aacattgatt | 120 |
| tttgggttaa | gtggtcatga | agctaaagcg | gcagaacata | cgaatggaga | attaaatcaa | 180 |
| tcaaaaaatg | aaacgacagc | cccaagtgag | aataaaacaa | ctaaaaaagt | tgatagtcgt | 240 |
| caactaaaag | acaatacgca | aactgcaact | gcagatcagc | taaagtgac | aatgagtgat | 300 |
| agtgcaacag | ttaagaaac | tagtagtaac | atgcaatcac | cacaaaacgc | tacagctaat | 360 |
| caatctacta | caaaaactag | caatgtaaca | acaaatgata | aatcatcaac | tacatatagt | 420 |
| aatgaaactg | ataaagtaa | tttaacacaa | gcaaaagatg | tttcaactac | acctaaaaca | 480 |
| acgactatta | aaccaagaac | tttaaatcgc | atggcagtga | atactgttgc | agctccacaa | 540 |
| caaggaacaa | atgttaatga | taaagtacat | ttttcaaata | ttgacattgc | gattgataaa | 600 |
| ggacatgtta | tcagactac | tggtaaaact | gaattttggg | caacttcaag | tgatgtttta | 660 |
| aaattaaaag | caaattacac | aatcgatgat | tctgttaaag | agggcgatac | atttactttt | 720 |
| aaatatggtc | aatatttccg | tccaggatca | gtaagattac | cttcacaaac | tcaaaattta | 780 |
| tataatgccc | aaggtaatat | tattgcaaaa | ggtatttatg | atagtacaac | aaacacaaca | 840 |
| acatatactt | ttacgaacta | tgtagatcaa | tatacaaatg | ttagaggtag | ctttgaacaa | 900 |
| gttgcatttg | cgaaacgtaa | aaatgcaaca | actgataaaa | cagcttataa | aatggaagta | 960 |
| actttaggta | atgatacata | tagcgaagaa | atcattgtcg | attatggtaa | taaaaaagca | 1020 |
| caaccgctta | tttcaagtac | aaactatatt | aacaatgaag | atttatcgcg | taatatgact | 1080 |
| gcatatgtaa | atcaacctaa | aaatacatat | actaaacaaa | cgtttgttac | taatttaact | 1140 |
| ggatataaat | ttaatccaaa | tgcaaaaaac | ttcaaaattt | acgaagtgac | agatcaaaat | 1200 |
| caatttgtgg | atagtttcac | ccctgatact | tcaaaactta | agatgttac | tgatcaattc | 1260 |
| gatgttattt | atagtaatga | taataaaaca | gctacagtcg | atttaatgaa | aggccaaaca | 1320 |
| agcagcaata | acaatacat | cattcaacaa | gttgcttatc | cagataatag | ttcaacagat | 1380 |
| aatggaaaaa | ttgattatac | tttagacact | gacaaaacta | aatatagttg | gtcaaatagt | 1440 |
| tattcaaatg | tgaatggctc | atcaactgct | aatggcgacc | aaaagaaata | taatctaggt | 1500 |
| gactatgtat | gggaagatac | aaataaagat | ggtaaacaag | atgccaatga | aaagggatt | 1560 |
| aaaggtgttt | atgtcattct | taagatagt | aacggtaaag | aattagatcg | tacgacaaca | 1620 |
| gatgaaaatg | gtaaatatca | gttcactggt | ttaagcaatg | gaacttatag | tgtagagttt | 1680 |
| tcaacaccag | ccggttatac | accgacaact | gcaaatgtag | gtacagatga | tgctgtagat | 1740 |
| tctgatggac | taactacaac | aggtgtcatt | aaagacgctg | acaacatgac | attagatagt | 1800 |
| ggattctaca | aaacaccaaa | atatagttta | ggtgattatg | tttggtacga | cagtaataaa | 1860 |
| gatggtaaac | gagattcgac | tgaaaaagga | attaaaggtg | ttaaagttac | tttgcaaaac | 1920 |
| gaaaaaggcg | aagtaattgg | tacaactgaa | acagatgaaa | atggtaaata | ccgctttgat | 1980 |

-continued

```
aatttagata gtggtaaata caaagttatc tttgaaaaac ctgctggctt aactcaaaca    2040
ggtacaaata caactgaaga tgataaagat gccgatggtg gcgaagttga tgtaacaatt    2100
acggatcatg atgatttcac acttgataat ggctactacg aagaagaaac atcagatagc    2160
gactcagatt ctgacagcga ttcagactca gatagcgact cagattcaga tagcgactca    2220
gattcagaca gcgattcaga cagcgactca gactcagata gcgattcaga ttcagacagc    2280
gactcagact cagacagcaa ttcagactcg gatagcgact cagactcaga tagcgactca    2340
gattcggata gcgactcaga ctcagatagc gattcagatt cagatagcga ttcggactca    2400
gacagtgatt cagattcaga ctcagatagc gactcagatt ctgacagcga ttcagactca    2460
gacagcgact cagactcaga cagtgattca gattcagaca gcgactcaga ttcagatagc    2520
gactcagact cagatagcga ctcagactca gatagcgact cagactcgga tagcgattca    2580
gattcagaca gcgactcaga ttcagatagc gattcggact cagacaacga ctcagattca    2640
gatagcgatt cagattcaga tgcaggtaaa catactccgg ctaaaccaat gagtacggtt    2700
aaagatcagc ataaaacagc taaagcatta ccagaaacag gtagtgaaaa taataattca    2760
aataatggca cattattcgg tggattattc gcggcattag gatcattatt gtcattcggt    2820
cgtcgtaaaa aacaaaataa a                                              2841
```

<210> SEQ ID NO 5
<211> LENGTH: 1315
<212> TYPE: PRT
<213> ORGANISM: Staphylococcus aureus

<400> SEQUENCE: 5

```
Met Leu Asn Arg Glu Asn Lys Thr Ala Ile Thr Arg Lys Gly Met Val
 1               5                  10                  15

Ser Asn Arg Leu Asn Lys Phe Ser Ile Arg Lys Tyr Thr Val Gly Thr
            20                  25                  30

Ala Ser Ile Leu Val Gly Thr Thr Leu Ile Phe Gly Leu Gly Asn Gln
        35                  40                  45

Glu Ala Lys Ala Ala Glu Ser Thr Asn Lys Glu Leu Asn Glu Ala Thr
    50                  55                  60

Thr Ser Ala Ser Asp Asn Gln Ser Ser Asp Lys Val Asp Met Gln Gln
65                  70                  75                  80

Leu Asn Gln Glu Asp Asn Thr Lys Asn Asp Asn Gln Lys Glu Met Val
                85                  90                  95

Ser Ser Gln Gly Asn Glu Thr Thr Ser Asn Gly Asn Lys Leu Ile Glu
            100                 105                 110

Lys Glu Ser Val Gln Ser Thr Thr Gly Asn Lys Val Glu Val Ser Thr
        115                 120                 125

Ala Lys Ser Asp Glu Gln Ala Ser Pro Lys Ser Thr Asn Glu Asp Leu
    130                 135                 140

Asn Thr Lys Gln Thr Ile Ser Asn Gln Glu Ala Leu Gln Pro Asp Leu
145                 150                 155                 160

Gln Glu Asn Lys Ser Val Val Asn Val Gln Pro Thr Asn Glu Glu Asn
                165                 170                 175

Lys Lys Val Asp Ala Lys Thr Glu Ser Thr Thr Leu Asn Val Lys Ser
            180                 185                 190

Asp Ala Ile Lys Ser Asn Asp Glu Thr Leu Val Asp Asn Asn Ser Asn
        195                 200                 205

Ser Asn Asn Glu Asn Asn Ala Asp Ile Ile Leu Pro Lys Ser Thr Ala
    210                 215                 220
```

```
Pro Lys Arg Leu Asn Thr Arg Met Arg Ile Ala Ala Val Gln Pro Ser
225                 230                 235                 240

Ser Thr Glu Ala Lys Asn Val Asn Asp Leu Ile Thr Ser Asn Thr Thr
                245                 250                 255

Leu Thr Val Val Asp Ala Asp Lys Asn Asn Lys Ile Val Pro Ala Gln
                260                 265                 270

Asp Tyr Leu Ser Leu Lys Ser Gln Ile Thr Val Asp Asp Lys Val Lys
                275                 280                 285

Ser Gly Asp Tyr Phe Thr Ile Lys Tyr Ser Asp Thr Val Gln Val Tyr
290                 295                 300

Gly Leu Asn Pro Glu Asp Ile Lys Asn Ile Gly Asp Ile Lys Asp Pro
305                 310                 315                 320

Asn Asn Gly Glu Thr Ile Ala Thr Ala Lys His Asp Thr Ala Asn Asn
                325                 330                 335

Leu Ile Thr Tyr Thr Phe Thr Asp Tyr Val Asp Arg Phe Asn Ser Val
                340                 345                 350

Gln Met Gly Ile Asn Tyr Ser Ile Tyr Met Asp Ala Asp Thr Ile Pro
                355                 360                 365

Val Ser Lys Asn Asp Val Glu Phe Asn Val Thr Ile Gly Asn Thr Thr
370                 375                 380

Thr Lys Thr Thr Ala Asn Ile Gln Tyr Pro Asp Tyr Val Val Asn Glu
385                 390                 395                 400

Lys Asn Ser Ile Gly Ser Ala Phe Thr Glu Thr Val Ser His Val Gly
                405                 410                 415

Asn Lys Glu Asn Pro Gly Tyr Tyr Lys Gln Thr Ile Tyr Val Asn Pro
                420                 425                 430

Ser Glu Asn Ser Leu Thr Asn Ala Lys Leu Lys Val Gln Ala Tyr His
                435                 440                 445

Ser Ser Tyr Pro Asn Asn Ile Gly Gln Ile Asn Lys Asp Val Thr Asp
                450                 455                 460

Ile Lys Ile Tyr Gln Val Pro Lys Gly Tyr Thr Leu Asn Lys Gly Tyr
465                 470                 475                 480

Asp Val Asn Thr Lys Glu Leu Thr Asp Val Thr Asn Gln Tyr Leu Gln
                485                 490                 495

Lys Ile Thr Tyr Gly Asp Asn Ser Ala Val Ile Asp Phe Gly Asn
                500                 505                 510

Ala Asp Ser Ala Tyr Val Val Met Val Asn Thr Lys Phe Gln Tyr Thr
                515                 520                 525

Asn Ser Glu Ser Pro Thr Leu Val Gln Met Ala Thr Leu Ser Ser Thr
                530                 535                 540

Gly Asn Lys Ser Val Ser Thr Gly Asn Ala Leu Gly Phe Thr Asn Asn
545                 550                 555                 560

Gln Ser Gly Gly Ala Gly Gln Glu Val Tyr Lys Ile Gly Asn Tyr Val
                565                 570                 575

Trp Glu Asp Thr Asn Lys Asn Gly Val Gln Glu Leu Gly Glu Lys Gly
                580                 585                 590

Val Gly Asn Val Thr Val Thr Val Phe Asp Asn Asn Thr Asn Thr Lys
                595                 600                 605

Val Gly Glu Ala Val Thr Lys Glu Asp Gly Ser Tyr Leu Ile Pro Asn
                610                 615                 620

Leu Pro Asn Gly Asp Tyr Arg Val Glu Phe Ser Asn Leu Pro Lys Gly
625                 630                 635                 640
```

-continued

Tyr Glu Val Thr Pro Ser Lys Gln Gly Asn Asn Glu Leu Asp Ser
            645                 650                 655

Asn Gly Leu Ser Ser Val Ile Thr Val Asn Gly Lys Asp Asn Leu Ser
            660                 665                 670

Ala Asp Leu Gly Ile Tyr Lys Pro Lys Tyr Asn Leu Gly Asp Tyr Val
            675                 680                 685

Trp Glu Asp Thr Asn Lys Asn Gly Ile Gln Asp Gln Asp Glu Lys Gly
        690                 695                 700

Ile Ser Gly Val Thr Val Thr Leu Lys Asp Glu Asn Gly Asn Val Leu
705                 710                 715                 720

Lys Thr Val Thr Thr Asp Ala Asp Gly Lys Tyr Lys Phe Thr Asp Leu
                725                 730                 735

Asp Asn Gly Asn Tyr Lys Val Glu Phe Thr Thr Pro Glu Gly Tyr Thr
            740                 745                 750

Pro Thr Thr Val Thr Ser Gly Ser Asp Ile Glu Lys Asp Ser Asn Gly
            755                 760                 765

Leu Thr Thr Thr Gly Val Ile Asn Gly Ala Asp Asn Met Thr Leu Asp
            770                 775                 780

Ser Gly Phe Tyr Lys Thr Pro Lys Tyr Asn Leu Gly Asn Tyr Val Trp
785                 790                 795                 800

Glu Asp Thr Asn Lys Asp Gly Lys Gln Asp Ser Thr Glu Lys Gly Ile
                805                 810                 815

Ser Gly Val Thr Val Thr Leu Lys Asn Glu Asn Gly Glu Val Leu Gln
            820                 825                 830

Thr Thr Lys Thr Asp Lys Asp Gly Lys Tyr Gln Phe Thr Gly Leu Glu
            835                 840                 845

Asn Gly Thr Tyr Lys Val Glu Phe Glu Thr Pro Ser Gly Tyr Thr Pro
850                 855                 860

Thr Gln Val Gly Ser Gly Thr Asp Glu Gly Ile Asp Ser Asn Gly Thr
865                 870                 875                 880

Ser Thr Thr Gly Val Ile Lys Asp Lys Asp Asn Asp Thr Ile Asp Ser
            885                 890                 895

Gly Phe Tyr Lys Pro Thr Tyr Asn Leu Gly Asp Tyr Val Trp Glu Asp
            900                 905                 910

Thr Asn Lys Asn Gly Val Gln Asp Lys Asp Glu Lys Gly Ile Ser Gly
            915                 920                 925

Val Thr Val Thr Leu Lys Asp Glu Asn Asp Lys Val Leu Lys Thr Val
930                 935                 940

Thr Thr Asp Glu Asn Gly Lys Tyr Gln Phe Thr Asp Leu Asn Asn Gly
945                 950                 955                 960

Thr Tyr Lys Val Glu Phe Glu Thr Pro Ser Gly Tyr Thr Pro Thr Ser
                965                 970                 975

Val Thr Ser Gly Asn Asp Thr Glu Lys Asp Ser Asn Gly Leu Thr Thr
            980                 985                 990

Thr Gly Val Ile Lys Asp Ala Asp Asn Met Thr Leu Asp Ser Gly Phe
        995                 1000                1005

Tyr Lys Thr Pro Lys Tyr Ser Leu Gly Asp Tyr Val Trp Tyr Asp Ser
    1010                1015                1020

Asn Lys Asp Gly Lys Gln Asp Ser Thr Glu Lys Gly Ile Lys Asp Val
1025                1030                1035                1040

Lys Val Thr Leu Leu Asn Glu Lys Gly Glu Val Ile Gly Thr Thr Lys
                1045                1050                1055

Thr Asp Glu Asn Gly Lys Tyr Cys Phe Asp Asn Leu Asp Ser Gly Lys

```
                    1060            1065            1070
Tyr Lys Val Ile Phe Glu Lys Pro Ala Gly Leu Thr Gln Thr Gly Thr
        1075            1080            1085

Asn Thr Thr Glu Asp Asp Lys Asp Ala Asp Gly Gly Glu Val Asp Val
    1090            1095            1100

Thr Ile Thr Asp His Asp Asp Phe Thr Leu Asp Asn Gly Tyr Tyr Glu
1105            1110            1115            1120

Glu Glu Thr Ser Asp Ser Asp Ser Asp Ser Asp Ser Asp Ser Asp Ser
                1125            1130            1135

Asp Arg Asp Ser Asp Ser Asp Ser Asp Ser Asp Ser Asp Ser Asp Ser
        1140            1145            1150

Asp Ser Asp Ser Asp Ser Asp Ser Asp Ser Asp Ser Asp Ser Asp Arg
    1155            1160            1165

Asp Ser Asp Ser Asp Ser Asp Ser Asp Ser Asp Ser Asp Ser Asp Ser
1170            1175            1180

Asp Ser Asp Ser Asp Ser Asp Ser Asp Ser Asp Ser Asp Ser Asp Ser
1185            1190            1195            1200

Asp Ser Asp Ser Asp Ser Asp Ser Asp Ser Asp Ser Asp Ser Asp Ser
                1205            1210            1215

Asp Ser Asp Ser Asp Ser Asp Ser Asp Ser Asp Ser Asp Ser Asp Ser
        1220            1225            1230

Asp Ser Asp Ser Asp Ser Asp Ser Asp Ser Asp Ser Asp Ser Asp Ser
    1235            1240            1245

Asp Ser Asp Ser Asp Ser Asp Ala Gly Lys His Thr Pro Val Lys Pro
1250            1255            1260

Met Ser Thr Thr Lys Asp His His Asn Lys Ala Lys Ala Leu Pro Glu
1265            1270            1275            1280

Thr Gly Asn Glu Asn Ser Gly Ser Asn Asn Ala Thr Leu Phe Gly Gly
                1285            1290            1295

Leu Phe Ala Ala Leu Gly Ser Leu Leu Leu Phe Gly Arg Arg Lys Lys
        1300            1305            1310

Gln Asn Lys
    1315

<210> SEQ ID NO 6
<211> LENGTH: 3945
<212> TYPE: DNA
<213> ORGANISM: Staphylococcus aureus

<400> SEQUENCE: 6
atgctaaaca gagaaaataa aacggcaata acaaggaaag gcatggtatc caatcgatta      60
aataaatttt cgattagaaa gtacacagtg ggaacagcat caatttttagt aggtacaaca     120 ttaattttttg gtctggggaa ccaagaagca aaggctgcag aaagtactaa taaagaattg     180
aacgaagcga caacttcagc aagtgataat caatcgagtg ataaagttga tatgcagcaa     240
ctaaatcaag aagacaatac taaaaatgat aatcaaaaag aaatggtatc atctcaaggt     300
aatgaaacga cttcaaatgg gaataaatta atagaaaaag aaagtgtaca atctaccact     360
ggaaataaag ttgaagtttc aactgccaaa tcagatgagc aagcttcacc aaaatctacg     420
aatgaagatt taaacactaa acaaactata gtaatcaag aagcgttaca acctgatttg      480
caagagaata atcagtggt aaatgttcaa ccaactaatg aggaaaacaa aaaggtagat      540
gccaaaactg aatcaactac attaaatgtt aaaagtgatg ctatcaagag taatgatgaa     600
actcttgttg ataacaatag taattcaaat aatgaaaata atgcagatat cattttgcca     660
```

```
aaaagtacag cacctaaacg tttgaataca agaatgcgta tagcagcagt acagccatca    720
tcaacagagg ctaaaaatgt taatgattta atcacatcaa atacaacatt aactgtcgtt    780
gatgcagata aaaacaataa aatcgtacca gcccaagatt atttatcatt aaaatcacaa    840
attacagttg atgacaaagt taaatcaggt gattatttca caattaaata ctcagataca    900
gtacaagtat atggattgaa tccggaagat attaaaaata ttggtgatat taaagatcca    960
aataatggtg aaacaattgc gactgcaaaa catgatactg caaataattt aattacatat   1020
acatttacag attatgttga tcgatttaat tctgtacaaa tgggaattaa ttattcaatt   1080
tatatggatg ctgatacaat tcctgttagt aaaaacgatg ttgagtttaa tgttacgata   1140
ggtaatacta caacaaaaac aactgctaac attcaatatc cagattatgt tgtaaatgag   1200
aaaaattcaa ttggatcagc gttcactgaa acagtttcac atgttggaaa taagaaaat    1260 ccagggtact ataaacaaac gatttatgta atccatcgg aaaattcttt aacaaatgcc    1320
aaactaaaag ttcaagctta ccactcaagt tatcctaata atatcgggca aataaataaa   1380
gatgtaacag atataaaaat atatcaagtt cctaaaggtt atacattaaa taaggatac    1440 gatgtgaata ctaaagagct tacagatgta acaaatcaat acttgcagaa aattacatat   1500
ggcgacaaca atagcgctgt tattgatttt ggaaatgcag attctgctta tgttgtaatg   1560
gttaatacaa aattccaata tacaaatagc gaaagcccaa cacttgttca aatggctact   1620
ttatcttcaa caggtaataa atccgtttct actggcaatg ctttaggatt tactaataac   1680
caaagtggcg gagctggtca agaagtatat aaaattggta actacgtatg ggaagatact   1740
aataaaaacg gtgttcaaga attaggagaa aaaggcgttg gcaatgtaac tgtaactgta   1800
tttgataata atacaaatac aaaagtagga gaagcagtta ctaaagaaga tgggtcatac   1860
ttgattccaa acttacctaa tggagattac cgtgtagaat tttcaaactt accaaaaggt   1920
tatgaagtaa cccccttcaaa acaaggtaat aacgaagaat tagattcaaa cggcttatct   1980
tcagttatta cagttaatgg caaagataac ttatctgcag acttaggtat ttacaaacct   2040
aaatacaact taggtgacta tgtctgggaa gatacaaata aaaatggtat ccaagaccaa   2100
gatgaaaaag gtatatctgg cgtaacggta acattaaaag atgaaaacgg taacgtgtta   2160
aaaacagtta caacagacgc tgatggcaaa tataaattta ctgatttaga taatggtaat   2220 tataagttg aatttactac accagaaggc tatacaccga ctacagtaac atctggtagc   2280
gacattgaaa aagactctaa tggtttaaca acaacaggtg ttattaatgg tgctgataac   2340
atgacattag atagtggatt ctacaaaaca ccaaaatata atttaggtaa ttatgtatgg   2400
gaagatacaa ataaagatgg taagcaggat tcaactgaaa aaggtatttc aggcgtaaca   2460
gttacattga aaaatgaaaa cggtgaagtt ttacaaacaa ctaaaacaga taaagatggt   2520
aaatatcaat ttactggatt agaaaatgga acttataaag ttgaattcga acaccatca    2580 ggttacacac caacacaagt aggttcagga actgatgaag gtatagattc aaatggtaca   2640
tcaacaacag gtgtcattaa agataaagat aacgatacta ttgactctgg ttttctacaaa   2700 ccgacttaca acttaggtga ctatgtatgg gaagatacaa ataaaaacgg tgttcaagat   2760
aaagatgaaa agggcatttc aggtgtaaca gttacgttaa aagatgaaaa cgacaaagtt   2820
ttaaaaacag ttacaacaga tgaaaatggt aaatatcaat tcactgattt aaacaatgga   2880
acttataaag ttgaattcga gacaccatca ggttatacac caacttcagt aacttctgga   2940
aatgatactg aaaagattc taatggttta acaacaacag gtgtcattaa agatgcagat   3000
```

-continued

```
aacatgacat tagacagtgg tttctataaa acaccaaaat atagtttagg tgattatgtt    3060
tggtacgaca gtaataaaga cggcaaacaa gattcaactg aaaaaggtat caaagatgtt    3120
aaagttactt tattaaatga aaaaggcgaa gtaattggaa caactaaaac agatgaaaat    3180
ggtaaatact gctttgataa tttagatagc ggtaaataca aagttatttt tgaaaagcct    3240
gctggcttaa cacaaacagg tacaaataca actgaagatg ataaagatgc agatggtggc    3300
gaagttgacg taacaattac ggatcatgat gatttcacac ttgataatgg ctactacgaa    3360
gaagaaacat cagatagcga ctcagattcg gacagcgact cagattcaga cagagactca    3420
gactcagata gtgattcaga ctcggatagc gattcagatt cagacagcga ttcagattca    3480
gatagcgatt cagattcaga cagagactca gatagtgatt cagactcaga tagcgactca    3540
gattcagaca gcgactcaga ttcagacagc gactcagact cagatagtga ttcagactca    3600
gatagcgact cagattcgga tagcgactca gattcagaca gcgactcaga ctcggatagt    3660
gattcagact cagatagcga ctcagactca gatagcgatt cagattcaga tagcgactca    3720
gactcagaca gcgattcaga ctcagacagc gactcagact cagatgcagg taagcacaca    3780
cctgttaaac caatgagtac tactaaagac catcacaata aagcaaaagc attaccagaa    3840
acaggtaatg aaaatagcgg ctcaaataac gcaacgttat ttggcggatt attcgcagca    3900
ttaggatcat tattgttatt cggtcgtcgt aaaaaacaaa ataaa                   3945
```

<210> SEQ ID NO 7
<211> LENGTH: 1166
<212> TYPE: PRT
<213> ORGANISM: Staphylococcus aureus

<400> SEQUENCE: 7

```
Met Ile Asn Arg Asp Asn Lys Lys Ala Ile Thr Lys Lys Gly Met Ile
1               5                   10                  15

Ser Asn Arg Leu Asn Lys Phe Ser Ile Arg Lys Tyr Thr Val Gly Thr
            20                  25                  30

Ala Ser Ile Leu Val Gly Thr Thr Leu Ile Phe Gly Leu Gly Asn Gln
        35                  40                  45

Glu Ala Lys Ala Ala Glu Asn Thr Ser Thr Glu Asn Ala Lys Gln Asp
    50                  55                  60

Asp Ala Thr Thr Ser Asp Asn Lys Glu Val Val Ser Glu Thr Glu Asn
65                  70                  75                  80

Asn Ser Thr Thr Glu Asn Asn Ser Thr Asn Pro Ile Lys Lys Glu Thr
                85                  90                  95

Asn Thr Asp Ser Gln Pro Glu Ala Lys Lys Glu Ser Thr Ser Ser Ser
            100                 105                 110

Thr Gln Lys Gln Gln Asn Asn Val Thr Ala Thr Thr Glu Thr Lys Pro
        115                 120                 125

Gln Asn Ile Glu Lys Glu Asn Val Lys Pro Ser Thr Asp Lys Thr Ala
    130                 135                 140

Thr Glu Asp Thr Ser Val Ile Leu Glu Glu Lys Lys Ala Pro Asn Asn
145                 150                 155                 160

Thr Asn Asn Asp Val Thr Thr Lys Pro Ser Thr Ser Glu Pro Ser Thr
                165                 170                 175

Ser Glu Ile Gln Thr Lys Pro Thr Pro Gln Glu Ser Thr Asn Ile
            180                 185                 190

Glu Asn Ser Gln Pro Gln Pro Thr Pro Ser Lys Val Asp Asn Gln Val
        195                 200                 205
```

-continued

```
Thr Asp Ala Thr Asn Pro Lys Glu Pro Val Asn Val Ser Lys Glu Glu
    210                 215                 220
Leu Lys Asn Asn Pro Glu Lys Leu Lys Glu Leu Val Arg Asn Asp Ser
225                 230                 235                 240
Asn Thr Asp His Ser Thr Lys Pro Val Ala Thr Ala Pro Thr Ser Val
                245                 250                 255
Ala Pro Lys Arg Val Asn Ala Lys Met Arg Phe Ala Val Ala Gln Pro
            260                 265                 270
Ala Ala Val Ala Ser Asn Asn Val Asn Asp Leu Ile Lys Val Thr Lys
        275                 280                 285
Gln Thr Ile Lys Val Gly Asp Gly Lys Asp Asn Val Ala Ala Ala His
    290                 295                 300
Asp Gly Lys Asp Ile Glu Tyr Asp Thr Glu Phe Thr Ile Asp Asn Lys
305                 310                 315                 320
Val Lys Lys Gly Asp Thr Met Thr Ile Asn Tyr Asp Lys Asn Val Ile
                325                 330                 335
Pro Ser Asp Leu Thr Asp Lys Asn Asp Pro Ile Asp Ile Thr Asp Pro
            340                 345                 350
Ser Gly Glu Val Ile Ala Lys Gly Thr Phe Asp Lys Ala Thr Lys Gln
        355                 360                 365
Ile Thr Tyr Thr Phe Thr Asp Tyr Val Asp Lys Tyr Glu Asp Ile Lys
    370                 375                 380
Ser Arg Leu Thr Leu Tyr Ser Tyr Ile Asp Lys Lys Thr Val Pro Asn
385                 390                 395                 400
Glu Thr Ser Leu Asn Leu Thr Phe Ala Thr Ala Gly Lys Glu Thr Ser
                405                 410                 415
Gln Asn Val Thr Val Asp Tyr Gln Asp Pro Met Val His Gly Asp Ser
            420                 425                 430
Asn Ile Gln Ser Ile Phe Thr Lys Leu Asp Glu Asp Lys Gln Thr Ile
        435                 440                 445
Glu Gln Gln Ile Tyr Val Asn Pro Leu Lys Lys Ser Ala Thr Asn Thr
    450                 455                 460
Lys Val Asp Ile Ala Gly Ser Gln Val Asp Asp Tyr Gly Asn Ile Lys
465                 470                 475                 480
Leu Gly Asn Gly Ser Thr Ile Ile Asp Gln Asn Thr Glu Ile Lys Val
                485                 490                 495
Tyr Lys Val Asn Ser Asp Gln Gln Leu Pro Gln Ser Asn Arg Ile Tyr
            500                 505                 510
Asp Phe Ser Gln Tyr Glu Asp Val Thr Ser Gln Phe Asp Asn Lys Lys
        515                 520                 525
Ser Phe Ser Asn Asn Val Ala Thr Leu Asp Phe Gly Asp Ile Asn Ser
    530                 535                 540
Ala Tyr Ile Ile Lys Val Val Ser Lys Tyr Thr Pro Thr Ser Asp Gly
545                 550                 555                 560
Glu Leu Asp Ile Ala Gln Gly Thr Ser Met Arg Thr Thr Asp Lys Tyr
                565                 570                 575
Gly Tyr Tyr Asn Tyr Ala Gly Tyr Ser Asn Phe Ile Val Thr Ser Asn
            580                 585                 590
Asp Thr Gly Gly Gly Asp Gly Thr Val Lys Pro Glu Glu Lys Leu Tyr
        595                 600                 605
Lys Ile Gly Asp Tyr Val Trp Glu Asp Val Asp Lys Asp Gly Val Gln
    610                 615                 620
Gly Thr Asp Ser Lys Glu Lys Pro Met Ala Asn Val Leu Val Thr Leu
```

-continued

```
              625                 630                 635                 640
Thr Tyr Pro Asp Gly Thr Thr Lys Ser Val Arg Thr Asp Ala Asn Gly
                645                 650                 655

His Tyr Glu Phe Gly Gly Leu Lys Asp Gly Glu Thr Tyr Thr Val Lys
                660                 665                 670

Phe Glu Thr Pro Thr Gly Tyr Leu Pro Thr Lys Val Asn Gly Thr Thr
                675                 680                 685

Asp Gly Glu Lys Asp Ser Asn Gly Ser Ser Val Thr Val Lys Ile Asn
                690                 695                 700

Gly Lys Asp Asp Met Ser Leu Asp Thr Gly Phe Tyr Lys Glu Pro Lys
705                 710                 715                 720

Tyr Asn Leu Gly Asp Tyr Val Trp Glu Asp Thr Asn Lys Asp Gly Ile
                725                 730                 735

Gln Asp Ala Asn Glu Pro Gly Ile Lys Asp Val Lys Val Thr Leu Lys
                740                 745                 750

Asp Ser Thr Gly Lys Val Ile Gly Thr Thr Thr Thr Asp Ala Ser Gly
                755                 760                 765

Lys Tyr Lys Phe Thr Asp Leu Asp Asn Gly Asn Tyr Thr Val Glu Phe
                770                 775                 780

Glu Thr Pro Ala Gly Tyr Thr Pro Thr Val Lys Asn Thr Thr Ala Asp
785                 790                 795                 800

Asp Lys Asp Ser Asn Gly Leu Thr Thr Gly Val Ile Lys Asp Ala
                805                 810                 815

Asp Asn Met Thr Leu Asp Arg Gly Phe Tyr Lys Thr Pro Lys Tyr Ser
                820                 825                 830

Leu Gly Asp Tyr Val Trp Tyr Asp Ser Asn Lys Asp Gly Lys Gln Asp
                835                 840                 845

Ser Thr Glu Lys Gly Ile Lys Asp Val Thr Val Thr Leu Gln Asn Glu
                850                 855                 860

Lys Gly Glu Val Ile Gly Thr Thr Lys Thr Asp Glu Asn Gly Lys Tyr
865                 870                 875                 880

Arg Phe Asp Asn Leu Asp Ser Gly Lys Tyr Lys Val Ile Phe Glu Lys
                885                 890                 895

Pro Ala Gly Leu Thr Gln Thr Val Thr Asn Thr Thr Glu Asp Asp Lys
                900                 905                 910

Asp Ala Asp Gly Gly Glu Val Asp Val Thr Ile Thr Asp His Asp Asp
                915                 920                 925

Phe Thr Leu Asp Asn Gly Tyr Phe Glu Glu Asp Thr Ser Asp Ser Asp
                930                 935                 940

Ser Asp Ser Asp Ser Asp Ser Asp Ser Asp Ser Asp Ser Asp Ser Asp
945                 950                 955                 960

Ser Asp Ser Asp Ser Asp Ser Asp Ser Asp Ser Asp Ser Asp Ser Asp
                965                 970                 975

Ser Asp Ser Asp Ser Asp Ser Asp Ser Asp Ser Asp Ser Asp Ser Asp
                980                 985                 990

Ser Asp Ser Asp Ser Asp Ser Asp Ser Asp Ser Asp Ser Asp Ser Asp
                995                1000                1005

Ser Asp Ser Asp Ser Asp Ser Asp Ser Asp Ser Asp Ser Asp Ser Asp
     1010               1015                1020

Ser Asp Ser Asp Ser Asp Ser Asp Ser Asp Ser Asp Ser Asp Ser Asp
1025                1030                1035                1040

Ser Asp Ser Asp Ser Asp Ser Asp Ser Asp Ser Asp Ser Asp Ser Asp
                1045                1050                1055
```

Ser Asp Ser Asp Ser Asp Ser Asp Ser Asp Ser Asp Ser Asp
        1060                1065                1070

Ser Asp Ser Asp Ser Asp Ser Asp Ser Asp Ser Asp Ser Asp
    1075                1080                1085

Ser Asp Ser Asp Ser Asp Ser Asp Ser Asp Ser Asp Ser Asp
1090                1095                1100

Ser Asp Ala Gly Lys His Thr Pro Val Lys Pro Met Ser Thr Thr Lys
1105                1110                1115                1120

Asp His His Asn Lys Ala Lys Ala Leu Pro Glu Thr Gly Ser Glu Asn
            1125                1130                1135

Asn Gly Ser Asn Asn Ala Thr Leu Phe Gly Gly Leu Phe Ala Ala Leu
        1140                1145                1150

Gly Ser Leu Leu Leu Phe Gly Arg Arg Lys Lys Gln Asn Lys
        1155                1160                1165

<210> SEQ ID NO 8
<211> LENGTH: 3498
<212> TYPE: DNA
<213> ORGANISM: Staphylococcus aureus

<400> SEQUENCE: 8

| | | | | | |
|---|---|---|---|---|---|
| atgattaaca | gggataataa | aaaggcaata | acaaaaaagg | gtatgatttc | aaatcgctta | 60 |
| aacaaatttt | cgattagaaa | gtatactgta | ggaactgcat | cgattttagt | aggtacgaca | 120 |
| ttgattttg | gtctagggaa | ccaagaagct | aaagctgctg | aaaacactag | tacagaaaat | 180 |
| gcaaaacaag | atgatgcaac | gactagtgat | aataagaag | tagtgtcgga | aactgaaaat | 240 |
| aattcgacaa | cagaaaataa | ttcaacaaat | ccaattaaga | agaaacaaa | tactgattca | 300 |
| caaccagaag | ctaaaaaaga | atcaacttca | tcaagtactc | aaaaacagca | aataacgtt | 360 |
| acagctacaa | ctgaaactaa | gcctcaaaac | attgaaaaag | aaatgttaa | accttcaact | 420 |
| gataaaactg | cgacagaaga | tacatctgtt | attttagaag | agaagaaagc | accaaataat | 480 |
| acaaataacg | atgtaactac | aaaaccatct | acaagtgaac | catctacaag | tgaaattcaa | 540 |
| acaaaaccaa | ctacacctca | agaatctaca | aatattgaaa | attcacaacc | gcaaccaacg | 600 |
| ccttcaaaag | tagacaatca | agttacagat | gcaactaatc | aaaagaacc | agtaaatgtg | 660 |
| tcaaagaag | aacttaaaaa | taatcctgag | aaattaaaag | aattggttag | aaatgatagc | 720 |
| aatacagatc | attcaactaa | accagttgct | acagctccaa | caagtgttgc | accaaaacgt | 780 |
| gtaaacgcaa | aaatgcgctt | tgcagttgca | caaccagcag | cagttgcttc | aaacaatgta | 840 |
| aatgatttaa | ttaaagtgac | gaagcaaaca | atcaaagttg | gcgatggtaa | agataatgtg | 900 |
| gcagcagcgc | atgacggtaa | agatattgaa | tatgatacag | agtttacaat | tgacaataaa | 960 |
| gtcaaaaaag | gcgatacaat | gacgattaat | tatgataaga | atgtaattcc | ttcggattta | 1020 |
| acagataaaa | atgatcctat | cgatattact | gatccatcag | agaggtcat | tgctaaagga | 1080 |
| acatttgata | agcaactaa | gcaaatcaca | tatacattta | cagactatgt | agataaatat | 1140 |
| gaagatataa | aatcacgctt | aactctatat | tcgtatattt | ataaaaaaac | agttccaaat | 1200 |
| gagacaagtt | tgaatttaac | atttgctaca | gcaggtaaag | aaacaagcca | aaatgtcact | 1260 |
| gttgattatc | aagatccaat | ggtccatggt | gattcaaaca | ttcaatctat | ctttacaaaa | 1320 |
| ttagatgaag | ataagcaaac | tattgaacaa | caaattatg | ttaacccatt | gaaaaaatca | 1380 |
| gcaaccaaca | ctaaagttga | tatagctggt | agtcaagtag | atgattatgg | aaatattaaa | 1440 |
| ctaggaaatg | gtagcaccat | tattgaccaa | aatacagaaa | taaggtttta | taagttaac | 1500 |

```
tctgatcaac aattgcctca aagtaataga atctatgatt ttagtcaata cgaagatgta    1560
acaagtcaat tgataataa aaaatcattt agtaataatg tagcaacatt ggattttggt    1620
gatattaatt cagcctatat tatcaaagtt gttagtaaat atacacctac atcagatggc    1680
gaactagata ttgcccaagg tactagtatg agaacaactg ataaatatgg ttattataat    1740
tatgcaggat attcaaactt catcgtaact tctaatgaca ctggcggtgg cgacggtact    1800
gttaaacctg aagaaagtt atacaaaatt ggtgactatg tatgggaaga cgttgataaa    1860
gacggtgttc aaggtacaga ttcaaaagaa aaaccaatgg caaacgtttt agttacatta    1920
acttacccgg acggtactac aaaatcagta agaacagatg ctaatggtca ttatgaattc    1980
ggtggtttga agacggaga aacttataca gttaaattcg aaacgccaac tggatatctt    2040
ccaacaaaag taaatggaac aactgatggt gaaaaagact caaatggtag ttcggttact    2100
gttaaaatta atggtaaaga tgatatgtct ttagatactg gttttacaa agaacctaaa    2160 tacaacttag gtgactatgt atgggaagat actaataaag atggtatcca agatgcaaat    2220
gagccaggaa tcaaagatgt taaggttaca ttaaaagata gtactggaaa agttattggt    2280
acaactacta ctgatgcctc gggtaaatat aaatttacag atttagataa tggtaactat    2340
acagtagaat ttgaaacacc agcaggttac acgccaacgg ttaaaaatac tacagctgat    2400
gataaagatt ctaatggttt aacaacaaca ggtgtcatta aagatgcaga taatatgaca    2460
ttagacaggg gtttctataa aacaccaaaa tacagtttag gtgattatgt ttggtacgac    2520
agtaataaag acggcaaaca agattcaact gaaaaaggta tcaaagatgt gacagttaca    2580
ttgcaaaacg aaaaggcga agtaattgga acaactaaaa cagatgaaaa tggtaaatat    2640
cgtttcgata atttagatag cggtaaatac aaagttatt ttgaaaagcc tgctggctta    2700
acacaaacag ttacaaatac aactgaagat gataaagatg cagatggtgg cgaagttgac    2760
gtaacaatta cggatcatga tgatttcaca cttgataacg gatacttcga agaagataca    2820
tcagacagcg attcagactc agatagtgac tcagacagcg actcagactc agacagcgac    2880
tcagactcag acagtgattc agattcagac agcgactcag attcagatag cgactcagat    2940
tcggacagcg attcagactc agatagcgac tcagattcag atagcgattc agactcagac    3000
agcgactcag attcagatag cgattcggac tcagacagcg attcagactc agatagcgac    3060
tcagactcag acagcgactc agattcagat agcgattcgg actcagatag cgactcagat    3120
tcagacagcg attcagactc agatagcgac tcagattcag acagcgattc agactcagat    3180
agcgactcag actcagacag tgattcagat tcagacagcg actcagactc agatagcgac    3240
tcagattcag acagcgactc agactcagat agcgactcag actcagacag tgattcagac    3300
agcgattcag actcggatgc aggaaaacat acacctgtta aaccaatgag tactactaaa    3360
gaccatcaca taaagcaaa agcattacca gaaacaggta gtgaaataa cggctcaaat    3420 aacgcaacgt tatttggtgg attatttgca gcattaggtt cattattgtt attcggtcgt    3480
cgcaaaaaac aaaacaaa                                                 3498
```

<210> SEQ ID NO 9
<211> LENGTH: 18
<212> TYPE: DNA
<213> ORGANISM: Staphylococcus aureus
<220> FEATURE:
<221> NAME/KEY: misc_feature
<222> LOCATION: (6)..(6)
<223> OTHER INFORMATION: n = (a or c or t or g)
<220> FEATURE:

-continued

```
<221> NAME/KEY: misc_feature
<222> LOCATION: (12)..(12)
<223> OTHER INFORMATION: n = (a or c or t or g)

<400> SEQUENCE: 9
gaytcngayt cngayagy                                                    18

<210> SEQ ID NO 10
<211> LENGTH: 5
<212> TYPE: PRT
<213> ORGANISM: Staphylococcus aureus

<400> SEQUENCE: 10

Leu Pro Asp Thr Gly
1               5

<210> SEQ ID NO 11
<211> LENGTH: 5
<212> TYPE: PRT
<213> ORGANISM: Staphylococcus aureus

<400> SEQUENCE: 11

Asp Tyr Ser Asn Ser
1               5

<210> SEQ ID NO 12
<211> LENGTH: 6
<212> TYPE: PRT
<213> ORGANISM: Staphylococcus aureus

<400> SEQUENCE: 12

Phe Thr Asp Tyr Val Asn
1               5

<210> SEQ ID NO 13
<211> LENGTH: 5
<212> TYPE: PRT
<213> ORGANISM: Staphylococcus aureus
<220> FEATURE:
<221> NAME/KEY: misc_feature
<222> LOCATION: (2)..(2)
<223> OTHER INFORMATION: Xaa = (Unspecified amino acid)
<220> FEATURE:
<221> NAME/KEY: misc_feature
<222> LOCATION: (4)..(4)
<223> OTHER INFORMATION: Xaa = (Unspecified amino acid)

<400> SEQUENCE: 13

Asp Xaa Ser Xaa Ser
1               5

<210> SEQ ID NO 14
<211> LENGTH: 5
<212> TYPE: PRT
<213> ORGANISM: Staphylococcus aureus
<220> FEATURE:
<221> NAME/KEY: misc_feature
<222> LOCATION: (3)..(3)
<223> OTHER INFORMATION: Xaa = (Unspecified amino acid)

<400> SEQUENCE: 14

Leu Pro Xaa Thr Gly
1               5

<210> SEQ ID NO 15
<211> LENGTH: 33
<212> TYPE: DNA
```

<213> ORGANISM: Staphylococcus aureus

<400> SEQUENCE: 15
cgaggatcct caggacaatc gaacgataca acg    33

<210> SEQ ID NO 16
<211> LENGTH: 27
<212> TYPE: DNA
<213> ORGANISM: Staphylococcus aureus

<400> SEQUENCE: 16
cgaggtacca tttactgctg aatcacc    27

<210> SEQ ID NO 17
<211> LENGTH: 34
<212> TYPE: DNA
<213> ORGANISM: Staphylococcus aureus

<400> SEQUENCE: 17
cgaaagcttg tcagaacaat cgaacgatac aacg    34

<210> SEQ ID NO 18
<211> LENGTH: 9
<212> TYPE: PRT
<213> ORGANISM: Staphylococcus aureus

<400> SEQUENCE: 18

Thr Tyr Thr Phe Thr Asp Tyr Val Asp
 1               5

<210> SEQ ID NO 19
<211> LENGTH: 9
<212> TYPE: PRT
<213> ORGANISM: Staphylococcus aureus

<400> SEQUENCE: 19

Thr Tyr Thr Phe Thr Asn Tyr Val Asp
 1               5

<210> SEQ ID NO 20
<211> LENGTH: 9
<212> TYPE: PRT
<213> ORGANISM: Staphylococcus aureus

<400> SEQUENCE: 20

Thr Phe Val Phe Thr Asp Tyr Val Asn
 1               5

<210> SEQ ID NO 21
<211> LENGTH: 9
<212> TYPE: PRT
<213> ORGANISM: Staphylococcus aureus

<400> SEQUENCE: 21

Ile Tyr Thr Phe Thr Asp Tyr Val Asn
 1               5

<210> SEQ ID NO 22
<211> LENGTH: 5
<212> TYPE: PRT
<213> ORGANISM: Staphylococcus aureus

<400> SEQUENCE: 22

Leu Pro Glu Thr Gly

```
-continued

<210> SEQ ID NO 23
<211> LENGTH: 14
<212> TYPE: PRT
<213> ORGANISM: Staphylococcus aureus

<400> SEQUENCE: 23

Thr Ile Tyr Phe Thr Val Phe Thr Asp Asn Tyr Val Asp Asn
 1               5                  10
```